US009228171B2

(12) United States Patent
Arya et al.

(10) Patent No.: US 9,228,171 B2
(45) Date of Patent: Jan. 5, 2016

(54) REGULATORY B CELLS (TBREGS) AND THEIR USE

(75) Inventors: Bira Arya, Baltimore, MD (US); Purevdorj B. Olkhanud, Parkville, MD (US); Monica Bodogai, Baltimore, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 61 days.

(21) Appl. No.: 13/577,226

(22) PCT Filed: Feb. 4, 2011

(86) PCT No.: PCT/US2011/023789
§ 371 (c)(1),
(2), (4) Date: Aug. 3, 2012

(87) PCT Pub. No.: WO2011/097511
PCT Pub. Date: Aug. 11, 2011

(65) Prior Publication Data
US 2012/0308563 A1    Dec. 6, 2012

Related U.S. Application Data

(60) Provisional application No. 61/302,074, filed on Feb. 5, 2010.

(51) Int. Cl.
| *A61K 35/26* | (2015.01) |
| *A61K 35/28* | (2015.01) |
| *A61K 38/00* | (2006.01) |
| *C12N 5/0781* | (2010.01) |
| *A61K 35/12* | (2015.01) |

(52) U.S. Cl.
CPC ......... *C12N 5/0635* (2013.01); *A61K 2035/122* (2013.01); *A61K 2035/124* (2013.01); *C12N 2502/30* (2013.01)

(58) Field of Classification Search
None
See application file for complete search history.

(56) References Cited

FOREIGN PATENT DOCUMENTS

WO    WO 2009/131712 A2    10/2009

OTHER PUBLICATIONS

Kaufman et al., American J of Transplantation, 2010. v.10, supp2 abstract 123, pp. 1-37.*
Dono et al., Eur. J of Immunol, 1993, v.23,pp. 873-881).*
Revoltella et al., Hematol,J 2001, v.2001 pp. 161-171.*
Soma et al., Human Pathology, 2006, v.37, pp. 218-230.*
Kaufman et al., American J of transplantation, 2010, v.10,suppl.2 p. 30 , Abst. 123.*
Aklilu et al., "Depletion of normal B cells with rituximab as an adjunct to IL-2 therapy for renal cell carcinoma and melanoma," *Oxford Journals & Medicine Annuals of Oncology* 15(7): 1109-1114 (2004)(Abstract).
Amu "The expression and function of CD25 B cells in man and in mice," *University of Gothenburg, Department of Rheumatology and Inflammation Research*, 58 pages (2008).
Amu et al., "CD25-expressing B-lymphocytes in Rheumatic Diseases," *Scandinavian Journal of Immunology* 65:182-191 (2007).
Amu et al., "Regulatory B cells prevent and reverse allergic airway inflammation via FoxP3-positive T regulatory cells in a murine model," *The Journal of Allergy and Clinical Immunology* 125(5):1114-1124 (May 2010).
Clinical Trial NCT00626483, "Daclizumab in Treating Patients With Newly Diagnosed Glioblastoma Multiforme Undergoing Targeted Immunology and Temozolomide-Caused Lymphopenia," http://clinicaltrials.gov/ct/show/NCT00626483, 5 pages, (Feb. 28, 2008).
Inoue et al., "Inhibitory Effects of B Cells on Antitumor Immunity," *Cancer Research* 66(15):7741-7747 (2006).
Inoue et al., "Regulatory B Cells Inhibit Antitumor Immunity," *Cancer Research* 67(10):5059 (2007).
International Search Report from parent PCT Application No. PCT/US2011/023789, 3 pages (mailed on May 17, 2011).
Mauri and Ehrenstein., "The 'short' history of regulatory B cells," *TRENDS in Immunology* 29(1):34-40 (Dec. 3, 2007).
Mizoguchi and Bhan, "A Case for Regulatory B Cells," *Journal of Immunology* 176:705-710 (2006).
Mizuguchi, "A double-edged sword in B-cell-targeted therapy for inflammatory diseases," *Expert Rev. Clin. Immunol.* 5(3):283-290 (2009).
Rech and Voderheide, "Clinical Use of Anti-CD25 Antibody Daclizumab to Enhance Immune Responses to Tumor Antigen Vaccination by Targeting Regulatory T cells," *Annals of the New York Academy of Sciences* 1174:99-106 (Sep. 2009).
Tretter et al., "Induction of CD4$^+$T-cell anergy and apoptosis by activated human B cells," *Blood* 112(12):4555-4564 (Dec. 1, 2008).
Zuckerma et al., The Role of Regulatory B-Cells in Chronic HCV Infection and Their Relation to HCV-Associated Autoimmunity, (printed from the internet on Aug. 26, 2010)(Abstract).

* cited by examiner

*Primary Examiner* — Michail Belyavskyi
(74) *Attorney, Agent, or Firm* — Klarquist Sparkman, LLP

(57) ABSTRACT

Regulatory B cells (tBreg) are disclosed herein. These regulatory B cells express CD25 (CD25$^+$) a pan B cell marker such as B220 (B220$^+$), and also express CD19 (CD19$^+$). These regulatory B cells suppress resting and activated T cells in cell contact-dependent manner. Methods for generating these regulatory B cells are also disclosed herein, as are methods for using these regulatory B cells to produce regulatory T cells (Treg). In some embodiments, methods for treating an immune-mediated disorder, such as an autoimmune disease, transplant rejection, graft-versus-host disease or inflammation, are disclosed. These methods include increasing regulatory B cell number or activity and/or by administering autologous regulatory B cells. Methods for treating cancer are also disclosed herein. These methods include decreasing regulatory B cell activity and/or number.

16 Claims, 39 Drawing Sheets

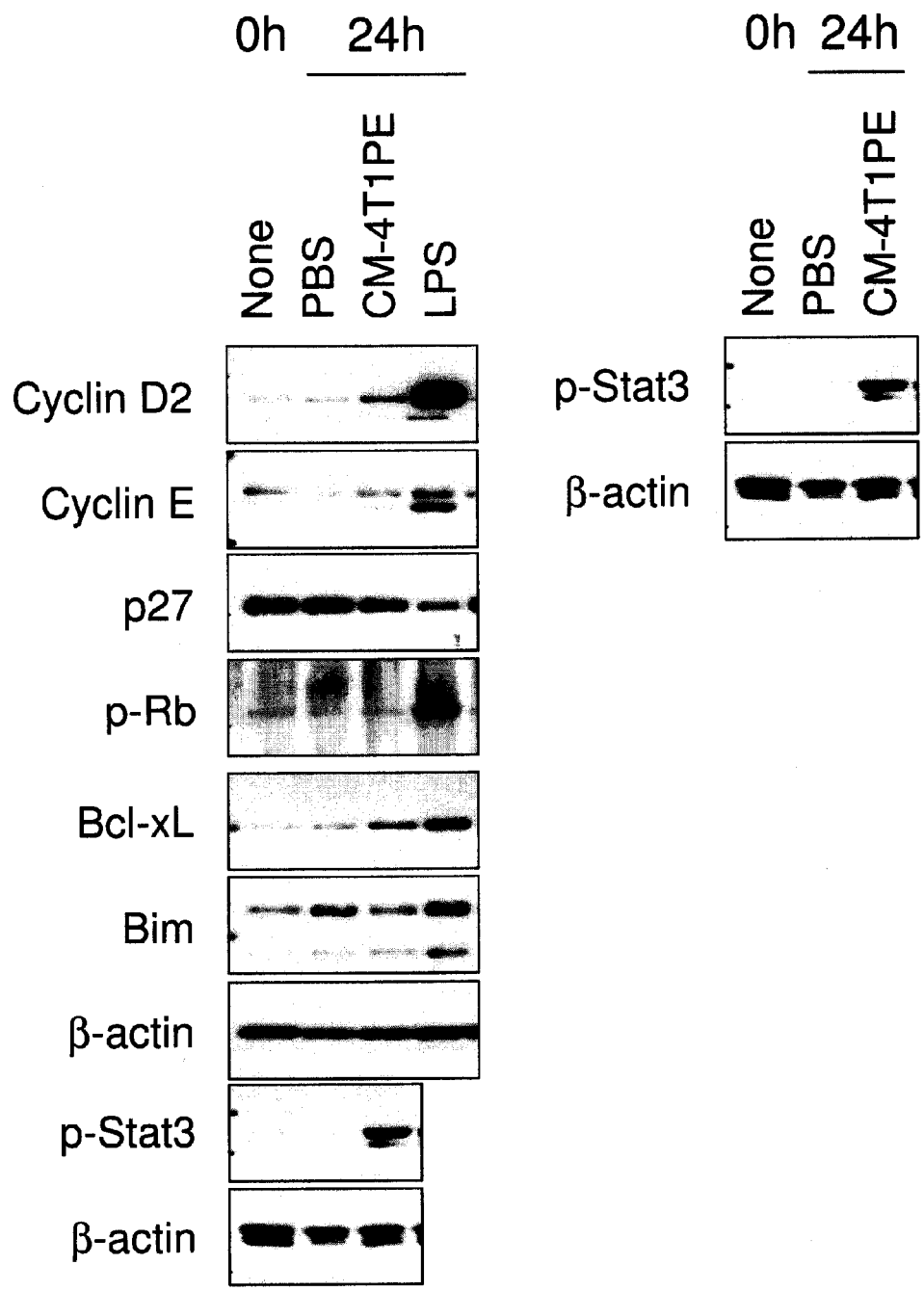

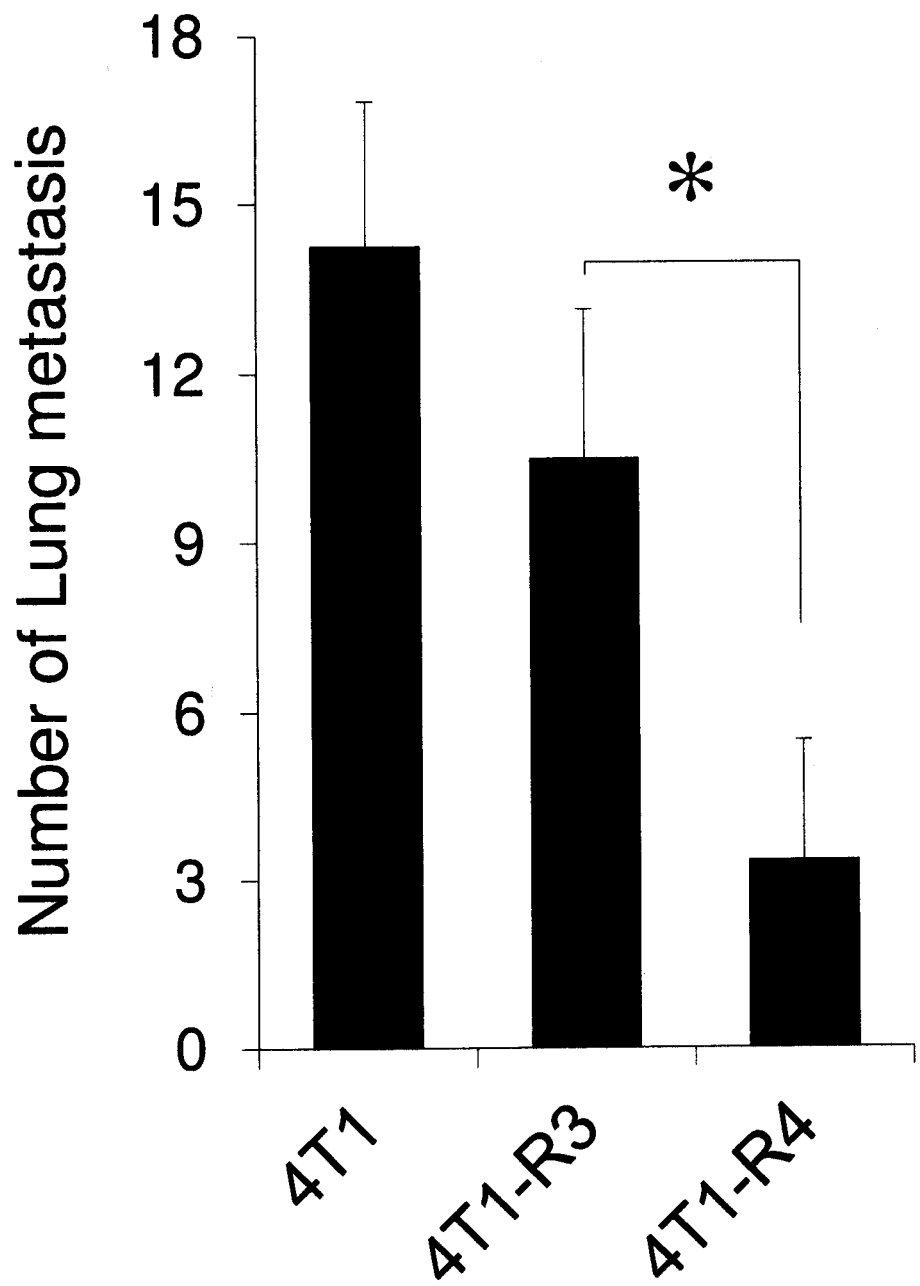

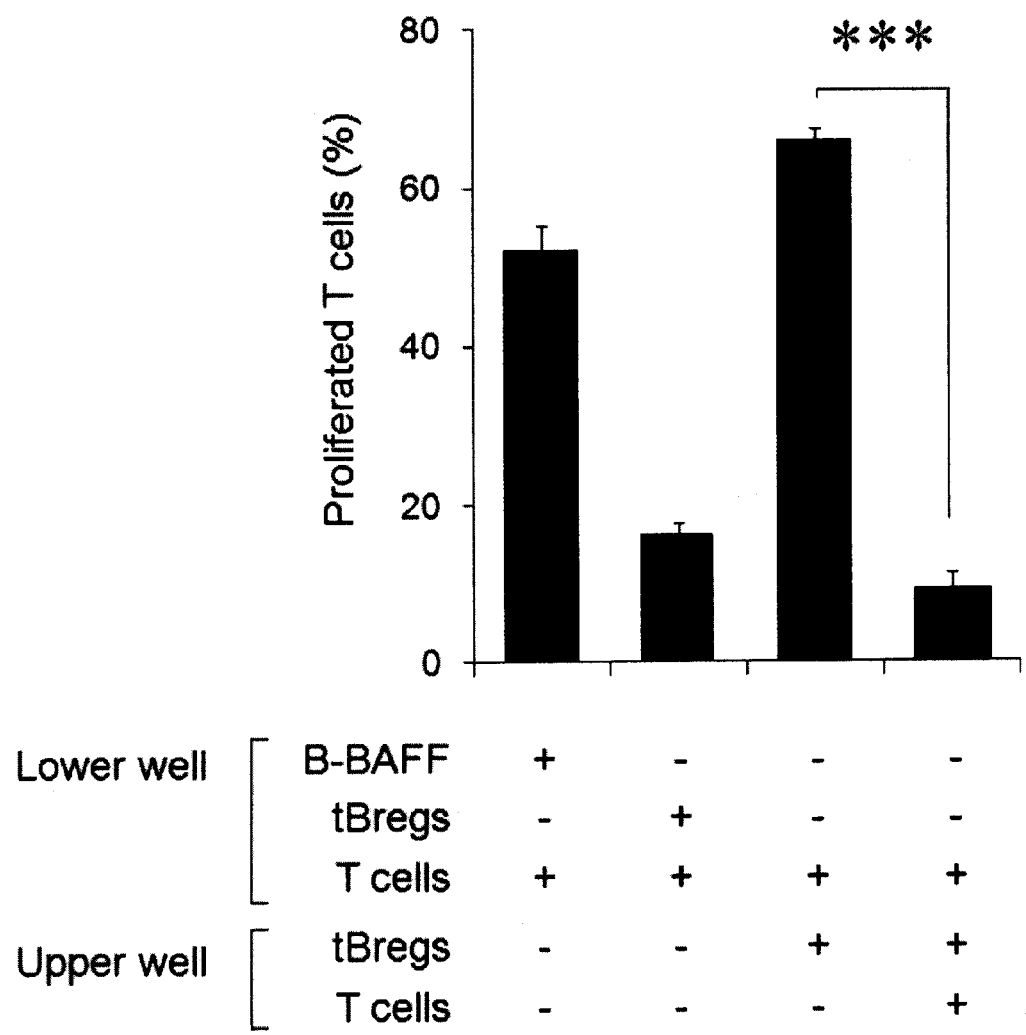

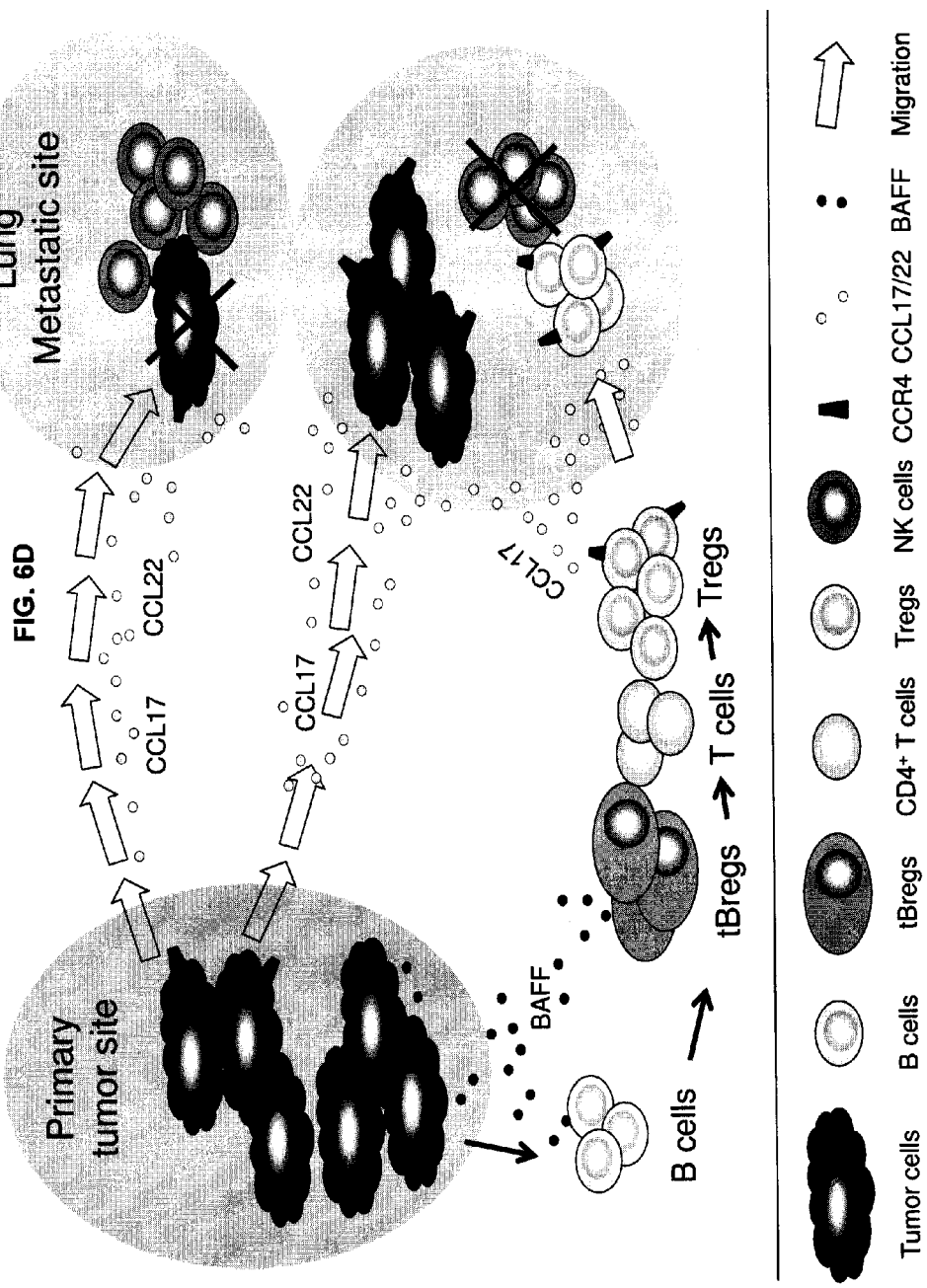

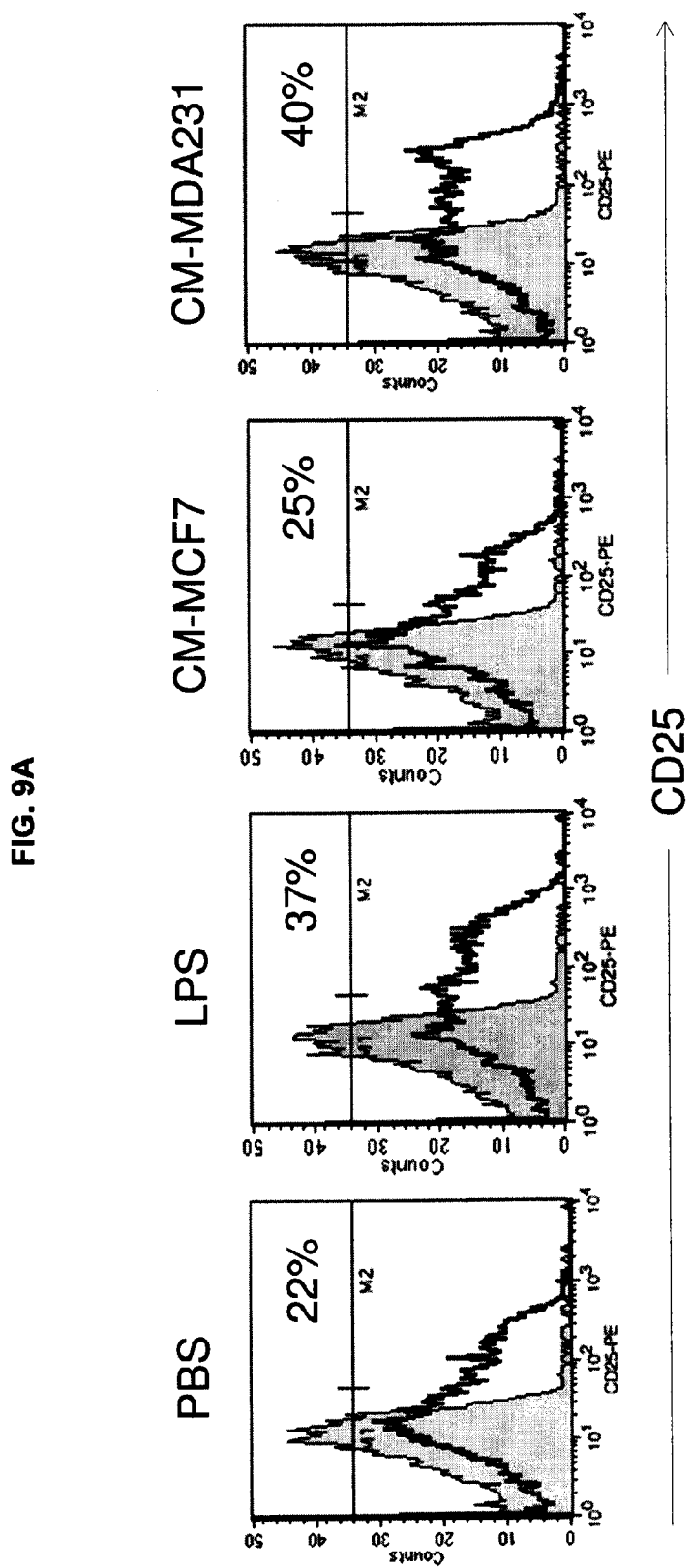

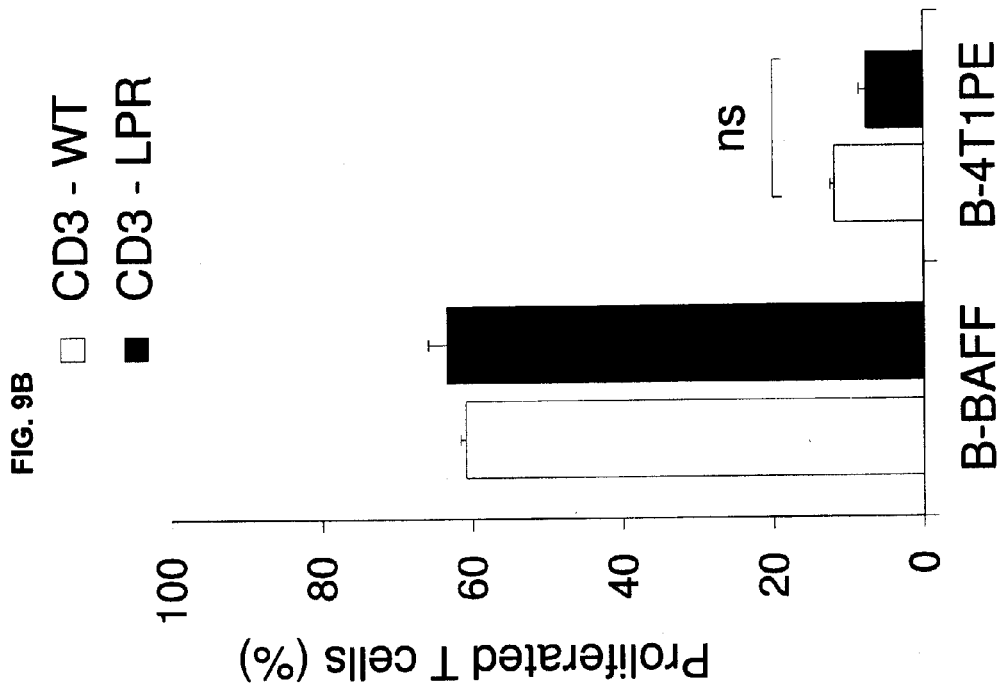

REGULATORY B CELLS (TBREGS) AND THEIR USE

CROSS REFERENCE TO RELATED APPLICATION

This application is the U.S. national stage of PCT Application No. PCT/US2011/023789, filed Feb. 4, 2011, which was published in English under PCT Article 21(2), which claims the benefit of U.S. Provisional Application No. 61/302,074, filed Feb. 5, 2010, which is incorporated by reference herein in its entirety.

FIELD OF THE DISCLOSURE

This relates to the field of immunology, specifically to regulatory B cells and methods for modifying regulatory B cell activity.

BACKGROUND

Cancer escape is an active process that regulates immune responses employing at least two types of suppressive cells, myeloid-derived suppressive cells (Gr1$^+$ CD11b$^+$ MDSCs) and regulatory T cells (Tregs) (Youn et al., J. Immunol. 181, 5791-5802, 2008; Nagaraj and Gabrilovich, Cancer Res. 68, 2561-2563, 2008; Liu et al., J. Immunol. 178, 2883-2892, 2007; Olkhanud et al., Cancer Res. 69, 5996-6004, 2009). For example, cancer cells produce or induce production of GM-CSF, IL-1β, IL-6 and TGFβ to promote generation of Gr1$^+$ MDSCs and M2 macrophages which, in turn, impair antitumor immune responses and promote metastasis (DuPre et al., Int. J. Exp. Pathol. 88, 351-360, 2007; Danna et al., Cancer Res. 64, 2205-2211, 2004; Sinha et al., J. Immunol. 174, 636-645, 2005). This occurs through direct action or indirectly by activating Tregs.

Tregs, as a key subset of CD4$^+$ T cells that control peripheral tolerance to self- and allo-antigens (Sakaguchi et al., J. Immunol. 155, 1151-1164, 1995), represent a group of regulatory T cells expressing CD25 (IL-2Rα), CTL-associated antigen 4 (CTLA-4), scurfin and importantly a fork-head box P3 (FoxP3) gene product (Fontenot et al., Nat. Immunol. 4, 330-336, 2003). They are responsible for direct or indirect inhibition of T cell responses through the suppression of antigen-presenting cells, such as dendritic cells (Serafini et al., Cancer Immunol. Immunother. 53, 64-72, 2004; Huang et al., Cancer Res. 66, 1123-1131, 2006). To do this, they utilize (Fontenot et al., supra 2003; Zheng et al., J. Immunol. 172, 2778-2784, 2004; Cavani et al., J. Invest Dermatol. 114, 295-302, 2000) cell contact-dependent processes involving FasL/Fas and PD1/B7-H1 (Olkhanud et al., supra, 2009; Phares et al., J. Immunol. 182, 5430-5438, 2009; Probst et al., Nat. Immunol. 6, 280-286, 2005), though the use of secreted suppressive factors such as IL-10, TGF-β, IL-27 and IL-35 have also been reported (Groux et al., Nature 389, 737-742, 1997; Annacker et al., J. Immunol. 166, 3008-3018, 2001; Awasthi et al., Nat. Immunol. 8, 1380-1389, 2007; Collison et al., Nature 450, 566-569, 2007). As a result, Tregs are considered to play a key role in the escape of cancer cells from anti-tumor effector T cells (Ishida et al., Clin. Cancer Res. 9, 3625-3634, 2003; Curiel et al., Nat. Med. 10, 942-949, 2004; Woo et al., J. Immunol. 168, 4272-4276, 2002; Beyer et al., Blood. 106, 2018-2025, 2005). In addition, Tregs play an active role in breast cancer lung metastasis by protecting metastasizing cancer cells from NK cells (Olkhanud et al., supra, 2009).

However, a need remains to identify other regulatory immune cells, and to use these cells for the treatment of immune-mediated disease. In addition, a need remains for inhibiting regulatory immune cells that can inhibit immune-mediated therapy, such as for the treatment of cancer.

SUMMARY OF THE DISCLOSURE

Regulatory B cells (tBreg) are disclosed herein. These regulatory B cells express CD25 (CD25$^+$) and also express CD19 (CD19$^+$). These regulatory B cells suppress resting and activated T cells in cell contact-dependent manner. In some embodiments, the tBreg cells can also suppress T cells in a contact independent manner. In some embodiments the tBreg cells express one or more of CD40, CD69, CD80, CD86, B Cell Activating factor receptor (BAFF-R), CC chemokine receptor (CCR)6, CXC chemokine receptor (CXCR)5 and major histocompatibility complex (MHC) molecules. In additional embodiments, the tBreg cells express one or more of thymic stromal lymphoprotein receptor (TSLPR), Fas, FasL and programmed death (PD)-1. In further embodiments, the tBreg cells do not express CD5 and/or CD27. In other embodiments, the tBreg cells express phosphorylated STAT3. In one, non-limiting example, the tBreg cells are pStat3$^+$ CD25$^{High}$B7-H1$^{High}$CD86$^{High}$CCR6$^{High}$ and CD62L$^{Low}$IgM$^{Int/Low}$ B cells. In some embodiments, the tBreg cells induce generation of FoxP3$^+$ regulatory T cells (Tregs) from CD8$^+$ and/or CD4$^+$ T cells. Methods are also disclosed for generating tBregs.

In some embodiments, methods for treating an immune-mediated disorder, such as an autoimmune disease, transplant rejection, graft-versus-host disease or inflammation, are disclosed. These methods include increasing regulatory B cell number or activity and/or by administering autologous regulatory B cells.

In additional embodiments, methods for treating cancer are provided. These methods include decreasing regulatory B cell activity and/or number. The method can include measuring regulatory B cells in a sample from the subject, such as to evaluate the efficacy of therapy.

The foregoing and other features and advantages will become more apparent from the following detailed description of several embodiments, which proceeds with reference to the accompanying figures.

BRIEF DESCRIPTION OF THE FIGURES

FIG. 2A-2E is a set of digital images and graphs. (A) The CM-4T1PE-treated B cells express constitutively active Stat3 (pSat3) and significantly elevated levels of Bcl-xL and p27$^{Kip1}$, while expressions of cyclin D, cyclin E, Rb and Bim are not affected. Shown, results of Western blotting experiments repeated twice. (B) Viability of B cells is enhanced by treatments with BAFF or cancer CM (CM-4T1 and CM-4T1PE), but not PBS (upper panel). Unlike BAFF, only cancer CM treated B cells up-regulate expression of CD25 (lower panel). Shown, the Anexin V/PI staining (to assess viability) and surface expression of CD25 of B cells incubated for indicated days. (C) 4T1 cancer cells are heterogeneous and consist of metastatic (4T1-R3) and non-metastatic (4T1-R4) subsets. Y-axis, number of metastatic foci±SEM in the lungs of BALB/C mice subcutaneously (s.c.) injected with equal numbers of 4T1, 4T1-R3, and 4T1-R4 cells. (D) CM-4T1PE also up regulates expression of BAFF-R (upper panel). Down-regulation of BAFF-R (upper panel) or TACI, but not BCMA, using anti-sense oligonucleotides reduces the survival of B cells cultured in CM-4T1PE (lower panel). Y-axis depicts % of BAFF-R$^+$ cells (upper panel) or % of viable cells after PI staining (lower panel)±SEM of triplicates. (E) ELISA results for the presence of BAFF (pg/ml) in CM-4T1 and CM-4T1PE. All experiments were reproduced at least three times. *P<0.05, P<0.01; *P<0.001.

FIG. 4A-4D is a set of graphs. (A) Human B cells treated with CM of MDA-231 cells (B-MDA-231), but not MCF-7 cells (B-MCF7), or LPS (B-LPS), or PBS (B-PBS), suppress proliferation of T cells. Histograms (A) and graphs (B-D) show % (±SEM of triplicates) of CD3$^+$ T cells that diluted CFSC (proliferated) when mixed with B cells at a 1:1 ratio as in FIG. 3A. (B) Similarly with B-MDA231, B cells treated with CM of other human cancers (depicted on X-axis) also inhibit T cell proliferation. (C) Although tBregs cannot affect proliferation of T cells if the cells are physically separated (placed in the upper and lower chambers of trans-well plate, respectively), tBregs become suppressive if cultured with T cells in upper wells, indicating that tBregs require T cell contact to produce suppressive factors. Controls were B-BAFF and T cells activated with anti-CD3/CD28 Abs (aCD3/CD28). (D) Despite high levels of B7-H1 (FIG. 1D), T cell proliferation was comparably inhibited by w.t. tBregs (grey bars) and B7-H1 deficient tBregs (black bars). All data were repeated at least three times. *P<0.05, P<0.01; *P<0.001.

FIGS. 6A-D are graphs and a schematic diagram. tBregs support Treg-dependent lung metastasis in T and B cell deficient mice via Treg generation. (A) Adoptive transfer of tBregs together with non-Tregs or newly tBreg-generated Tregs (B, depleted of B cells as in FIG. 5B) restores lung metastasis of 4T1.2 tumor cells in T and B cell deficient mice. Control mice received CD25$^-$CD4$^+$ T cells (non-Tregs, A) alone, or tBregs alone (not shown), or T cells cultured with mock-treated B cells (B). Shown, mean lung metastatic foci±SEM of four 4T1.2 cancer-bearing NOD/SCID mice per group experiments reproduced three times. (C) B220$^+$CD25$^+$ tBregs are required for lung metastasis. Mean lung metastatic foci±SEM of four mice per group experiments reproduced three times. 4T1.2 cancer-bearing BALB/C mice were depleted of B220$^+$ and CD25$^+$ cells by i.p. injecting anti-B220 and anti-CD25 Abs alone or together (aCD25+aB220), respectively. Control mice were treated with isotype-matched antibody (control IgG). The data are from four mice per group experiments repeated twice. (D) Summary schema adds a "missing link" that a non-metastatic subsets of breast cancer cells directly induce the generation of tBregs from resting B cells and actively support their survival by producing BAFF. Without being bound by theory, tBregs promote FoxP3$^+$Treg conversion and, thereby, to facilitate lung metastasis. Thus, breast cancer lung metastasis is an active and cancer-controlled process which, on one hand, remotely activates its metastasis site, lungs, to produce CCL17 and CCL22 to recruit CCR4$^+$ subset of cancer cells together with CCR4$^+$ Tregs. The role of Tregs is to protect the metastasizing cancer cells from NK cells by directly killing them. On the other hand, as shown herein, lung metastasis cannot be established in the absence of tBregs, which is needed to induce conversion of Tregs from non-regulatory CD4$^+$ T cells.

FIG. 9A-9G are a set of graphs. (A) CM from human breast cancer cells MCF-7 (CM-MCF7) and MDA-MB-231 (CM-MDA231) induce up regulation of CD25 on purified human peripheral blood B cells. Numbers depict % of $CD25^+CD19^+$ cells. Control B cells were treated with PBS or LPS (10 μg/ml). (B,C) tBregs suppress T cell proliferation independent of Fas-FasL signaling axis. tBregs were generated from w.t. and Fas KO mice (lpr, B) and tested for the suppression of CFSE-labeled T cells from w.t. (B,C) and lpr mice (C). The tBreg-mediated suppression does not involve TGFβ, as neutralizing TGFβ Ab or specific inhibitor of TGF receptor signaling (at indicated doses, μg/ml) failed to abrogate the inhibition (D). tBreg-mediated T cell suppression is not reversed by 1000 U/ml IL-2 (E). Data (mean±SEM of triplicates repeated at least three times) of dividing $CD3^+$ T cells (responder) cultured for four days with equal amounts of B cells. No statistical difference is detected between groups B-MDA231 and B-MDA231+IL-2 (ns). (F) Expression of IL-10 in B cells, as shown by percentage of IL-10 positive cells after intracellular staining of murine B cells (gated on $B220^+CD19^+$ cells, left panel) and secreted amount of IL-10 (pg/ml) in culture medium of human B cells (right panel) after treatment with tumor CM (tBregs or B-MDA231, or LPS or mock treatment (X-axis, as in FIGS. 2,3). *** P<0.001. (G) tBreg-mediated T cell regulation is an IL-10-independent process. tBregs were generated from IL-10 knock-out mice and tested in T cell proliferation assay as in FIG. 1C. No statistical difference is detected between groups wt and KO groups, ns.

DETAILED DESCRIPTION OF SEVERAL EMBODIMENTS

Figure 1A:
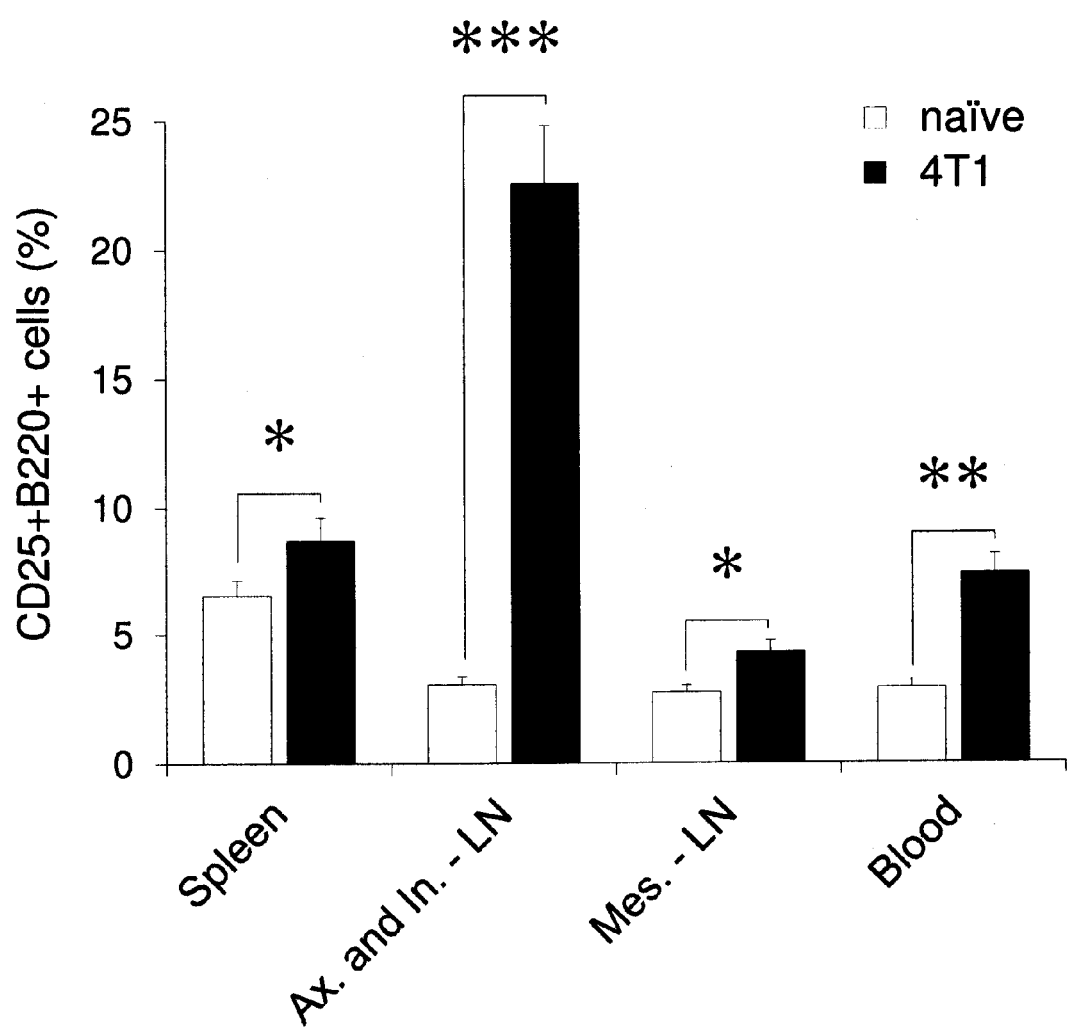
FIGS. 1A-1F are a set of graphs. (A) 4T1 cancer-bearing mice (black bars) have a higher proportion of CD25$^+$B220$^+$ cells (%±SEM of three mice per group) in peripheral blood and secondary lymphoid organs (ax, axillary; In, inguinal; and Mes, mesenteric) compared with naïve BALB/C mice (grey bars). *P<0.05, P<0.01; *P<0.001. (B) CM from non-metastatic 4T1-PE cells (CM-4T1PE) had a greater ability to generate CD25$^+$CD19$^+$B220$^+$ cells in vivo, than CM from metastatic 4T1 cells (CM-4T1). Naïve BALB/C mice were i.p. injected with 0.5 ml CMs (conditioned media) or control medium (Mock) once a day four times and splenocytes were stained for CD25 and B220 cells five days after last treatment. (C) Poorly proliferative CD25$^+$B220$^+$ B cells are generated in vitro from naïve mouse B cells after treatment with CM-4T1PE for two days. Control B cells were treated with LPS (B-LPS), or PBS (B-PBS). Histograms show percentage of proliferated (CFSE-diluted) B cells. Numbers are for % of cells in corresponding quadrants. The results were repeated at least three times. (D, E, F) Surface marker expression (FACS analysis) of purified murine B cells treated with tumor CM (tBregs, pink line), or LPS (B-LPS, red line), or PBS (B-PBS, blue line) after staining with Abs to corresponding surface markers (indicated), or isotype-matched control Ab (grey filled area).

Cancer escape is an active process that regulates immune responses employing at least two types of suppressive cells, myeloid-derived suppressive cells (MDSCs) and regulatory T cells (Tregs) (Youn et al., J. Immunol. 2008; 181:5791-802; Nagarag et al., Cancer Res. 2008; 68:2561-3; Liu et al., J. Immunol. 2007; 178:2883-92; Olkhanud et al., Cancer Res. 2009; 69:5996-6004). For example, cancer cells produce or induce production of GM-CSF, IL-1β, IL-6 and TGFβ to promote generation of $Gr1^+MDSCs$ and M2 macrophages to thereby impair antitumor immune responses through direct action or indirectly by activating Tregs (DuPre et al, Int. J. Exp. Pathol. 2007; 88:351-60; Danna et al, Cancer Res. 2004; 64:2205-11; Sinha et al., J. Immunol. 2005; 174:636-45). Tregs are key subsets of $CD4^+$ T cells that control peripheral tolerance to self- and allo-antigens (Sakaguchi et al., J. Immunol. 1995; 155:1151-64), and the majority of them phenotypically can be identified by the expression of CD25 (IL-2Rα) and a fork-head box P3 (FoxP3) gene product (Fontenot et al., NatImmunol. 2003; 4:330-6). They suppress T cell responses by acting directly or through the inhibition of APCs involving cell contact-, FasL/Fas—and programmed death (PD)1/B7-H1-dependent processes (Olkhanud et al., Cancer Res. 2009; 69:5996-6004; Okudaira et al., Int. J. Oncol. 2009; 35:741-9), or secreted factors such as interleukin (IL)-10, transforming growth factor (TGF)-13, IL-27 and IL-35 (see, for example, Annacker et al., J. Immunol. 2001; 166:3008-18). However, the role of other immune cells, in particular B cells, in cancer escape and metastasis was uncertain prior to the present application. Furthermore, the exact population of B cells that are regulatory in subjects with an autoimmune disease previously was not identified.

Disclosed herein is a novel population of regulatory B cells (tBreg). The regulatory B cells express CD25 ($CD25^+$) and can express a pan B cell marker such as B220 ($B220^+$ in mice), and also express CD19 ($CD19^+$). These regulatory B cells suppress resting and activated T cells in a cell contact-dependent manner. These cells can be from any mammal, including, but not limited to, humans and mice. Methods for generating these regulatory B cells in vitro are also disclosed herein, as are methods for using these regulatory B cells to produce regulatory T cells.

Methods for treating an immune-mediated disorder, such as an autoimmune disease, transplant rejection, graft-versus-host disease or inflammation, by increasing regulatory B cell number or activity and/or by administering autologous regulatory B cells are also disclosed. Methods for treating cancer that include decreasing regulatory B cell activity and/or number are also disclosed.

Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

Allogeneic and Autologous: Organisms, cells, tissues, organs, and the like from, or derived from, individuals of the same species, but wherein the organisms, cells, tissues, organs, and the like are genetically different one from another are "allogeneic." Organisms, cells, tissues, organs, and the like from, or derived from, a single individual, or from a genetically identical individual are "autologous." Transplant rejection" refers to a partial or complete destruction of a transplanted cell, tissue, organ, or the like on or in a recipient of said transplant due to an immune response to an allogeneic graft.

Animal: Living multi-cellular vertebrate organisms, a category that includes, for example, mammals and birds. The term mammal includes both human and non-human mammals. Similarly, the term "subject" includes both human and veterinary subjects.

Antagonist of CD25: An agent that specifically bind to the CD25 component of IL-2R, or a component thereof, and/or inhibits a biological function of the IL-2 receptor or this component of the IL-2R. Functions that can be inhibited are the binding of IL-2 to the IL-2R, the intracellular transmission of a signal from binding of IL-2, antigen presentation by dendritic cells, and proliferation and/or activation of lymphocytes such as T cells in response to IL-2. In one embodiment, IL-2R antagonists of use in the methods disclosed herein inhibit at least one of these functions, can inhibit more than one of these function, or can inhibit or all of these functions.

In one example, an IL-2 receptor antagonist is an antibody that specifically binds Tac (p55), such as ZENAPAX® (see below). Other anti-p55 agents include the chimeric antibody basiliximab (SIMULECT®), BT563 (see Baan et al., *Transplant. Proc.* 33:224-2246, 2001), and 7G8. Basiliximab has been reported to be beneficial in preventing allograft rejection (Kahan et al., *Transplantation* 67:276-84, 1999), and treating psoriasis (Owen & Harrison, *Clin. Exp. Dermatol.* 25:195-7, 2000). An exemplary human anti-p55 antibody of use in the methods of the invention is HUMAX-TAC®, being developed by Genmab. In another example, an IL-2 receptor antagonist is an antibody that specifically binds the p75 or β subunit of the IL-2R.

Additional antibodies that specifically bind the IL-2 receptor are known in the art. For example, see U.S. Pat. No. 5,011,684; U.S. Pat. No. 5,152,980; U.S. Pat. No. 5,336,489; U.S. Pat. No. 5,510,105; U.S. Pat. No. 5,571,507; U.S. Pat. No. 5,587,162; U.S. Pat. No. 5,607,675; U.S. Pat. No. 5,674,494; U.S. Pat. No. 5,916,559. The mik-β1 antibody is an antagonist that specifically binds the beta chain of human IL-2R.

In another example, an IL-2 receptor antagonist is a peptide antagonist that is not an antibody. Peptide antagonists of the IL-2 receptor, including antagonists of Tac (p55) and p75 (IL-2Rβ) are also known. For example, peptide antagonists for p55 and p75 are disclosed in U.S. Pat. No. 5,635,597. Nonpeptidic inhibitors include acylphenyalanine derivatives (see Emerson et al., Protein Science 12: 811-82 (2003), herein incorporated by reference). These peptides, which include apa-II-2 and analogs thereof with an IC50 value of 20 to 70 µM, are also of use in the methods disclosed herein. In a further example, an IL-2 receptor antagonist is a chemical compound or small molecule that specifically binds to the IL-2 receptor and inhibits a biological function of the receptor.

Autoimmune Disease: A disease in which the immune system produces an immune response (for example, a B-cell or a T-cell response) against an antigen that is part of the normal host (that is, an autoantigen), with consequent injury to tissues. An autoantigen may be derived from a host cell, or may be derived from a commensal organism such as the micro-organisms (known as commensal organisms) that normally colonize mucosal surfaces.

Exemplary autoimmune diseases affecting mammals include rheumatoid arthritis, juvenile oligoarthritis, collagen-induced arthritis, adjuvant-induced arthritis, Sjogren's syndrome, multiple sclerosis, experimental autoimmune encephalomyelitis, inflammatory bowel disease (for example, Crohn's disease, ulcerative colitis), autoimmune gastric atrophy, pemphigus vulgaris, psoriasis, vitiligo, type 1 diabetes, non-obese diabetes, myasthenia gravis, Grave's disease, Hashimoto's thyroiditis, sclerosing cholangitis, sclerosing sialadenitis, systemic lupus erythematosis, autoimmune thrombocytopenia purpura, Goodpasture's syndrome, Addison's disease, systemic sclerosis, polymyositis, dermatomyositis, autoimmune hemolytic anemia, pernicious anemia, and the like.

B Cell: A lymphocyte, a type of white blood cell (leukocyte), that develops into a plasma cell (a "mature B cell"), which produces antibodies. An "immature B cell" is a cell that can develop into a mature B cell. Generally, pro-B cells (that express, for example, CD45 or B220) undergo immunoglobulin heavy chain rearrangement to become pro B pre B cells, and further undergo immunoglobulin light chain rearrangement to become an immature B cells. Immature B cells include T1 and T2 B cells. Thus, one example of an immature B cell is a T1 B that is an AA41$^{hi}$CD23$^{lo}$ cell. Another example of an immature B cell is a T2 B that is an AA41$^{hi}$CD23$^{hi}$ cell. Thus, immature B cells include B220 expressing cells wherein the light and the heavy chain immunoglobulin genes are rearranged, and that express AA41. Immature B cells can develop into mature B cells, which can produce immunoglobulins (e.g., IgA, IgG or IgM). Mature B cells express characteristic markers such as CD21 and CD23 (CD23$^{hi}$CD21$^{hi}$ cells), but do not express AA41. B cells can be activated by agents such as lippopolysaccharide (LPS) or IL-4 and antibodies to IgM.

A "regulatory B cell" (tBreg) is a B cell that suppress resting and activated T cells in cell contact-dependent manner that expresses CD25 and CD19. Additional tBreg matters are disclosed herein.

B Cell Activating Factor Receptor (BAFFR): The receptor specific for B Cell Activating Factor (BAFF) also known as BLysS. BAFF is a 285-amino acid long peptide glycoprotein which undergoes glycosylation at residue 124. It is expressed as transmembrane protein on various cell types including monocytes, dendritic cells and bone marrow stromal cells. The transmembrane form can be cleaved from the membrane, generating a soluble protein fragment. BAFF is the natural ligand of BAFF-R, which is primarily expressed on mature B lymphoctyes in vivo. BAFFR is also known as Tumor necrosis factor receptor super family (TNFRSF) member 13C. Exemplary amino acid sequences for BAFFR are set for in UNIPROT Accession No. Q96RJ3 (human) and UNIPROT Accession No. Q9D8D0, which are incorporated by reference herein.

CD: Cluster of Differentiation. This is a nomenclature system for antigens found on lymphocytes, although CD antigens can be found on cells other than lymphocytes. This is nomenclature used to name antigens recognized by monoclonal antibodies that specifically bind an antigen on B cells. Each numeric antigen is a specific protein that is recognized in the art by its CD designation.

CC Chemokine Receptor 6 (CCR6): A macrophage inflammatory protein (MIP)-3 alpha receptor expressed by immature dendritic cells and memory T cells in vivo. CCR6 belongs to family A of the G protein-coupled receptor superfamily. This receptor is also called CD196. The amino acid sequence for human CCR6 is set forth as UNIPROT No. P51684 and GENBANK® Accession No. NP_004358.2, and the amino acid sequence for mouse CCR6 is set forth as UNIPROT No. Q3U467 and GENBANK® Accession No. NP_033965, all of which are incorporated herein by reference.

CD4: A glycoprotein expressed on the surface of T helper cells, regulatory T cells, monocytes, macrophages, and dendritic cells. It was originally known as leu-3 and T4 (after the OKT4 monoclonal antibody). It has four immunoglobulin domains ($D_1$ to $D_4$) that are exposed on the extracellular surface of the cell, see ENTREZ No. 920, UNIPROT No. P01730, and GENBANK® Accession No. NP_000607, which are incorporated by reference. A CD4+ T lymphocyte is an immune cell that expresses this marker on its surface. Many of these cells are helper T cells, which help orchestrate the immune response, including antibody responses as well as killer T cell responses.

CD8: A transmembrane glycoprotein that serves as a co-receptor for the T cell receptor (TCR). Like the TCR, CD8 binds to a major histocompatibility complex (MHC) molecule, but is specific for the class I MHC protein, see ENTREZ No. 925 and UNIPROT No. P01732, which are incorporated by reference herein. In one embodiment, a CD8+ T cell is a cytotoxic T lymphocyte. In another embodiment, a CD8+ cell is a suppressor T cell.

CD19: An antigen also known as B4, Leu12 or MGC12802, which is expressed on B cells. Exemplary amino acid sequences for CD19 are provided in GENBANK® Accession Nos. AAI36395.1 (human), AAH90937.1 (human), AAA37388.1 (mouse), and NP_001013255.2 (rat), which are all incorporated by reference herein.

CD20: An antigen also called human B-lymphocyte-restricted differentiation antigen or Bp35 that is a hydrophobic transmembrane protein with a molecular weight of approximately 35 kD located on pre-B and mature B lymphocytes (Valentine et al., *J. Biol. Chem.* 264(19):11282-11287, 1989; and Einfield et al., EMBO J. 7(3):711-717, 1988). In vivo, CD20 is found on the surface of greater than 90% of B cells from peripheral blood or lymphoid organs and is expressed during early pre-B cell development and remains expressed until plasma cell differentiation. CD20 is present on both normal B cells and malignant B cells, but is not found on hematopoietic stem cells, pro-B cells, normal plasma cells, or other normal tissues (Tedder et al., *J. Immunol.* 135(2):973-979, 1985).

CD20 is involved in regulating early steps in the activation and differentiation process of B cells (Tedder et al., *Eur. J. Immunol.* 16:881-887, 1986) and can function as a calcium ion channel (Tedder et al., *J. Cell. Biochem.* 14D:195, 1990). Exemplary amino acid sequences for CD19 are provided in GENBANK® Accession Nos. NP_068769.2 (human), NP_690605.1 (human), and NP_031667.1 (mouse), which are incorporated by reference herein.

CD21: A cell surface antigen found on B cells that is also known as B2, that is identical to complement receptor 2 (CR2), which binds C3d. CD21 is the major receptor for C3d fragments in immune complexes. Exemplary amino acid sequences for CD19 are provided in GENBANK® Accession Nos. CAA66910.1 (human) AAG37227.1 (human), NP_031784.1 (mouse), which are incorporated by reference herein.

CD23: A cell surface antigen that is a 45 kDa protein expressed on B and T cells following antigen activation and is an IgE low affinity receptor. The nucleotide sequence of the cDNA predicts a polypeptide with 321 amino acids and a molecular mass of 36.3 kDa. The CD23 gene maps to human chromosome 19p13.3. Constitutive expression of CD23 is a characteristic feature of many EBV-transformed B-lymphoblasts. Exemplary amino acid sequences for CD23 are provided in GENBANK® Accession Nos. AAL84004.1 (rat), AAH14108.1 (human), NP_001993.2 (human), and NP_038545.1 (mouse), which are all incorporated herein by reference.

CD25: An antigen also known as Tac or p55. CD25 is the alpha chain of the IL-2 receptor. In vivo, CD25 has a length of 251 amino acids with an extracellular domain of 219 amino acids and a very short cytoplasmic domain of 13 amino acids. The p55 gene maps to human chromosome 10p14-p15. The expression of p55 is regulated by a nuclear protein called RPT-1. Exemplary amino acid sequences for CD25 are provided in GENBANK® Accession Nos. CAA44297.1 (rat), NP_000408.1 (human), NP_001003211.1 (dog), and NP_032393 (mouse), which are all incorporated herein by reference.

CD40: A cell surface antigen also known as Bp50 and TNFRSF5, which shares homology with the TNF receptor superfamily. The human CD40 gene maps to chromosome 20. CD40 is a transmembrane glycoprotein with a length of 277 amino acids (48 kDa) and is a receptor for CD40 ligand. CD40 is a phosphoprotein and can be expressed as a homodimer. A soluble form of CD40 (28 kDa) has been described. CD40 has a short cytoplasmic domain with limited homology to the conserved cytosolic death domain of the tumor necrosis factor (TNF) R1 receptor and APO-1. CD40 protein is expressed on all B-lymphocytes during various stages of development, activated T-cells and monocytes, follicular dendritic cells, thymic epithelial cells, and various carcinoma cell lines. Exemplary amino acid sequences for CD40 are provided in GENBANK® Accession Nos. AAB08705.1 (mouse), CAM26470.1 (mouse), AAH12419.1 (human), and ABM82730.1 (synthetic), which are all incorporated herein by reference.

CD62: A selectin. Specifically, CD62P is P-selectin, which is a 140 kd protein found on endothelial cells and activated platelets in vivo. Exemplary amino acid sequences for CD62 are provided in GENBANK® Accession Nos. AAA09834.1 (CD62P, mouse), AAH68533.1 (CD62P, human), and AAN06828.1 (CD62P, human), which are incorporated herein by reference.

CD69: An antigen that is expressed after cell activation in T cells, and that is expressed on B cells, natural killer cells, platelets, thymocytes and Langerhans cells in vivo. CD69 is also known as C-type lectin. Exemplary amino acid sequences for CD69 are provided in GENBANK® Accession Nos. CAA80298.1 (human), NP_001772.1 (human, ADK94898.1 (rat), and NP_001028294.1 (mouse) which are all incorporated herein by reference.

CD80: A protein found on activated B cells (and monocytes) that provides a costimulatory signal necessary for T cell activation and survival. It is the ligand for two different proteins on the T cell surface: CD28 (for autoregulation and intercellular association) and CTLA-4. CD80 functions with CD86 in T cell priming. Exemplary amino acid sequences for CD80 are provided in GENBANK® Accession Nos. AAC02262.1 (rat), NP_033985.3 (mouse), and NP_005182.1 (human), which are all incorporated herein by reference.

CD81: A transmembrane protein and belongs to the tetraspanin superfamily, in which all of the members possess four transmembrane domains, aminoterminal and carboxyterminal cytoplasmic domains, and two extracellular loops. It is expressed by human T cells at all stages of development. Cross-linking of CD81 with antibodies has been shown to provide a costimulatory signal with CD3 on human thymocytes, T-cell lines, and naive mouse T-cells. Exemplary amino acid sequences for CD81 are provided in GEN- BANK® Accession Nos. NP_037219.1 (rat), NP_598416.1 (mouse), and NP_004347.1 (human), which are all incorporated herein by reference.

CXC Chemokine Receptor (CXCR)5: A G-protein coupled seven transmembrane receptor, also known as Burkitt lymphoma receptor 1, that is the receptor for chemokine CXCL13, also known as BLC. This receptor plays a role in B cell migration. CXCR5 is also known as CD185. Exemplary sequences for CXCR5 are disclosed in GENBANK® Accession No. NP_001707 (human) and XP_996425 (mouse), which are all incorporated by reference herein.

Chemotherapy; chemotherapeutic agents: As used herein, any chemical agent with therapeutic usefulness in the treatment of diseases characterized by abnormal cell growth. Such diseases include tumors, neoplasms, and cancer as well as diseases characterized by hyperplastic growth such as psoriasis. In one embodiment, a chemotherapeutic agent is an agent of use in treating neoplasms such as solid tumors. In one embodiment, a chemotherapeutic agent is a radioactive molecule. One of skill in the art can readily identify a chemotherapeutic agent of use (e.g. see Slapak and Kufe, *Principles of Cancer Therapy*, Chapter 86 in Harrison's Principles of Internal Medicine, 14th edition; Perry et al., *Chemotherapy*, Ch. 17 in Abeloff, Clinical Oncology $2^{nd}$ ed., © 2000 Churchill Livingstone, Inc; Baltzer L, Berkery R (eds): Oncology Pocket Guide to Chemotherapy, 2nd ed. St. Louis, Mosby-Year Book, 1995; Fischer D S, Knobf M F, Durivage H J (eds): The Cancer Chemotherapy Handbook, 4th ed. St. Louis, Mosby-Year Book, 1993).

Contacting or contact: A spatial relationship between two items, such as cells, provided for a time and under condition such that a reciprocal or non reciprocal action or influence between the two items can be exerted. In particular, a direct contact and/or interaction between two cells or can result in a modification of one of the cells following a direct action of the other cell as a result of the physical interaction. In one non-limiting example, incubation of Treg cells with a tBreg cells can be performed in vitro by mixing a cell culture comprising T cells with a cell culture comprising the tBreg cells, such that direct contact occurs.

Epitope: The site on an antigen recognized by an antibody as determined by the specificity of the amino acid sequence. Two antibodies are said to bind to the same epitope if each competitively inhibits (blocks) binding of the other to the antigen as measured in a competitive binding assay (see, e.g., Junghans et al., *Cancer Res.* 50:1495-1502, 1990). Alternatively, two antibodies have the same epitope if most amino acid mutations in the antigen that reduce or eliminate binding of one antibody reduce or eliminate binding of the other. Two antibodies are said to have overlapping epitopes if each partially inhibits binding of the other to the antigen, and/or if some amino acid mutations that reduce or eliminate binding of one antibody reduce or eliminate binding of the other.

Fas and FasL: Fas is a death receptor on the surface of cells that leads to programmed cell death by one of two apoptosis pathways. FasR is also known as CD95, Apo-1, and tumor necrosis factor receptor superfamily, member 6 (TNFRSf6). FasR is located on chromosome 10 in humans and 19 in mice, see also ENTREZ No. 355, UNIPROT No. P25445 and GENBANK® No. NP_000034, which are all incorporated herein by reference. Fas ligand (FasL) is a type-II transmembrane protein that belongs to the tumor necrosis factor (TNF) family. Binding of FasL to Fas induces apoptosis. Exemplary sequence of FasL can be found at GENBANK® Accession No. NP_000630, ENTREZ No. 356 and UNIPROT No. P48023, which are all incorporated herein by reference.

FOXP3: A transcription factor also known as "$FKH^{sf}$" or "scurfin." Exemplary nucleic acids encoding FOXP3, and exemplary amino acids sequences of FOXP3 polypeptide are disclosed in published PCT Application No. 02/090600 A2, which is incorporated herein by reference. The FOXP3 transcription factor is predominately expressed by Treg cells. FOXP3 is a regulator of cytokine production and cell to cell contact dependent inhibition of T effector cell activation. Mutations in FOXP3 have been shown to be involved in scurfy mice and in humans with IPEX (Immunodysregulation, Polyendocrinopathy, and Enteropathy, X-linked). FOXP3 expression confers suppressive function to peripheral $CD4^+CD25^+$ Treg cells.

Graft-Versus-Host Disease (GVHD): A common and serious complication of bone marrow or other tissue transplantation wherein there is a reaction of donated immunologically competent lymphocytes against a transplant recipient's own tissue. GVHD is a possible complication of any transplant that uses or contains stem cells from either a related or an unrelated donor.

There are two kinds of GVHD, acute and chronic. Acute GVHD appears within the first three months following transplantation. Signs of acute GVHD include a reddish skin rash on the hands and feet that may spread and become more severe, with peeling or blistering skin. Acute GVHD can also affect the stomach and intestines, in which case cramping, nausea, and diarrhea are present. Yellowing of the skin and eyes (jaundice) indicates that acute GVHD has affected the liver. Chronic GVHD is ranked based on its severity: stage/grade 1 is mild; stage/grade 4 is severe. Chronic GVHD develops three months or later following transplantation. The symptoms of chronic GVHD are similar to those of acute GVHD, but in addition, chronic GVHD may also affect the mucous glands in the eyes, salivary glands in the mouth, and glands that lubricate the stomach lining and intestines.

Immune-Mediated Disorder: A disorder in which the immune response plays a key role in the development or progression of the disease. Immune-mediated disorders include autoimmune disorders, allograft rejection, graft versus host disease and inflammatory conditions.

Immune response: A response of a cell of the immune system, such as a B cell, or a T cell, to a stimulus. In one embodiment, the response is specific for a particular antigen (an "antigen-specific response").

A "parameter of an immune response" is any particular measurable aspect of an immune response, including, but not limited to, cytokine secretion (IL-6, IL-10, IFN-γ, etc.), immunoglobulin production, dendritic cell maturation, and proliferation of a cell of the immune system. One of skill in the art can readily determine an increase in any one of these parameters, using known laboratory assays. In one specific non-limiting example, to assess cell proliferation, incorporation of $^3$H-thymidine can be assessed. A "substantial" increase in a parameter of the immune response is a significant increase in this parameter as compared to a control. Specific, non-limiting examples of a substantial increase are at least about a 50% increase, at least about a 75% increase, at least about a 90% increase, at least about a 100% increase, at least about a 200% increase, at least about a 300% increase, and at least about a 500% increase. Similarly, an inhibition or decrease in a parameter of the immune response is a significant decrease in this parameter as compared to a control. Specific, non-limiting examples of a substantial decrease are at least about a 50% decrease, at least about a 75% decrease, at least about a 90% decrease, at least about a 100% decrease, at least about a 200% decrease, at least about a 300% decrease, and at least about a 500% decrease. A statistical test, such as a non-paramentric ANOVA, can be used to compare differences in the magnitude of the response induced by one agent as compared to the percent of samples that respond using a second agent. In some examples, p≤0.05 is significant, and indicates a substantial increase or decrease in the parameter of the immune response. One of skill in the art can readily identify other statistical assays of use. Immunoglobulin: A protein including one or more polypeptides substantially encoded by immunoglobulin genes. The recognized immunoglobulin genes include the kappa, lambda, alpha (IgA), gamma ($IgG_1$, $IgG_2$, $IgG_3$, $IgG_4$), delta (IgD), epsilon (IgE) and mu (IgM) constant region genes, as well as the myriad immunoglobulin variable region genes. Full-length immunoglobulin light chains are generally about 25 Kd or 214 amino acids in length. Full-length immunoglobulin heavy chains are generally about 50 Kd or 446 amino acid in length. Light chains are encoded by a variable region gene at the NH2-terminus (about 110 amino acids in length) and a kappa or lambda constant region gene at the COOH-terminus. Heavy chains are similarly encoded by a variable region gene (about 116 amino acids in length) and one of the other constant region genes.

The basic structural unit of an antibody is generally a tetramer that consists of two identical pairs of immunoglobulin chains, each pair having one light and one heavy chain. In each pair, the light and heavy chain variable regions bind to an antigen, and the constant regions mediate effector functions. Immunoglobulins also exist in a variety of other forms including, for example, Fv, Fab, and (Fab')$_2$, as well as bifunctional hybrid antibodies and single chains (e.g., Lanzavecchia et al., *Eur. J. Immunol.* 17:105, 1987; Huston et al., *Proc. Natl. Acad. Sci. U.S.A.*, 85:5879-5883, 1988; Bird et al., *Science* 242:423-426, 1988; Hood et al., *Immunology, Benjamin, N.Y.*, 2nd ed., 1984; Hunkapiller and Hood, *Nature* 323:15-16, 1986).

An immunoglobulin light or heavy chain variable region includes a framework region interrupted by three hypervariable regions, also called complementarity determining regions (CDR's) (see, *Sequences of Proteins of Immunological Interest*, E. Kabat et al., U.S. Department of Health and Human Services, 1983). As noted above, the CDRs are primarily responsible for binding to an epitope of an antigen.

Chimeric antibodies are antibodies whose light and heavy chain genes have been constructed, typically by genetic engineering, from immunoglobulin variable and constant region genes belonging to different species. For example, the variable segments of the genes from a mouse monoclonal antibody can be joined to human constant segments, such as kappa and gamma 1 or gamma 3. In one example, a therapeutic chimeric antibody is thus a hybrid protein composed of the variable or antigen-binding domain from a mouse antibody and the constant or effector domain from a human antibody (e.g., ATCC Accession No. CRL 9688 secretes an anti-Tac chimeric antibody), although other mammalian species can be used, or the variable region can be produced by molecular techniques. Methods of making chimeric antibodies are well known in the art, e.g., see U.S. Pat. No. 5,807,715, which is herein incorporated by reference.

A "humanized" immunoglobulin is an immunoglobulin including a human framework region and one or more CDRs from a non-human (such as a mouse, rat, or synthetic) immunoglobulin. The non-human immunoglobulin providing the CDRs is termed a "donor" and the human immunoglobulin providing the framework is termed an "acceptor." In one embodiment, all the CDRs are from the donor immunoglobulin in a humanized immunoglobulin. Constant regions need not be present, but if they are, they must be substantially identical to human immunoglobulin constant regions, i.e., at least about 85-90%, such as about 95% or more identical. Hence, all parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. Exemplary conservative substitutions are those such as gly, ala; val, ile, leu; asp, glu; asn, gln; ser, thr; lys, arg; and phe, tyr (see U.S. Pat. No. 5,585,089, which is incorporated herein by reference). Humanized immunoglobulins can be constructed by means of genetic engineering, e.g., see U.S. Pat. No. 5,225,539 and U.S. Pat. No. 5,585,089, which are herein incorporated by reference.

A human antibody is an antibody wherein the light and heavy chain genes are of human origin. Human antibodies can be generated using methods known in the art. Human antibodies can be produced by immortalizing a human B cell secreting the antibody of interest. Immortalization can be accomplished, for example, by EBV infection or by fusing a human B cell with a myeloma or hybridoma cell to produce a trioma cell. Human antibodies can also be produced by phage display methods (see, e.g., Dower et al., PCT Publication No. WO91/17271; McCafferty et al., PCT Publication No. WO92/001047; and Winter, PCT Publication No. WO92/20791, which are herein incorporated by reference), or selected from a human combinatorial monoclonal antibody library (see the Morphosys website). Human antibodies can also be prepared by using transgenic animals carrying a human immunoglobulin gene (e.g., see Lonberg et al., PCT Publication No. WO93/12227; and Kucherlapati, PCT Publication No. WO91/10741, which are herein incorporated by reference).

Interleukin-2 (IL-2) receptor: A cellular receptor that binds IL-2 and mediates its biological effects. Three different types of IL-2 receptors are distinguished that are expressed differentially and independently. The high affinity IL-2 receptor ($K_d$~10 µM) constitutes approximately 10% of all IL-2 receptors expressed by cells. This receptor is a membrane receptor complex consisting of the two subunits: IL-2R-alpha (also known as T cell activation (TAC) antigen or p55) and IL-2R-beta (also known as p75 or CD122). An intermediate affinity IL-2 receptor ($K_d$=100 µM) consists of the p75 subunit and a gamma chain, while a low affinity receptor ($K_d$=10 nM) is formed by p55 alone.

p75 is 525 amino acids in length. It has an extracellular domain of 214 amino acids and a cytoplasmic domain of 286 amino acids. The p75 gene maps to human chromosome 22q11.2-q12, contains 10 exons and has a length of approximately 24 kb. p55 is 251 amino acids in length with an extracellular domain of 219 amino acids and a very short cytoplasmic domain of 13 amino acids. The gene encoding p55 maps to human chromosome 10p14-p15.

p75 is expressed constitutively on resting T-lymphocytes, NK cells, and a number of other cell types while the expression of p55 is usually observed only after activation. Activated lymphocytes continuously secrete a 42 kDa fragment of p55 (TAC antigen). This fragment circulates in the serum and plasma and functions as a soluble IL2 receptor (see Smith, *Ann. Rev. Cell Biol.* 5:397-425, 1989; Taniguchi and Minami, Cell 73:5-8, 1993).

p55 (also known as CD25, see above) has a length of 251 amino acids with an extracellular domain of 219 amino acids and a very short cytoplasmic domain of 13 amino acids. The p55 gene maps to human chromosome 10p14-p15. The expression of p55 is regulated by a nuclear protein called RPT-1.

A third 64 kDa subunit of the IL2 receptor, designated gamma, has been described. This subunit is required for the generation of high and intermediate affinity IL-2 receptors but does not bind IL-2 by itself. The gene encoding the gamma subunit of the IL2 receptor maps to human chromosome Xq13, spans approximately 4.2 kb and contains eight exons.

Isolated: An "isolated" biological component (such as a nucleic acid, peptide or protein) has been substantially separated, produced apart from, or purified away from other biological components in the cell of the organism in which the component naturally occurs, i.e., other chromosomal and extrachromosomal DNA and RNA, and proteins. Nucleic acids, peptides and proteins which have been "isolated" thus include nucleic acids and proteins purified by standard purification methods. The term also embraces nucleic acids, peptides and proteins prepared by recombinant expression in a host cell as well as chemically synthesized nucleic acids. Similarly, an "isolated" cell has been substantially separated, produced apart from, or purified away from other cells of the organism in which the cell naturally occurs. Isolated cells can be, for example, at least 99%, at least 98%, at least 95%, at least 90%, at least 85%, or at least 80% pure.

Janus Activated Kinase (JAK)/Signal Transducer and Activator of Transcription (STAT): JAKs are cytoplasmic tyrosine kinases that are either constitutively associated with cytokine receptors or recruited to receptors after ligand binding. In either case, stimulation with the ligand results in the catalytic activation of receptor-associated JAKs. This activation results in the phosphorylation of cellular substrates, including the JAK-associated cytokine receptor chains. Some of these phosphorylated tyrosines can serve as coding sites for STAT proteins, which bind to the phosphotyrosines by their SRC-homology 2 (SH2) domains. STAT proteins are also phosphorylated on a conserved tyrosine residue (tyrosine 705 in STAT3), resulting in their dimerization and acquisition of high-affinity DNA-binding activity, which facilitates their action as nuclear transcription factors.

STAT3 is a major cell signaling constituent with roles in both survival and differentiation. However, STAT3 can be phosphorylated on two major residues, Tyrosine (Tyr)705 and Serine (Ser)727. Tyr705 phosphorylation is mediated by JAK2 and Src kinases. Ser727 phosphorylation is mediated by ERK, JNK kinases, TAK1-NLK kinases, and mTOR. Akt and mTOR are also known to mediate survival and growth in many cell types.

The JAK/STAT pathway is one of the most rapid cytoplasmic to nuclear signaling mechanisms. There are a total of four JAK (JAK1-3 and tyrosine kinase 2) and seven STAT proteins (STAT1-4, STAT5A, STAT5b and STATE). JAKs are relatively large cytoplasmic kinases of about 1,100 amino acids in length, and range in size from about 116 kDa to about 140 kDa. The STAT proteins can dimerize, translocate to the nucleus, and bind DNA. Binding of the STAT proteins to the DNA can result in the activation of transcription (for review see Leonard, *Nature Reviews* 1: 200-208, 2001). Exemplary amino acid sequences of STAT3 can be found, for example, as GENBANK® Accession Nos. NP_644805 (Unigene, see also GENBANK® No. A54444, Jul. 28, 2000), NP_003141 (Sep. 3, 2006), NP_998825 (Aug. 25, 2006), NP_998824 (Aug. 24, 2006), AAH00627 (Jul. 15, 2006), AAH87025 (Jul. 16, 2006), CAA62920 (Apr. 8, 2005), which are all incorporated herein by reference.

Leukocyte: Cells in the blood, also termed "white cells," that are involved in defending the body against infective organisms and foreign substances. Leukocytes are produced in the bone marrow. There are 5 main types of white blood cell, subdivided between 2 main groups: polymorphomnuclear leukocytes (neutrophils, eosinophils, basophils) and mononuclear leukocytes (monocytes and lymphocytes).

Mammal: This term includes both human and non-human mammals. Similarly, the term "subject" includes both human and veterinary subjects.

Major Histocompatibility Complex (MHC) class I: MHC class I molecules are formed from two non-covalently associated proteins, the α chain and β2-microglobulin. The α chain comprises three distinct domains, α1, α2 and α3. The three-dimensional structure of the α1 and α2 domains forms the groove into which antigen fits for presentation to T-cells. The α3 domain is an Ig-fold like domain that contains a transmembrane sequence that anchors the α chain into the cell membrane of the APC. MHC class I complexes, when associated with antigen (and in the presence of appropriate co-stimulatory signals) stimulate CD8 cytotoxic T-cells, which function to kill any cell which they specifically recognize.

MHC Class II: MHC class II molecules are formed from two non-covalently associated proteins, the α chain and the β chain. The α chain comprises α1 and α2 domains, and the β chain comprises β1 and β2 domains. The cleft into which the antigen fits is formed by the interaction of the α1 and β1 domains. The α2 and β2 domains are transmembrane Ig-fold like domains that anchor the α and β chains into the cell membrane of the APC. MHC class II complexes, when associated with antigen (and in the presence of appropriate co-stimulatory signals) stimulate CD4 T-cells. The primary functions of CD4 T-cells are to initiate the inflammatory response, to regulate other cells in the immune system, and to provide help to B cells for antibody synthesis. MHC Class II includes, but is not limited to, HLA-DR (either A or B), an HLA-DP (A and B), or an HLA-DQ (A and B).

Polypeptide: A polymer in which the monomers are amino acid residues that are joined together through amide bonds. When the amino acids are alpha-amino acids, either the L-optical isomer or the D-optical isomer can be used, the L-isomers being preferred. The terms "polypeptide" or "protein" as used herein is intended to encompass any amino acid sequence and include modified sequences such as glycoproteins. The term "polypeptide" is specifically intended to cover naturally occurring proteins, as well as those that are recombinantly or synthetically produced.

The term "fragment" refers to a portion of a polypeptide that is at least 8, 10, 15, 20 or 25 amino acids in length. The term "functional fragments of a polypeptide" refers to all fragments of a polypeptide that retain an activity of the polypeptide (e.g., the binding of an antigen). Biologically functional fragments, for example, can vary in size from a polypeptide fragment as small as an epitope capable of binding an antibody molecule to a large polypeptide capable of participating in the characteristic induction or programming of phenotypic changes within a cell. The term "soluble" refers to a form of a polypeptide that is not inserted into a cell membrane.

Polynucleotide: A nucleic acid sequence (such as a linear sequence) of any length. Therefore, a polynucleotide includes oligonucleotides, and also gene sequences found in chromosomes. An "oligonucleotide" is a plurality of joined nucleotides joined by native phosphodiester bonds. An oligonucleotide is a polynucleotide of between 6 and 300 nucleotides in length. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide. Functional analogs of naturally occurring polynucleotides can bind to RNA or DNA, and include peptide nucleic acid (PNA) molecules.

Pharmaceutical agent or drug: A chemical compound or composition capable of inducing a desired therapeutic or prophylactic effect when properly administered to a subject. Pharmaceutical agents include, but are not limited to, chemotherapeutic agents and anti-infective agents.

Pharmaceutically acceptable carriers: The pharmaceutically acceptable carriers useful in this invention are conventional. *Remington's Pharmaceutical Sciences*, by E. W. Martin, Mack Publishing Co., Easton, Pa., 15th Edition (1975), describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Preventing or treating a disease: "Preventing" a disease refers to inhibiting the full development of a disease, for example in a person who is known to have a predisposition to a disease such as an immune-mediated disorder, such as an autoimmune disease. An example of a person with a known predisposition is someone with a history of an autoimmune disorder (such as multiple sclerosis) in the family, or who has been exposed to factors that predispose the subject to a condition. "Treatment" refers to a therapeutic intervention that ameliorates a sign or symptom of a disease or pathological condition after it has begun to develop.

Programmed Death (PD)-1: A protein that forms a complex with PD-L1 or PD-L2 protein and is involved in an immune response, such as the co-stimulation of T cells. Generally, PD-1 protein are substantially identical to the naturally occurring (wild type) PD-1 (see, for example, Ishida et al. EMBO J. 11:3887-3895, 1992, Shinohara et al. Genomics 23:704-706, 1994; and U.S. Pat. No. 5,698,520, all incorporated by reference herein in their entirety). In several examples, PD-1 signaling reduces, for example, CD8+ T cell cytoxicity by reducing T cell proliferation, cytokine production, or viral clearance. Exemplary amino acid sequences for PD-1 are provided in GENBANK® Accession Nos. NP_054862.1 (human), NP_068693.1 (mouse) and NP_001178883.1 (rat), which are incorporated herein by reference.

Purified: The term purified does not require absolute purity; rather, it is intended as a relative term. Thus, for example, a purified peptide preparation is one in which the peptide or protein is more enriched than the peptide or protein is in its natural environment within a cell. Preferably, a preparation is purified such that the protein or peptide represents at least 50% of the total peptide or protein content of the preparation. In another example, a purified cell preparation is one in which the cell type of interest is significantly more enriched than the cell is in its natural environment within a cell. Preferably, a preparation is purified such that the cell represents at least 50% of the total cell content of the preparation.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques. Similarly, a recombinant protein is one encoded by a recombinant nucleic acid molecule.

Specific binding agent: An agent that binds substantially only to a defined target. Thus a CD20-specific binding agent binds substantially only to CD20, or a component thereof, and do not significantly bind to other molecules.

Antibodies may be produced using standard procedures described in a number of texts, including Harlow and Lane (*Using Antibodies, A Laboratory Manual*, CSHL, New York, 1999, ISBN 0-87969-544-7). In addition, certain techniques may enhance the production of neutralizing antibodies (U.S. Pat. No. 5,843,454; U.S. Pat. No. 5,695,927; U.S. Pat. No. 5,643,756; and U.S. Pat. No. 5,013,548). The determination that a particular agent binds substantially only to CD20 may readily be made by using or adapting routine procedures. One suitable in vitro assay makes use of the Western blotting procedure (described in many standard texts, including Harlow and Lane, 1999). Western blotting may be used to determine that a given protein binding agent, such as an anti-CD20 monoclonal antibody, binds substantially only to CD20. Antibodies to CD20 are well known in the art.

Shorter fragments of antibodies can also serve as specific binding agents. For instance, Fabs, Fvs, and single-chain Fvs (scFvs) that bind to an antigen of interest are specific binding agents.

Symptom and sign: A "symptom" is any subjective evidence of disease or of a subject's condition, i.e., such evidence as perceived by the subject; a noticeable change in a subject's condition indicative of some bodily or mental state. A "sign" is any abnormality indicative of disease, discoverable on examination or assessment of a subject. A sign is generally an objective indication of disease. Signs include, but are not limited to any measurable parameters such as tests for immunological status or the presence of lesions in a subject.

T Cell: A white blood cell critical to the immune response. T cells include, but are not limited to, $CD4^+$ T cells and $CD8^+$ T cells. A $CD4^+$ T lymphocyte is an immune cell that carries a marker on its surface known as cluster of differentiation 4 (CD4). These cells, classically known as helper T cells (Th cells), help orchestrate the immune response, including antibody responses as well as killer T cell responses. $CD8^+$ T cells carry the cluster of differentiation 8 (CD8) marker. In one embodiment, CD8 T cells are cytotoxic T lymphocytes (Tc cells) which are capable of lysing target cells by direct cell contact. These cells play a role in the elimination of virus-infected cells and tumor cells, and are involved in transplant rejection processes. In another embodiment, a CD8 cell is a suppressor T cell. Mature T cells express CD3.

Regulatory T cells (Treg) suppress immune responses of other cells. In one example, a regulatory T cell is $CD4^+CD25^+$ that suppresses an immune response. In additional examples, a regulatory T cell expresses CD4, CD25 and FOXP3.

Therapeutically effective dose: A dose sufficient to prevent advancement, or to cause regression of the disease, or which is capable of relieving symptoms caused by the disease, such as, but not limited to, pain or swelling.

Thymic stromal lymphoprotein receptor (TSLPR): The receptor for thymic stromal lymphoprotein (TSLP), which is a cytokine that plays a role in T cell maturation. TSLP signals through a heterodimeric receptor that includes TSLPR and the alpha chain of the IL-7 receptor. Exemplary sequences for TSLPR are disclosed in GENBANK® Accession No. AAL90454.1 (rat), AAF82189.1 (mouse), and AAK60618.1 (human) which are all incorporated by reference herein.

Tumor: An abnormal growth of cells, which can be benign or malignant. Cancer is a malignant tumor, which is characterized by abnormal or uncontrolled cell growth. Other features often associated with malignancy include metastasis, interference with the normal functioning of neighboring cells, release of cytokines or other secretory products at abnormal levels and suppression or aggravation of inflammatory or immunological response, invasion of surrounding or distant tissues or organs, such as lymph nodes, etc. "Metastatic disease" refers to cancer cells that have left the original tumor site and migrate to other parts of the body for example via the bloodstream or lymph system.

The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant." Examples of hematological tumors include leukemias, including acute leukemias (such as 11q23-positive acute leukemia, acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Examples of solid tumors, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer (including basal breast carcinoma, ductal carcinoma and lobular breast carcinoma), lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, and central nervous system (CNS) tumors (such as a glioma, astrocytoma, medulloblastoma, craniopharyrgioma, ependymoma, pinealoma, hemangioblastoma, acoustic neuroma, oligodendroglioma, meningioma, melanoma, neuroblastoma and retinoblastoma).

Tumor antigens (TAs): An antigen expressed on a tumor which can stimulate tumor-specific T-cell-defined immune responses. Exemplary TAs include, but are not limited to, RAGE-1, tyrosinase, MAGE-1, MAGE-2, NY-ESO-1, Melan-A/MART-1, glycoprotein (gp) 75, gp100, beta-catenin, PRAME, MUM-1, WT-1, CEA, and PR-1. Additional TAs are known in the art (for example see Novellino et al., *Cancer Immunol. Immunother.* 2004 Aug. 7 [Epub ahead of print]) and includes TAAs not yet identified.

ZENAPAX® (daclizumab): A particular recombinant, humanized monoclonal antibody of the human IgG1 isotype that specifically binds Tac (p55). The recombinant genes encoding ZENAPAX® are a composite of human (about 90%) and murine (about 10%) antibody sequences. The donor murine anti-Tac antibody is an IgG2a monoclonal antibody that specifically binds the IL-2R Tac protein and inhibits IL-2-mediated biologic responses of lymphoid cells. The murine anti-Tac antibody was "humanized" by combining the complementarity-determining regions and other selected residues of the murine anti-TAC antibody with the framework and constant regions of the human IgG1 antibody. The humanized anti-Tac antibody daclizumab is described and its sequence is set forth in U.S. Pat. No. 5,530,101, see SEQ ID NO: 5 and SEQ ID NO: 7 for the heavy and light chain variable regions respectively. U.S. Pat. No. 5,530,101 and Queen et al., *Proc. Natl. Acad. Sci.* 86:1029-1033, 1989 are both incorporated by reference herein in their entirety. Daclizumab inhibits IL-2-dependent antigen-induced T cell proliferation and the mixed lymphocyte response (MLR) (Junghans et al., *Cancer Research* 50:1495-1502, 1990), as can other antibodies of use in the methods disclosed herein.

All accession numbers, such as GENBANK®, UNIPROT, or ENTREZ Accession numbers, that provide amino acid or nucleic acid sequences are incorporated herein as of the filing date of the present application unless otherwise indicated. Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Regulatory B Cells (tBreg) and their Production

Isolated regulatory B cells (tBreg) are disclosed herein. These regulatory B cells (tBreg) express CD25, and CD19 (CD25$^+$CD19$^+$) and suppress T cells in cell contact-dependent manner. In some embodiments, the tBreg cells also suppress T cells in a contact independent manner. In additional embodiments, the tBreg cells express CD21 and CD23, and/or express high levels of CD81.

In some embodiment the tBreg cells express one or more of CD40, CD69, CD80, CD86, BAFF-R, CCR6, CXCR5 and MHC molecules. Thus, the tBreg cells can express two, three, four, five, six or all seven of CD40, CD69, CD80, CD86, BAFF-R, CCR6, and CXCR5. The tBreg cells can also express MHC molecules, such as MHC class I or MHC class II. In additional embodiments, the tBreg cells express one or more of TSLPR, Fas, FasL and programmed death (PD)-1. Thus, the tBreg cells can express one, two, three or all four of TSLPR, Fas, FasL and PD-1. In further embodiments, the tBreg cells do not express CD5 and/or CD27. In other embodiments, the tBreg cells express phosphorylated STAT3. In one, non-limiting example, the tBreg cells are pStat3$^+$ CD25$^{High}$B7-H1$^{High}$CD86$^{High}$CCR6$^{High}$ and CD62L$^{Low}$IgM$^{Int/Low}$ B cells.

In some embodiments, the tBreg cells induce generation of FoxP3$^+$ regulatory T cells (Tregs) from CD8$^+$ and/or CD4$^+$ T cells. In additional embodiments, the tBreg cells promote regulatory T cell (Treg)-dependent metastasis when introduced into a T cell deficient host.

Methods for the isolation and quantitation of populations of cells are well known in the art, and the isolation and quantitation of tBreg cells, such as regulatory CD25$^+$CD19$^+$ B ells can be accomplished by any means known to one of skill in the art. Fluorescence activated cell sorting (FACS), or other cell isolation methods, including but not limited to panning and separation using magnetic beads, can be used to isolate and/or identify B cells that are CD25$^+$CD19$^+$. Similarly, these methods can be used to isolate and/or identify B cells that express one or more of CD40, CD69, CD80, CD81, CD86, BAFF-R, CCR6, CXCR5, MHC molecules, TSLPR, Fas, FasL and PD-1, or any combination of these markers. These methods can also be used to isolate and/or identify populations of B cells that do not express CD5 and/or CD27. In one, non-limiting example, the tBreg cells are pStat3$^+$ CD25$^{High}$B7-H1$^{High}$CD86$^{High}$CCR6$^{High}$ and CD62L$^{Low}$IgM$^{Int/Low}$ B cells. The cells are any type of mammalian cells, including but not limited to, human or murine cells.

In one embodiment, labeled antibodies specifically directed to one or more cell surface markers are used to identify and quantify tBreg cells and populations of these cells that express additional markers. The antibodies can be conjugated to other compounds including, but not limited to, enzymes, magnetic beads, colloidal magnetic beads, haptens, fluorochromes, metal compounds, radioactive compounds or drugs. The enzymes that can be conjugated to the antibodies include, but are not limited to, alkaline phosphatase, peroxidase, urease and B-galactosidase. The fluorochromes that can be conjugated to the antibodies include, but are not limited to, fluorescein isothiocyanate, tetramethylrhodamine isothiocyanate, phycoerythrin, allophycocyanins and Texas Red. For additional fluorochromes that can be conjugated to antibodies see Haugland, R. P., *Handbook of Fluorescent Probes and Research Products*, published by Molecular Probes, 9$^{th}$ Edition (2002). The metal compounds that can be conjugated to the antibodies include, but are not limited to, ferritin, colloidal gold, and particularly, colloidal superparamagnetic beads. The haptens that can be conjugated to the antibodies include, but are not limited to, biotin, digoxigenin, oxazalone, and nitrophenol. The radioactive compounds that can be conjugated or incorporated into the antibodies are known to the art, and include, but are not limited to, technetium 99 ($^{99}$Tc), $^{125}$I, and amino acids comprising any radionuclides, including, but not limited to, $^{14}$C, $^3$H and $^{35}$S.

In some examples, CD25$^+$ CD19$^+$ tBreg cells, or CD25$^+$ CD19$^+$ tBreg cells that express one or more additional markers (for example, CD21, CD23, CD40, CD69, CD80, CD81, CD83, CD86, BAFF-R, CCR6, CXCR5, MHC molecules, TSLPR, Fas, FasL and/or PD-1), are isolated by contacting the cells with an appropriately labeled antibody. However, other techniques of differing efficacy may be employed to purify and isolate desired populations of cells. The separation techniques employed should maximize the retention of viability of the fraction of the cells to be collected. The particular technique employed will, of course, depend upon the efficiency of separation, cytotoxicity of the method, the ease and speed of separation, and what equipment and/or technical skill is required.

Additional separation procedures may include magnetic separation, using antibody-coated magnetic beads, affinity chromatography, cytotoxic agents, either joined to a monoclonal antibody or used in conjunction with complement, and "panning," which utilizes a monoclonal antibody attached to a solid matrix, or another convenient technique. Antibodies attached to magnetic beads and other solid matrices, such as agarose beads, polystyrene beads, hollow fiber membranes and plastic Petri dishes, allow for direct separation. Cells that are bound by the antibody can be removed from the cell suspension by simply physically separating the solid support from the cell suspension. The exact conditions and duration of incubation of the cells with the solid phase-linked antibodies will depend upon several factors specific to the system employed. The selection of appropriate conditions, however, is well known in the art.

Unbound cells then can be eluted or washed away with physiologic buffer after sufficient time has been allowed for the cells expressing a marker of interest (such as, but not limited to, CD19, CD21, CD23, CD25, CD40, CD69, CD80, CD81, CD83, CD86, BAFF-R, CCR6, CXCR5, MHC molecules, TSLPR, Fas, FasL and PD-1) to bind to the solid-phase linked antibodies. The bound cells are then separated from the solid phase by any appropriate method, depending mainly upon the nature of the solid phase and the antibody employed, and quantified using methods well known in the art. In one specific, non-limiting example, bound cells separated from the solid phase are quantified by FACS.

Antibodies may be conjugated to biotin, which then can be removed with avidin or streptavidin bound to a support, or fluorochromes, which can be used with FACS to enable cell separation and quantitation, as known in the art.

In another embodiment, an apheresis procedure employing an automated apheresis instrument (such as the CS-3000 blood cell separator, Baxter Health Care, Deerfield, Ill., or equivalent machine) can be used to collect cells from a subject. In a specific, non-limiting example, labeled antibodies specifically directed to one or more cell surface markers are used to identify and quantify the CD25$^+$ CD19$^+$ tBreg cells, such as the cells described above.

In other embodiments, the tBreg cells express phosphorylated STAT3. Methods are known in the art to evaluate the phosphorylation status of STAT3 (see, for example, PCT Publication No. WO 2009/026106 and WO 2007/030693, incorporated herein by reference). In non-limiting examples, to evaluate the phosphorylation status of STAT3, Western blot technology is used with the cell proteins separated by electrophoresis and antibodies that bind to STAT3, STAT3 phosphorylated at serine 727, and/or antibodies that specifically bind the STAT3 phosphorylated at tyrosine 705 are utilized. Alternatively, the cells may be incubated in the presence of orthophosphate containing a radiolabeled phosphorus, permitting the detection of phosphorylated or unphosphorylated substrate (such as phosphorylated STAT3, or STAT3 phosphorylated specifically at serine 727).

In some embodiments, tBreg cells are washed with Ca$^{2+}$ and Mg$^{2+}$ free PBS and total protein is extracted as described (Haldar et al., *Cell Death Diff* 1:109-115, 1994; Haldar et al., *Nature* 342:195-198, 1989; Haldar et al., *Cancer Res.* 54:2095-2097, 1994). Phosphorylation is analyzed using Western blotting and immunodetection which are performed using Amersham ECL, an enhanced chemiluminescence detection system and well known methodology. In one example, phosphorylation of stem cells or precursor cells can be carried out in phosphate free media (GIBCO) using 1 mCi/ml [$P^{32}$] orthophosphoric acid (NEN) for six hours in the presence of a test compound. Immunoprecipitation of $P^{32}$ labeled cellular extract can be performed, for example, as described in Haldar et al., Nature 342:195-198, 1998. Generally, immunoprecipitation utilizes an antibody that binds a substrate of interest, such as STAT3 phosphorylated at serine 727 or STAT3 phosphorylated at serine 705. An immunocomplex is run on a 0.75 mm thick 10% SDS-PAGE. Subsequently, gels are dried and exposed for autoradiography.

Phospho-amino acid analysis can be performed using other methods known in the art. For example, the analysis can be performed essentially as described in the manual for the Hunter thin layer electrophoresis system, HTLE700, (CBS Scientific Company Inc., USA). Briefly, $P^{32}$ labeled immunoprecipitates are run on 10% SDS-PAGE gels. The immunoreactive bands of interest are cut out of the gel and eluted with 50 μM ammonium bicarbonate. After elution, the proteins are precipitated in the presence of 15%-20% TCA plus carrier protein, and washed with ethanol. Precipitated protein is then oxidized in performic acid and lyophilized. The dried pellet is resuspended in constant boiling HCl, heated at 110° C. and lyophilized. The residue is resuspended in pH 1.9 buffer (50 μl formic acid, 156 μl acetic acid, 1794 mcl $H_2O$) containing phospho-amino acid standards and spotted on a PEI cellulose plate. Two-dimensional thin layer chromatography is run using the pH 1.9 buffer for the first dimension and pH 3.5 buffer (100 ml acetic acid, 10 ml pyridine, 1890 ml $H_2O$) for the second. The plate is baked at 65° C. for 10 minutes, and the cold standards are visualized by spraying the plate with 0.25% ninhydrin and returning the plate to the 65° C. oven for 15 minutes. The plate is then exposed to film, such as to Kodak X-omat AR film, such as for two to four weeks.

$CD25^+CD19^+$ tBreg cells prevent the activation and/or expansion of other cells of the immune system. Therefore, in one embodiment, the $CD25^+$ $CD19^+$ tBreg cells are immunosuppressive cells. In some embodiments, the tBreg cells regulate T cells in a contact independent manner. For example, the tBreg cells can regulate Treg cells in a contact dependent manner. Exemplary methods to evaluate this regulation are provided in the examples section below.

In one specific, non-limiting example, the tBreg also regulate T cells in a contact independent manner, such as by expressing interleukin (IL)-10. Production of IL-10 by the cells can be assessed by assaying for IL-10 in the cell culture supernatant. The ability of the cells to produce IL-10 also can be assessed by measuring IL-10 production in naive cells and in cultured cells stimulated with LPS (lipopolysaccharide), PMA (phorbol 12-myristate 13-acetate), ionomycin, CpG or comparable stimulatory Toll-like receptor agonists, or with an agonist of CD40 (e.g., using an antibody to CD40). In addition, production of IL-10 can be verified directly by intracellular cytokine staining or by Enzyme-linked immunosorbent spot (ELISPOT). Standard immunoassays known in the art can be used for such purpose (see PCT Publication No. 2009/131712, which is incorporated herein by reference).

Suitable conditions for performing the contacting or incubation are identifiable by a skilled person and comprise providing a suitable environment for cell culture in vitro or suitable environment for e.g. by use of a robotic incubator which controls and monitors the temperature and optionally also the atmospheric $CO_2$, $N_2$ and/or $O_2$ content, relative humidity, nutrient amounts and other conditions suitable to provide the cells with a suitable growth environment. Also additional procedures and techniques suitable for performing contacting between cells in vitro or in vivo can be identified by a skilled person upon reading of the present disclosure. The time frame of incubation can be determined by one of skill in the art experimentally in view of the specific T cells, B cells, related suitable conditions and the experimental design.

An isolated tBreg population can include at least 90%, at least 91%, at least 92%, at least 93%, at least 94%, at least 95%, at least 99%, or 100% tBreg cells. Thus, an isolated population of tBreg cells can include at least 90%, at least 91%, at least 92%, at least 93%, at least 94%, at least 95%, at least 99%, or 100% tBreg cells such as ($CD25^+CD19^+$ cells that suppress T cells in cell contact-dependent manner). In one embodiment, the tBreg cells in the isolated population suppress T cells in a contact independent manner. In additional embodiments, the tBreg cells in the isolated population express CD21 and CD23, and/or express high levels of CD81. In a further embodiment, the tBreg cells in the isolated population express one or more of CD40, CD69, CD80, CD86, BAFF-R, CCR6, CXCR5 and MHC molecules. Thus, in some examples, the tBreg cells in the isolated population express two, three, four, five, six or all seven of CD40, CD69, CD80, CD86, BAFF-R, CCR6, and CXCR5. In other embodiments, the tBreg cells in the isolated population express MHC molecules, such as MHC class I or MHC class II. In additional embodiments, the tBreg cells in the population express one or more of TSLPR, Fas, FasL and programmed death (PD)-1. Thus, in additional embodiments, the tBreg cells in the population express one, two, three or all four of TSLPR, Fas, FasL and PD-1. In further embodiments, the tBreg cells in the population do not express CD5 and/or CD27. In other embodiments, the tBreg cells in the population express phosphorylated STAT3. In one, non-limiting example, the isolated population of tBreg cells are pStat3$^+$ $CD25^{High}B7-H1^{High}CD86^{High}CCR6^{High}$ and $CD62L^{Low}IgM^{Int/Low}$ B cells.

The data generated by flow-cytometers can be plotted in a single dimension, to produce a histogram, or in two-dimensional dot plots or even in three dimensions. The regions on these plots can be sequentially separated, based on fluorescence intensity, by creating a series of subset extractions, termed "gates." Specific gating protocols are known in the art. The plots are generally made on logarithmic scales. Because different fluorescent dyes' emission spectra overlap, signals at the detectors are compensated electronically and computationally. Data accumulated using the flow cytometer can be analyzed using software such as FLOWJO® or CELLQUEST PRO®. The analysis is most often done on a separate computer. The principles of gating, which allow the identification of cells that express high or low levels of a protein of interest, are well known in the art. Tutorials for learning to establish gates are provided, for example, and the INVITROGEN® website. Generally, one of skill in the art can readily use any FACS machine and computer programs for data analysis to establish gates to separate cells that express a particular marker. As an example, one of skill in the art can readily identify cells wherein expression of CD25 is absent ($CD25^-$), expression of CD25 is present ($CD25^+$), expression of CD25 is present and low ($CD25^{low}$), and expression of CD25 is present and high ($CD25^{high}$). Similarly, one can use FACS analysis and a computer program to identify cells wherein expression of CD81 is absent ($CD81^-$), expression of CD81 is present ($CD81^+$), expression of CD81 is present and low ($CD81^{low}$), and expression of CD81 is present and high ($CD81^{high}$). The terms "low" and "high" are standard in the art and are can be determined for a specific cell population using standard techniques including FACS, computer programs and gating.

Methods are also provided herein for generating populations of tBreg cells in vitro. These methods include contacting a sample comprising B cells in vitro with media conditioned by a tumor cell, and isolating tBreg cells. The B cells can be isolated from a subject, including a human or a veterinary subject.

The production of conditioned media (CM) is known in the art. In one embodiment, conditioned media is produced by collecting cell culture media from a tumor cell culture, such as a breast cancer cell culture, wherein the cancer cells are cultured in the media for a specified period of time. For example, the tumor cells can be cultured in the media for about 12, about 24, about 36, about 48 or about 72 hours at 37° C. The medium can be collected from any type of tumor cell culture, including but not limited to sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer (including basal breast carcinoma, ductal carcinoma and lobular breast carcinoma), lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, and CNS tumors. Generally, the media is any tissue culture media that is used for the in vitro culture of cells. Non-limiting examples include Dulbecco's Modified Eagle Medium (DMEM) and RPMI1640. Following culture in the conditioned medium, tBreg cells are isolated from the culture.

Exemplary non-limiting methods for generating tBregs are provided in the Examples section below.

Method for Inducing Immunosuppression in a Subject

A method is also disclosed herein for inducing immunosuppression in a subject, such as for treating an immune-mediated disorder. The method includes administering to the subject a therapeutically effective amount of tBreg cells, such as CD25$^+$CD19$^+$ regulatory B cells, such as any of the tBreg cells described above, thereby treating the immune-mediated disorder in the subject. In some embodiments, the tBreg cells are autologous. In other embodiments, the tBreg cells are heterologous. The subject can be any subject of interest, including human and veterinary subjects.

In one embodiment, the subject has an autoimmune disease. Examples of an autoimmune disease include, but are not limited to, multiple sclerosis, rheumatoid arthritis, systemic lupus erythematosis, type I diabetes mellitus, Crohn's disease; myasthenia gravis, Grave's disease, Hashimoto's thyroiditis, ankylosing spondylitis, or psoriasis. In another embodiment, the subject has graft-versus-host disease (GVHD).

In yet another embodiment the subject is the recipient of a transplanted organ. Examples of a transplanted organ include kidney, liver, skin, or heart. Regulatory B cells, such as immunosuppressive CD25$^+$CD19$^+$ tBreg cells, can be administered prior to transplantation, concurrently with transplantation, or following transplantation. In one specific, non-limiting example, administration of the therapeutically effective amount of regulatory B cells occurs 3-5 days prior to transplantation. In other embodiments, the subject has graft versus host disease.

In a further embodiment, administration of a therapeutically effective amount of tBreg B cells to a subject treats or inhibits inflammation in the subject. Thus, the method includes administering a therapeutically effective amount of tBreg cells to the subject to inhibit the inflammatory process. In a specific, non-limiting example, the tBreg are CD25$^+$CD19$^+$ cells, such as any of the tBreg cells described herein. The method can also include administering a therapeutically effective amount of regulatory T cells.

Effective treatment can be measured by many methods known to those of skill in the art. For example, neutrophil infiltration at a site of inflammation can be measured. In order to assess neutrophil infiltration myeloperoxidase activity can be measured. Myeloperoxidase is a hemoprotein present in azurophilic granules of polymorphonuclear leukocytes and monocytes. It catalyzes the oxidation of halide ions to their respective hypohalous acids, which are used for microbial killing by phagocytic cells. Thus, a decrease in myeloperoxidase activity in a tissue reflects decreased neutrophil infiltration, and can serve as a measure of inhibition of inflammation.

In another example, effective treatment can be assayed by measuring cytokine levels in the subject. Cytokine levels in body fluids or cell samples are determined by conventional methods. For example, an immunospot assay, such as the enzyme-linked immunospot or "ELISPOT" assay, can be used. The immunospot assay is a highly sensitive and quantitative assay for detecting cytokine secretion at the single cell level. Immunospot methods and applications are well known in the art and are described, for example, in Czerkinsky et al., *J. Immunol. Methods* 110:29-36, 1988; Olsson et al. *J. Clin. Invest.* 86:981-985, 1990; and EP 957359. Variations of the standard immunospot assay are well known in the art and can be used to detect alterations in cytokine production in the methods of the disclosure (see, for example, U.S. Pat. No. 5,939,281 and U.S. Pat. No. 6,218,132).

Antibodies suitable for use in immunospot assays, which are specific for secreted cytokines, as well as detection reagents and automated detection systems, are well known in the art and generally are commercially available. Appropriate detection reagents are also well known in the art and commercially available, and include, for example, secondary antibodies conjugated to fluorochromes, colored beads, and enzymes whose substrates can be converted to colored products (for example, horseradish peroxidase and alkaline phosphatase). Other suitable detection reagents include secondary agents conjugated to ligands (for example, biotin) that can be detected with a tertiary reagent (for example, streptavidin) that is detectably labeled as above.

Other methods for measuring cytokine levels in the subject are well known in the art, and can be used as an alternative to immunospot assays. Such methods include ELISA, which can be used to measure the amount of cytokine secreted by T-cells into a supernatant (see, for example, Vandenbark et al., *Nature Med.* 2:1109-1115, 1996). Alternatively, the expression of cytokine mRNA can be determined by standard immunological methods, which include reverse transcriptase polymerase chain reaction (RT-PCR) and in-situ hybridization.

In another embodiment, administration of a therapeutically effective amount of tBreg cells to a subject induces the production of regulatory T cells, such as CD4$^+$CD25$^+$ suppressive T cells. In further embodiments, administration of a therapeutically effective amount of CD25+ CD19+ regulatory B cells decreases the proliferation of CD4+ and/or CD8+ T cells. Thus, the number of CD4+CD25+, CD4+ and/or CD8+ T cells can be measured following the administration of tBreg cells.

Suppression of proliferation can be evaluated using many methods well known in the art. In one embodiment, cell proliferation is quantified by measuring [$^3$H]-thymidine incorporation. Proliferating cells incorporate the labeled DNA precursor into newly synthesized DNA, such that the amount of incorporation, measured by liquid scintillation counting, is a relative measure of cellular proliferation. In another embodiment, cell proliferation is quantified using the thymidine analogue 5-bromo-2'-deoxyuridine (BrdU) in a proliferation assay. BrdU is incorporated into cellular DNA in a manner similar to thymidine, and is quantified using anti-BrdU mAbs in an ELISA.

In a further embodiment, cell proliferation may be determined based upon the reduction of the tetrazolium salt 3,[4,5-dimethylthiazol-2-yl]-2,5-diphenyltetrazolium bromide (MTT). The tetrazolium ring of MTT is reduced to formazan, which is blue in color, by the succinate-tetrazolium reductase system active only in viable cells. The intensity of the resulting color change indicates the enzymatic activity of living cells. In actively proliferating cells, MTT conversion increases, whereas in senescent and dying cells, the rate of MTT conversion slows. Comparison of this value to an untreated control provides a measure of the change in cellular proliferation.

Immunosuppression can be evaluated using many methods well known in the art. In one embodiment, a white blood cell count (WBC) is used to determine the responsiveness of a subject's immune system. A WBC measures the number of white blood cells in a subject. Using methods well known in the art, the white blood cells in a subject's blood sample are separated from other blood cells and counted. Normal values of white blood cells are about 4,500 to about 10,000 white blood cells/μl. Lower numbers of white blood cells can be indicative of a state of immunosuppression in the subject.

In another embodiment, immunosuppression in a subject may be determined using a T-lymphocyte count. Using methods well known in the art, the white blood cells in a subject's blood sample are separated from other blood cells. T-lymphocytes are differentiated from other white blood cells using standard methods in the art, such as, for example, immunofluoresence or FACS. Reduced numbers of T-cells, or a specific population of T-cells can be used as a measurement of immunosuppression. A reduction in the number of T-cells, or in a specific population of T-cells, compared to the number of T-cells (or the number of cells in the specific population) prior to treatment can be used to indicate that immunosuppression has been induced.

Administration of tBreg cells can be utilized whenever immunosuppression or inhibition of inflammation is desired, for example, at the first sign of symptoms of an autoimmune disease, such as multiple sclerosis, rheumatoid arthritis, systemic lupus erythematosis, type I diabetes mellitus, Crohn's disease; myasthenia gravis, Grave's disease, Hashimoto's thyroiditis, ankylosing spondylitis, or psoriasis, or at the first sign of symptoms of inflammation, such as pain, edema and elevated temperature.

Therapeutically effective amounts of tBreg cells can be administered by a number of routes, including parenteral administration, for example, intravenous, intraperitoneal, intramuscular, intrasternal, or intraarticular injection, or infusion.

The therapeutically effective amount of tBreg will be dependent on the subject being treated, the severity and type of the affliction, and the manner of administration. For example, a therapeutically effective amount of tBreg cells can vary from about $5 \times 10^6$ cells per kg body weight to about $7.5 \times 10^8$ cells per kg body weight, such as about $2 \times 10^7$ cells to about $5 \times 10^8$ cells per kg body weight, or about $5 \times 10^7$ cells to about $2 \times 10^8$ cells per kg body weight. The exact amount of tBreg cells is readily determined by one of skill in the art based on the age, weight, sex, and physiological condition of the subject. Effective doses can be extrapolated from dose-response curves derived from in vitro or animal model test systems.

The therapeutically effective amount of tBreg cells for use in inducing immunosuppression or treating or inhibiting inflammation is that amount that achieves a desired effect in a subject being treated. For instance, this can be the amount of regulatory B cells necessary to inhibit advancement, or to cause regression of an autoimmune disease, or which is capable of relieving symptoms caused by an autoimmune disease, such as pain and inflammation. It can be the amount necessary to relieve symptoms associated with inflammation, such as pain, edema and elevated temperature. It can also be the amount necessary to diminish rejection of a transplanted organ.

The isolated regulatory B cells disclosed herein can be administered in a pharmaceutically acceptable carrier, such as buffered saline or another medium suitable for administration to a subject. The regulatory B cells can be administered in conjunction with other cells, such as regulatory T cells. In one embodiment, compositions containing isolated populations of regulatory B cells can also contain one or more additional pharmaceutical agents, such as one or more anti-microbial agents (for example, antibiotics, anti-viral agents and anti-fungal agents), anti-tumor agents (for example, fluorouracil, methotrexate, paclitaxel, fludarabine, etoposide, doxorubicin, or vincristine), immune-depleting agents (for example, fludarabine, etoposide, doxorubicin, or vincristine), immunosuppressive agents (for example, azathioprine or glucocorticoids, such as dexamethasone or prednisone), anti-inflammatory agents (for example, glucocorticoids such as hydrocortisone, dexamethasone or prednisone, or non-steroidal anti-inflammatory agents such as acetylsalicylic acid, ibuprofen or naproxen sodium), cytokines (for example, interleukin-10 and transforming growth factor-beta), hormones (for example, estrogen), or a vaccine. Such additional pharmaceutical agents can be administered before, during, or after administration of the regulatory B cells, depending on the desired effect. This administration of the cells and the agent can be by the same route or by different routes, and either at the same site or at a different site.

Methods for Treating Tumors

Methods are provided herein for inducing an immune response to a tumor antigen in a subject with a tumor. These methods include decreasing the number of tBreg cells in the subject; and administering the tumor antigen or a nucleic acid encoding the tumor antigen to the subject, thereby inducing an immune response to the tumor antigen in the subject.

Regulatory B cells (tBregs) can be inhibited or killed by delivering toxins and siRNA/miRNA utilizing cell surface receptors expressed by tBregs. In other embodiments, reducing the number of tBreg cells in the subject comprises administering to the subject a therapeutically effective amount of an antibody that specifically binds CD25 or CD19, and optionally an antibody that specifically binds a pan-B cell marker, such as B220 (for murine cells).

In some embodiments, an antibody that specifically binds CD25 is utilized. In one example, the anti-C25 antibody is a monoclonal anti-Tac antibody, such as daclizumab. Other anti-p55 agents include the chimeric antibody basiliximab (SIMULECT®), BT563 (see Baan et al., *Transplant. Proc.* 33:224-2246, 2001), and 7G8. Basiliximab has been reported to be beneficial in preventing allograft rejection (Kahan et al., *Transplantation* 67:276-84, 1999), and treating psoriasis (Owen & Harrison, *Clin. Exp. Dermatol.* 25:195-7, 2000). An exemplary human anti-p55 antibody of use in the methods of the invention is HUMAX®-Tac. Additional antibodies that specifically bind the IL-2 receptor are known in the art. For example, see U.S. Pat. No. 5,011,684; U.S. Pat. No. 5,152,980; U.S. Pat. No. 5,336,489; U.S. Pat. No. 5,510,105; U.S. Pat. No. 5,571,507; U.S. Pat. No. 5,587,162; U.S. Pat. No. 5,607,675; U.S. Pat. No. 5,674,494; U.S. Pat. No. 5,916,559.

In an additional embodiment, the antibody specifically binds CD19. Suitable antibodies include, but are not limited to MOR208 (XmAb5574, Morphosys) and BU12 (see the NCI website).

The method can also include administering to the subject a therapeutically effective amount of an additional chemotherapeutic agent. A typical pharmaceutical composition for intravenous administration includes about 0.1 µg to 10 mg of antibody per subject per day. Dosages from 0.1 mg up to about 100 mg per subject per day may be used, particularly if the agent is administered to a secluded site and not into the circulatory or lymph system, such as into a body cavity or into a lumen of an organ. Actual methods for preparing administrable compositions will be known or apparent to those skilled in the art and are described in more detail in such publications as *Remington's Pharmaceutical Science,* 19th ed., Mack Publishing Company, Easton, Pa. (1995).

Antibodies may be provided in lyophilized form and rehydrated with sterile water before administration, although they are also provided in sterile solutions of known concentration. The antibody solution is then added to an infusion bag containing 0.9% sodium chloride, USP, and typically administered at a dosage of from 0.5 to 15 mg/kg of body weight. Considerable experience is available in the art in the administration of antibody drugs, which have been marketed in the U.S. since the approval of RITUXAN® in 1997. Antibodies can be administered by slow infusion, rather than in an intravenous push or bolus. In one example, a higher loading dose is administered, with subsequent, maintenance doses being administered at a lower level. For example, an initial loading dose of 4 mg/kg may be infused over a period of some 90 minutes, followed by weekly maintenance doses for 4-8 weeks of 2 mg/kg infused over a 30 minute period if the previous dose was well tolerated.

The agent that inhibits tBreg cells can be administered with a tumor antigen, or a nucleic acid encoding a tumor antigen Tumor antigens are proteins that are produced by tumor cells that elicit an immune response, particularly T-cell mediated immune responses. The tumor antigen can be any tumor antigen, which are well known in the art and include, for example, carcinoembryonic antigen (CEA), β-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, macrophage colony stimulating factor, prostase, prostate-specific antigen (PSA), PAP, NY-ESO-1, LAGE-1a, p53, prostein, PSMA, Her2/neu, survivin and telomerase, prostate-carcinoma tumor antigen-1, MAGE, ELF2M, neutrophil elastase, ephrinB2, CD22, insulin growth factor (IGF)-I, IGF-II, IGF-I receptor and mesothelin. A list of selected tumor antigens and their associated tumors are shown below in Table 2.

TABLE 2

Exemplary tumors and their tumor antigens

| Tumor | Tumor Associated Target Antigens |
|---|---|
| Acute myelogenous leukemia | Wilms tumor 1 (WT1), PRAME, PR1, proteinase 3, elastase, cathepsin G |
| Chronic myelogenous leukemia | WT1, PRAME, PR1, proteinase 3, elastase, cathepsin G |
| Myelodysplastic syndrome | WT1, PRAME, PR1, proteinase 3, elastase, cathepsin G |
| Acute lymphoblastic leukemia | PRAME |
| Chronic lymphocytic leukemia | Survivin |
| Non-Hodgkin's lymphoma | Survivin |
| Multiple myeloma | NY-ESO-1 |
| Malignant melanoma | MAGE, MART, Tyrosinase, PRAME GP100 |
| Breast cancer | WT1, herceptin, epithelial tumor antigen (ETA) |
| Lung cancer | WT1 |
| Ovarian cancer | CA-125 |
| Prostate cancer | PSA |
| Pancreatic cancer | CA19-9, RCAS1 |
| Colon cancer | CEA |
| Renal cell carcinoma (RCC) | Fibroblast growth factor 5 |
| Germ cell tumors | AFP |

Suitable subjects may include those diagnosed with a cancer such as, but not limited to, melanoma, prostate cancer, squamous cell carcinoma (such as head and neck squamous cell carcinoma), breast cancer (including, but not limited to basal breast carcinoma, ductal carcinoma and lobular breast carcinoma), leukemia (such as acute myelogenous leukemia and 11q23-positive acute leukemia), a neural crest tumor (such as an astrocytoma, glioma or neuroblastoma), ovarian cancer, colon cancer, stomach cancer, pancreatic cancer, bone cancer (such as a chordoma), glioma or a sarcoma (such as chondrosarcoma). In one specific non-limiting example, the subject has breast cancer.

A therapeutically effective amount of the antibody will depend upon the severity of the disease and the general state of the patient's health. A therapeutically effective amount of the antibody is that which provides either subjective relief of a symptom(s) or an objectively identifiable improvement as noted by the clinician or other qualified observer. These compositions can be administered in conjunction with another chemotherapeutic agent, either simultaneously or sequentially.

Many chemotherapeutic agents are presently known in the art. In one embodiment, the chemotherapeutic agent is selected from the group consisting of mitotic inhibitors, alkylating agents, anti-metabolites, intercalating antibiotics, growth factor inhibitors, cell cycle inhibitors, enzymes, topoisomerase inhibitors, anti-survival agents, biological response modifiers, anti-hormones, e.g. anti-androgens, and anti-angiogenesis agents.

The method can also include obtaining a biological sample from the subject, and measuring the amount of tBreg cells, as discussed below.

Method of Monitoring the Efficacy of Therapy

Methods are disclosed herein for monitoring the efficacy of therapy, including the treatment of autoimmune diseases and cancer. The methods include administering an agent to a subject of interest. A biological sample is obtained from the subject, and the presence of tBreg cells is assessed. The agent can be any agent of interest, including, but not limited to, a cell, a chemotherapeutic agent, an immunostimulatory agent, an immunosuppressive agent, and an antibody.

In one embodiment, an immunostimulatory agent or chemotherapeutic agent is administered to a subject in need of stimulating the immune response. Following administration of the immunostimulatory agent or the chemotherapeutic agent, a biological sample is obtained from the subject, and the presence of tBreg cells is assessed. A decrease in the number of tBreg cells, as compared to a control, indicates the immunostimulatory or chemotherapeutic agent is effective to increase an immune response in the subject. In some embodiments, the subject has cancer.

In another embodiment, an immunosuppressive agent is administered to a subject in need of suppression of the immune response. Following administration of the immunosuppressive agent, a biological sample is obtained from the subject, and the presence of tBreg cells is assessed. An increase in the number of tBreg cells, as compared to a control, indicates the immunosuppressive agent is effective to increase an immune response in the subject. In some embodiments the subject has inflammation and/or an autoimmune disease.

In several embodiments, the method includes comparing the number of tBreg cells to a control. The control can be a standard value, or the number of tBreg cells in a sample from a control subject not treated with the agent, or the number of tBreg cells in a sample from the subject prior to treating the subject with the agent.

In some embodiments, the number of regulatory B cells expressing CD25, and CD19 (CD25$^+$CD19$^+$), that suppress T cells in cell contact-dependent manner, is assessed. In additional embodiments, the presence of tBreg cells that express CD21 and CD23, and/or express high levels of CD81 is assessed. In additional embodiments the presence of regulatory B cells that express one or more of CD40, CD69, CD80, CD86, BAFF-R, CCR6, CXCR5 and an MHC molecule is assessed. Thus, the presence of regulatory B cells that express two, three, four, five, six or all seven of CD40, CD69, CD80, CD86, BAFF-R, CCR6, CXCR5 can be assessed. The presence of tBreg cells that express MHC molecules, such as MHC class I or MHC class II can be assessed. In additional embodiments, the presence of regulatory B cells that express one or more of TSLPR, Fas, FasL and programmed death (PD)-1 is assessed. In further embodiments, the presence of B cells that do not express CD5 and/or CD27 is assessed. In other embodiments, the presence of tBreg cells that express phosphorylated STAT3 is assesed. In one, non-limiting example, the presence of regulatory B cells that are pStat3$^+$ CD25$^{High}$B7-H1$^{High}$CD86$^{High}$CCR6$^{High}$ and CD62$^{Low}$IgM$^{Int/Low}$ B cells is assessed. In any of these embodiments, the number of cells can be quantitated.

In additional embodiments, the ability of tBreg cells to induce generation of FoxP3$^+$ regulatory T cells (Tregs) from CD8$^+$ and/or CD4$^+$ T cells is also assessed. In one embodiment, an immunostimulatory agent is administered to a subject. Following administration of the immunostimulatory agent or chemotherapeutic agent, a biological sample is obtained from the subject, and the ability of tBreg cells to induce generation of FoxP3$^+$ regulatory T cells (Tregs) from CD8$^+$ and/or CD4$^+$ T cells is assessed. A decrease in the number of Treg cells, as compared to a control, indicates the immunostimulatory or chemotherapeutic agent is effective to increase an immune response in the subject.

In another embodiment, an immunosuppressive agent such as a chemotherapeutic agent, is administered to a subject. Following administration of the immunosuppressive agent, a biological sample is obtained from the subject, and the ability of tBreg cells to induce generation of FoxP3$^+$ regulatory T cells (Tregs) from CD8$^+$ and/or CD4$^+$ T cells is assessed. An increase in the number of Treg cells, as compared to a control, indicates the immunosuppressive agent is effective to decrease an immune response in the subject.

The disclosure is illustrated by the following non-limiting Examples.

EXAMPLES

Some recent findings indicate that B cells can possess regulatory functions and alleviate autoimmune diseases (Rafei et al., Nat. Med. 2009; 15:1038-45; Ito et al., J. Immunol. 2004; 172:3628-34; Matsushita et al., J. Clin. Invest. 2008; 118:3420-30; Byrne et al, J. Invest. Dermatol. 2005; 124:570-8). For example, T cell-dependent autoimmunity in mice is associated with the lack of a small subset (1-2% of B220$^+$ cells) of IL-10-producing CD1d$^{High}$CD5$^+$ B cells (so called B10 cells) (Yanaba et al., Immunity. 2008; 28:639-50). In addition, B1b (CD5$^-$CD1d$^{High}$ B220$^{Low}$ CD11b$^+$IgM$^+$) suppressive cells in mice and CD19$^+$CD24$^{High}$CD38$^{High}$ B cells in humans are linked with protection from murine chronic colitis (Shimomura et al., IntImmunol. 2008; 20:729-37; Mizoguchi et al., Immunity. 2002; 16:219-30) and systemic lupus erythematosus, respectively (Blair et al., Immunity. 2010; 32:129-40). Interestingly, although suppressive activity of B cells can be IL-10-independent, for example, in protection from EAE (Frommer et al., J. Immunol. 2008; 181:5748-59), the majority of them appeared to utilize IL-10. LPS activation of naïve B cells alone can induce IL-10 production and suppress T cell responses inducing H-Y antigen tolerance (Fuchs et al., Science. 1992; 258:1156-9).

Although mammary adenocarcinoma 4T1 cancer cells (which spontaneously metastasize to various organs after implantation into the mammary gland of immune competent BALB/C mice) consisted of metastatic CCR4$^+$4T1 and non-metastatic 4T1-PE cell subsets, the CCR4$^+$4T1 cells could not establish metastasis without essential help from CCR4$^+$ Tregs to inactivate anticancer NK cells (Olkhanud et al., supra). The process was also associated with a significant increase in Treg numbers. It is disclosed herein that, although a number of other APCs can induce the generation of Tregs, Treg expansion is mediated by a unique subset of B cells, designated tumor-evoked regulatory B cells (tBregs). Although tBregs can directly suppress T cell responses, their role in cancer metastasis is in their ability to induce the generation of FoxP3$^+$Tregs from non-regulatory CD4$^+$ T cells (non-Tregs). Since tBregs by themselves are also generated from normal resting B cells in response to secreted products from non-metastatic subsets of breast cancer cells, the data presented herein link B cells, specifically tBregs, with cancer escape and metastasis. This suggests that as long as cancer persists it will generate tBregs to thereby initiate a chain of suppressive events leading to successful metastasis.

Example 1

Materials and Methods

Cells and Mice.
Female BALB/C, C57Bl/6, non-obese diabetic severe combined immunodeficient (SCID; NOD.CB17-Prkdc$^{scid}$/J) mice and mice with mature B cell deficiency (B6.129P2-Igh-J$^{tm1Cgn}$/J) were obtained from the Jackson Laboratory (Bar Harbor, Me.). 4T1 cells, B16F10 melanoma, MCF-7 and MDA-231, OVCAR3, B-2008, BG1 UCI101, SW480 cells were purchased from American Type Culture Collection. 4T1.2 cells are a subset of 4T1 cells. 4T1-PE cells were generated from 4T1 by using TARC-PE38 chemotoxin (Olkhanud et al, Cancer Res. 2009; 69:5996-6004), 4T1-R4 and 4T1-R3 cells were cloned by sorting cells based on differences in Hoechst 33341 blue and red fluorescence (Biosciences).

In Vitro tBreg and Treg Generation and T Cell Suppression Assay.

Murine splenic B cells were isolated by negative selection using the ROBOBSEP™ magnetic purification system (StemCell Technologies, Vancouver, Canada). For tBreg generation, B cells were incubated with 50% cancer CM for two days in cRPMI. Control B cells were treated with PBS, or 100 ng/ml BAFF, or 5 µg/ml LPS. Cancer CM was collected from 72 hours cultured in cRPMI cancer cells. Mouse $CD3^+$ T cells were isolated from naïve mouse spleen using T cell enrichment columns (R&D Systems, Minneapolis, Minn.). To generate non-Tregs, $CD4^+$ T cells were isolated by mouse T cell CD4 Subset Column Kit and separated from $CD25^+$ cells using CD25 Microbead kit (Miltenyi Biotec, Auburn, Calif.). The $CD25^+CD4^+$ cells were used as Tregs. To test the suppressive effects of B cells, B cells were cultured together with carboxyfluorescein succinimidyl ester (CFSE, Invitrogen, Carlsbad, Calif.)-labeled T cells ($1\times10^5$) in the presence of anti-CD3/CD28-coupled beads or soluble anti-CD3 Ab (1 µg/ml) for 4 days. Decrease in CFSE expression of T cells correlates with the proportion of cells that underwent divisions.

To generate Tregs, tBregs were incubated with non-Treg cells ($CD25^-CD4^+$) at a 1:1 ratio and cultured for 5 days in the presence of bead-conjugated anti-CD3/CD28 Abs and 500 U/ml IL-2. To test their activity, Tregs were re-isolated by two rounds of B cell depletion with FITC-CD19 and PE-B220 Abs (BD Pharmingen) and anti-FITC and anti-PE beads (Miltenyi Biotec) and mixed with naïve CFSE-labeled $CD8^+$ T cells in the presence of bead-conjugated anti-CD3/CD28 Abs and 500 U/ml IL-2 for 4 days.

In Vivo Manipulations

Animal care was provided in accordance with the procedures outlined in the Guide for the Care and Use of Laboratory Animals (NIH Publication No. 86-23, 1985). The experiments were performed using 4-8 weeks old female mice in a pathogen-free environment at the National Institute on Aging Animal Facility, Baltimore, Md. To deplete Tregs and tBregs, mice were intraperitoneally (i.p.) injected with antibodies (Abs) to mouse CD25 (500 µg; PC-61, BioXcell, West Lebanon, N.H.) and B220 (400 µg; RA3.3A1, BioXcell) or control IgG at days 3, 10 and 18 post tumor challenge. To restore metastasis, NOD/SCID mice were i.v. injected with $1\times10^7$ tBregs, generated from naïve BALB/C B cells two days treated with CM-4T1PE, together with equal amounts of BALB/C non-Tregs at days -1, 3 and 7 after tumor challenge. Control NOD/SCID mice were injected with $1\times10^7$ BALB/C non-Tregs. Congeneic mice were challenged s.c 4T1.2 tumor cells (in 4th mammary gland with $1\times10^4$ cells) or $1\times10^5$ B16 melanoma F10 cells; tumor growth was measured every other day. Mice were culled after 28 days of tumor challenge and lungs were analyzed for metastasis as previously described (4). Tumor burden in the lungs was quantified by counting nodules.

Reagents Used for Flow Cytometry

The reagent utilized were from BD Pharmingen (San Diego, Calif.): Fc block and antibodies (APC-B220, PE-CD25, FITC-CD19, PE-CD80, FITC-CD86, FITC-CD40, PE-CD43, PE-MHC I, FITC-MHC II, FITC-IgM, FITC-CD95, PE-CD95L, FITC-CD5, PE-CD21, PE-CD23, PE-CD27, PE-CD62L, FITC-CD69, PE-CD93, PE-TSLPR); or from eBioscience (San Diego, Calif.): PE-PD1, PE-B7H1, PE-PDGFR$^a$ or from R&D Systems: FITC-CCR6, FITC-CXCR4, PE-CXCR5; or from AbD Serotec (Raleigh, N.C.): FITC-CCR7. For intracellular staining for IL-10 and FoxP3, cells were first stained with surface marker staining Abs such as APC-B220 or APC-CD4 before overnight fixation and permeabilization and staining with anti-Foxp3-PE antibody according to the manufacturer's instructions (Mouse Regulatory T cell Staining kit, eBioscience). Cells were analyzed by flow cytometry using a FACScalibur™ (BD Pharmingen) with CELLQUEST® software (BD Pharmingen).

Mice and Cells and Cell Manipulations

Knockout mice for Ebi3 and IL-10 were purchased from the Jackson Laboratory (Bar Harbor, Me.). Splenocytes from B7-H1 KO mice were obtained from the Lerner Research Institute. A drug resistant subset of MCF7 cells, MCF7D40, were obtained form King's College, UK, FS melanoma cells were obtained from the National Institutes of Health, USA. Cells were grown in cRPMI (RPMI 1640 medium supplemented with 10% heat inactivated fetal bovine serum, plus 1 mM sodium pyruvate, 100 U/ml penicillin, 100 µg/ml streptomycin, 2-ME, HEPES (Gibco, Gaithersburg, Md.) in a 5% $CO_2$ incubator.

Murine splenic B cells were isolated by negative selection using ROBOSEP™ magnetic purification system (StemCell Technologies, Vancouver, Canada). Human peripheral blood was taken from healthy donors. Human B cells were isolated from PBMCs using DYNABEADS® Untouched Human B Cells (Invitrogen, Carlsbad, Calif.) after Ficol-Paque (GE Healthcare Bio-Sciences Corp., Piscataway, N.J.) density gradient-separation. For tBreg induction, mouse or human B cells were incubated with 50% conditioned medium (CM) from corresponding cancer cells for two days in cRPMI. Control B cells were treated with PBS or 5 µg/ml LPS. Tumor CM was collected from 72 hours cultured with cancer cells. Proliferation of B cells was tested using carboxyfluorescein succinimidyl ester (CFSE, Invitrogen)-labeled B cells after five days treatment. The decrease in CFSE expression among $CD19^+$ cells is considered the proportion of B cells that underwent divisions. For Western blotting, 8 µg whole cell extracts in ice-cold RIPA buffer (Santa Cruz Biotechnology) were separated in SDS-PAGE gel and transferred to PVDF membranes and hybridized with antibody to Bcl-xL, p27, phospho-Rb (S807/811), phospho-Stat3 (all from Cell Signaling), Cyclin D2, Cyclin E (Santa Cruz), Bim (BD Biosciences), and β-actin (Sigma).

Mouse $CD3^+$ T cells were isolated from naïve mouse spleen using T cells enrichment columns (R&D Systems, Minneapolis, Minn.). To generate non-Tregs, $CD4^+$ T cells were isolated by mouse T cell CD4 Subset Column Kit and separated from $CD25^+$ cells using CD25 Microbead kit (Miltenyi Biotec, Auburn, Calif.). The $CD25^+CD4^+$ cells were used as Tregs. Human $CD3^+$ T cells isolated from PBMCs using human $CD3^+$ T cell enrichment columns (R&D Systems). $CD4^+$ and $CD8^+$ T cells were further isolated by negative selection corresponding columns (R&D Systems). To assess the role of soluble or surface molecules, tBregs and T cells were cultured in the presence of neutralizing Abs against mouse CTLA-4 (50 µg/ml, clone UC10-4B9, BioLegend, San Diego, Calif.), CCL3/MIP-1α (1 µg/ml, WZ06, R&D Systems), CCL4/MIP-1β (3 µg/ml, clone 46907, R&D Systems), TGF-β (50 µg/ml, clone 1D11, R&D Systems), or human PD-1 (20 µg/ml, ICA01, R&D Systems), B7-H1 (20 µg/ml, clone MIH1, eBioscience), and FasL (50 µg/ml, clone NOK-1, BD Pharmingen) or their isotype-matched control Abs. Transwell plates (0.4 μm pore size, Corning Costar, Cambridge, Mass.) were used to test the role of cell contact. Cells were stained with propidium iodide (PI) to exclude or evaluate the proportion of dead cells.

The Generation of Metastatic 4T1-R3 and Non-Metastatic 4T1-R4 Cell Subsets Form 4T1 Cancer Cells.

Generation was evaluated based on differences in Hoechst 33341 blue and red fluorescence (Biosciences, see Supplements). Briefly, 4T1 cells were harvested using trypsin-EDTA and resuspended in Iscove's DMEM (Invitrogen) supplemented with 2% fetal bovine serum (FCS) on ice. For side population analysis, $1 \times 10^6$ cells were stained with 5 ug/ml Hoechst 33342 (Biosciences) for 90 minutes at 37C, as described (Kruger et al. Blood 108:3906, 2006). To ascertain the specificity of the side population staining, cells were stained in the presence of 100 mM verapamil hydrochloride, which abolishes the SP. Propidium iodide was added (1 ug/ml) prior to analysis in order to exclude dead cells. Cell sorting was performed using a Beckman-Coulter MOFLO® high speed cell sorter.

Cell Viability.

Viability was assessed after 48-72 hours culture using cell proliferation reagent WST-1 (Roche Applied Science). To test tBreg-mediated apoptosis of NK cells, CFSE stained NK cells were cultured for 16 hours with titrated amounts of either tBregs, or normal B cells in U-bottom 96-well plates in RPMI with 10% FBS and 1000 U/ml human IL-2. PI and annexin-V-Fluor Staining kit (Roche Applied Science) was used assess to assess apoptosis. NK cells were isolated from splenocytes of naïve mice using NK cell isolation kit (Miltenyi) according manufacturer's instructions. To test effects of tBregs on the cytolytic activity of NK cells, titrated amounts of B cells or tBregs were incubated with NK cells for 3 hours and cultured with target YAC1 cells ($1 \times 10^4$ cells per well) labeled with $Na_2{}^{51}CrO_4$ (Perkin-Elmer) for 4 hours at 37° C. in triplicates in 96-well round-bottomed plates. The specific $^{51}Cr$ release is calculated using the formula: [(test sample release–spontaneous release)/(maximum release–spontaneous release)]×100. Maximum release is for the target cells alone lysed with 2% Triton X-100.

Chemoarp-Mediated Anti-Sense Oligonucleotide Transduction of Primary B Cells.

Since primary cells cannot be efficiently transduced by oligonucleotides, a *Pichia pastoris* expression system was used to produce and purify recombinant chemokines that contained 10 amino acid tail encoding the RNA-binding domain of HBV. As a result, the recombinant chemokine, designated chemoarp absorbs oligonucleotides and delivers them into primary immune cells acting via their chemokine receptors. In this work, modified BLC/CXCL13 (BLC-Arp) was used to target CXCR5+ B cells. Following anti-sense oligonucleotides were used in the work to knock off all three BAFF receptors, such as BAFF-R (AGCGCCAGTATCAGTCCAGG and TTCTGAGGAGGGTACAAAGAC, SEQ ID NO: 1 and 2), BCMA (TGTACGTCCCTTTCACTGAAC and ATCGCAAGTGACACGGTTTGC, SEQ ID NO: 3 and 4), and TACI (TTTGCAGAAGTCTGTACAGGT and TACTTAGCCTCAATCCTGGAC, SEQ ID NO: 5 and 6). To transduce B cells, BLC-Arp 12 μg/ml) and antisense oligos (36 μg/ml) were pre-incubated 30 minutes at 4° C. prior to mixing with B cells seeded at the density $0.1 \times 10^6$ cells in 25 μl of RPMI without FBS. After 30 minutes of incubation at 37° C. with 5% $CO_2$, 25 μl of 10% RPMI or CM-4T1PE was added. Viability of cells and expression of BAFF-R receptor was measured after 24 hours.

Example 2

Cancer Induces the Generation of Poorly Proliferative B Cells

Figure 1B:
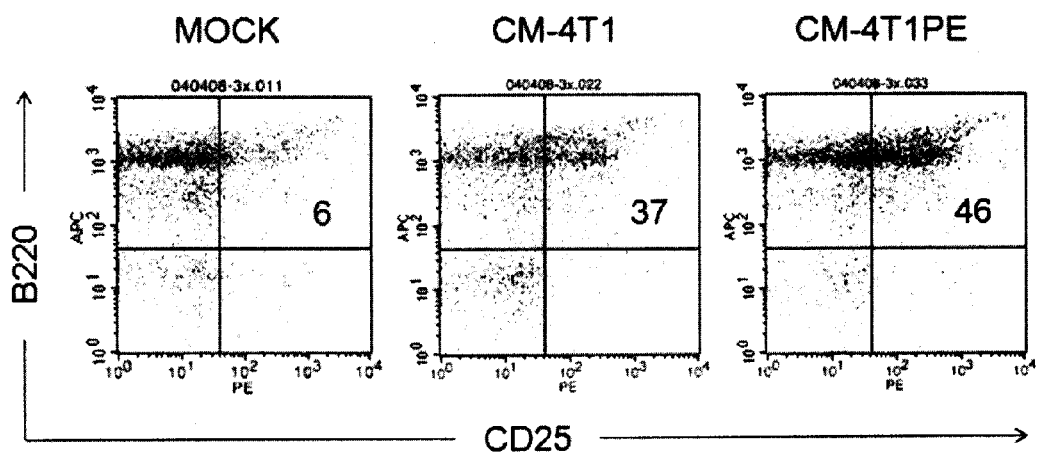
Figure 1C:
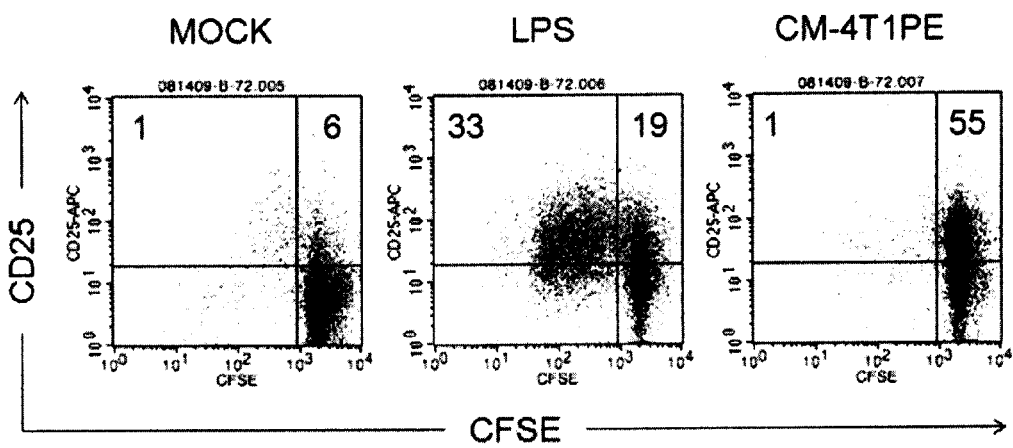
Figure 1D:
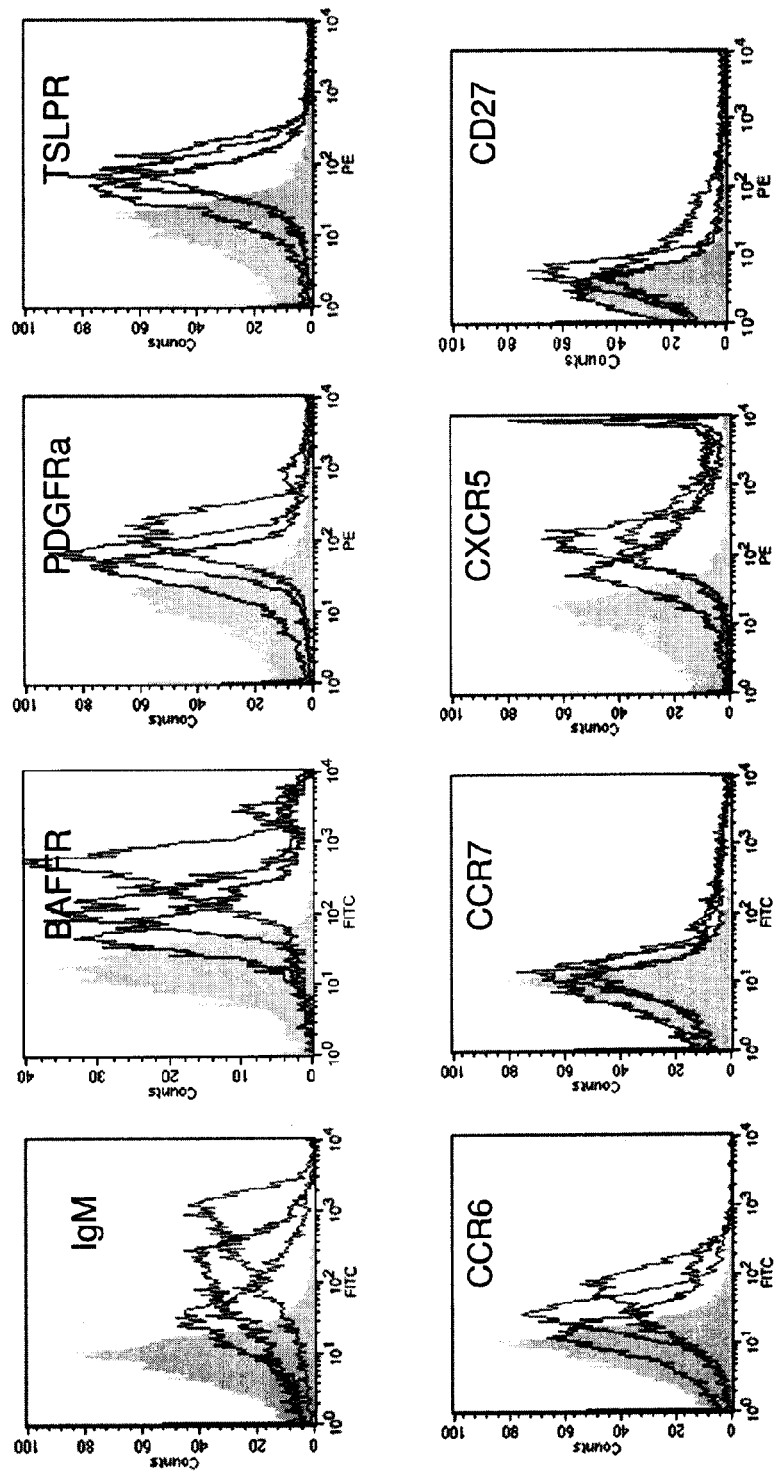
Figure 1E:
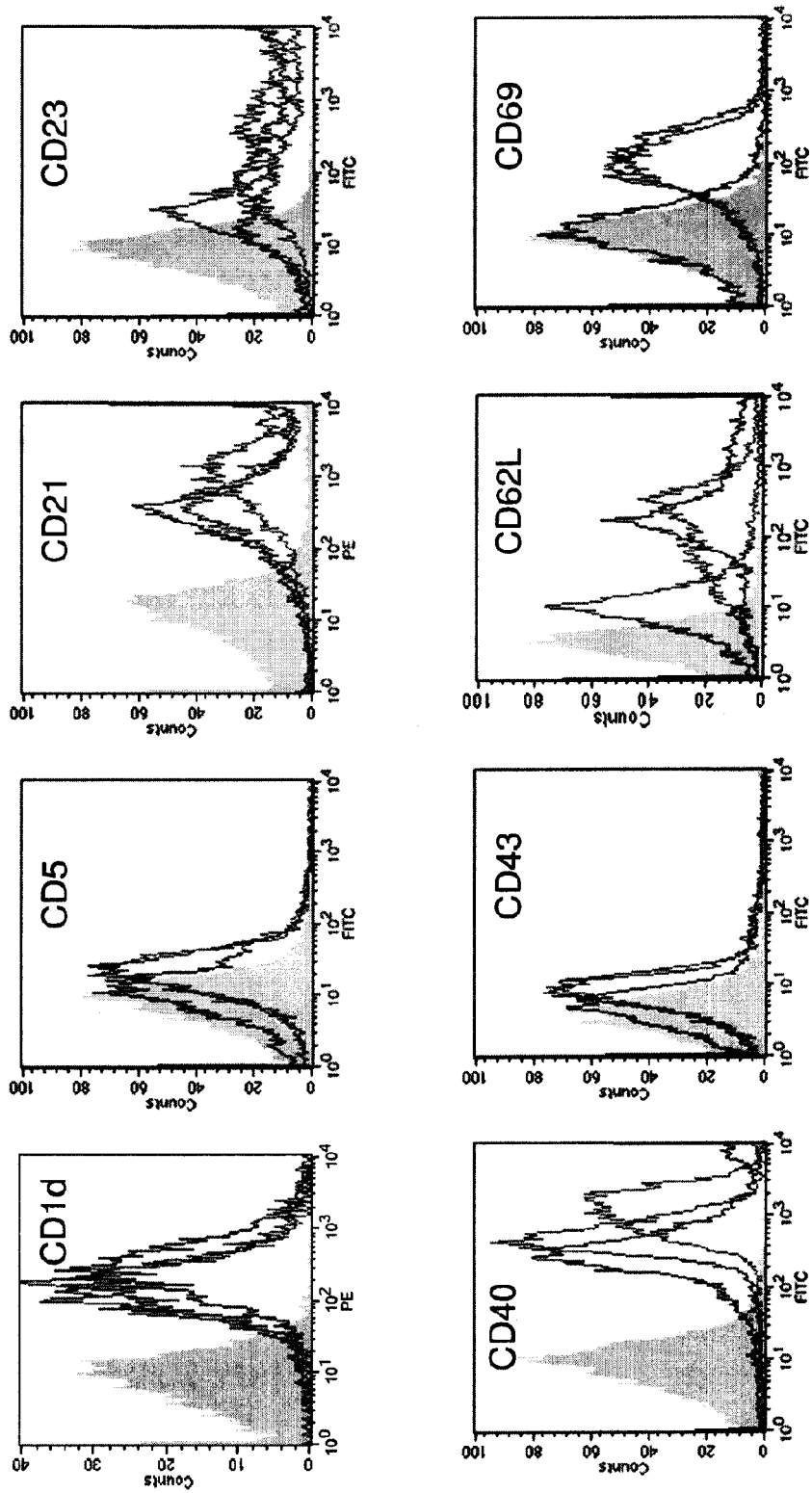
Figure 1F:
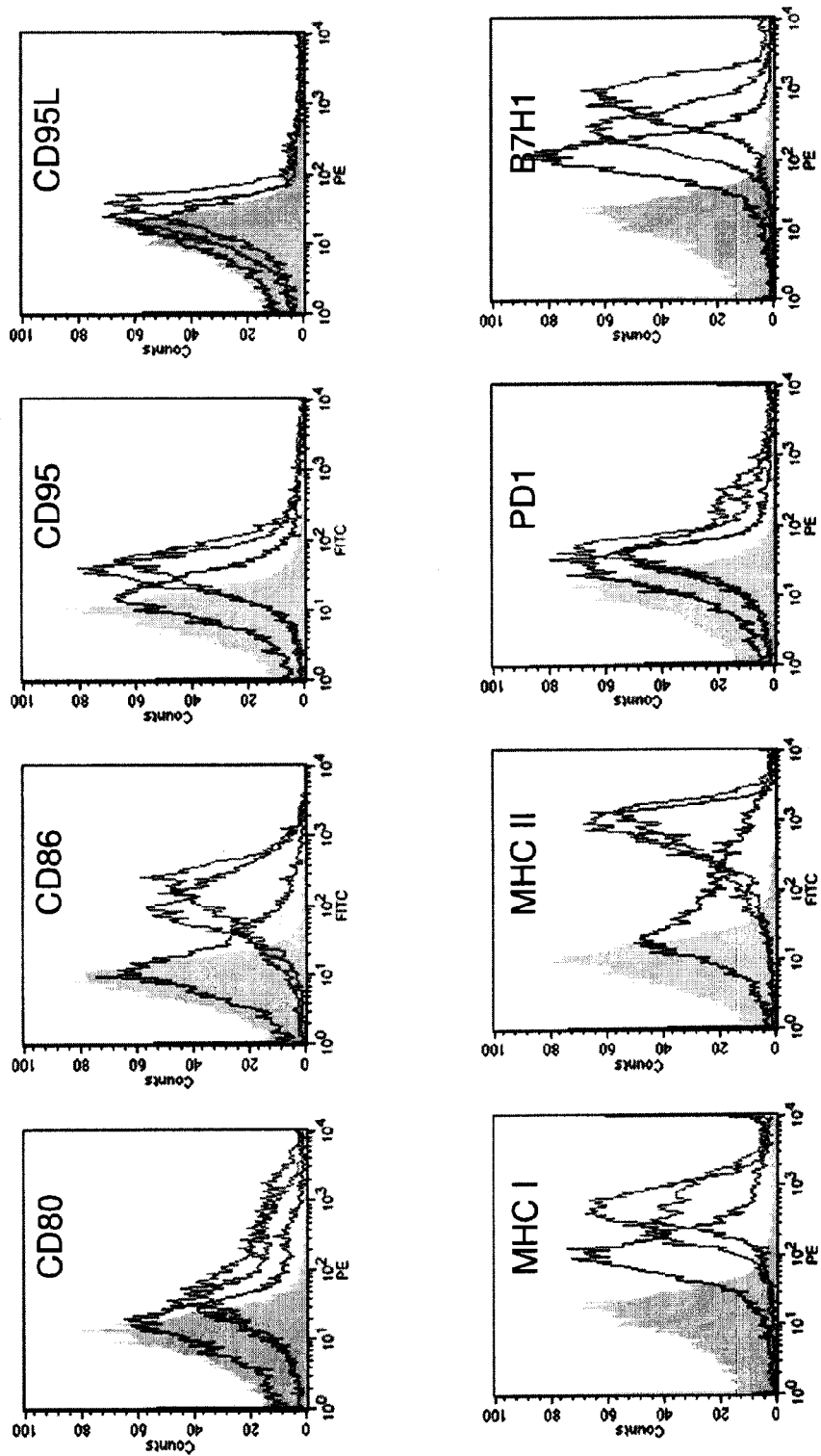
Figure 2B:
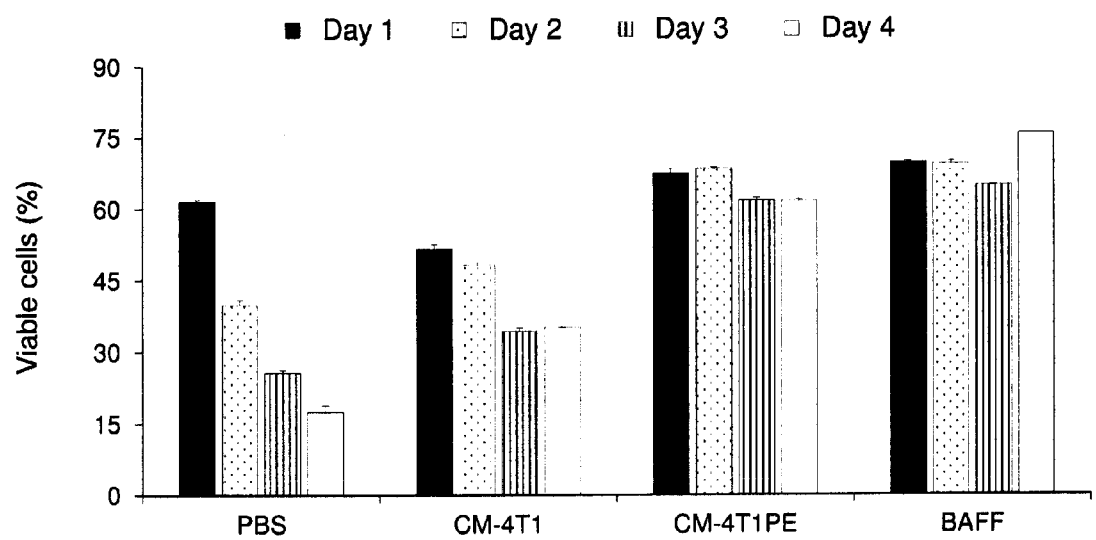
Figure 2B:
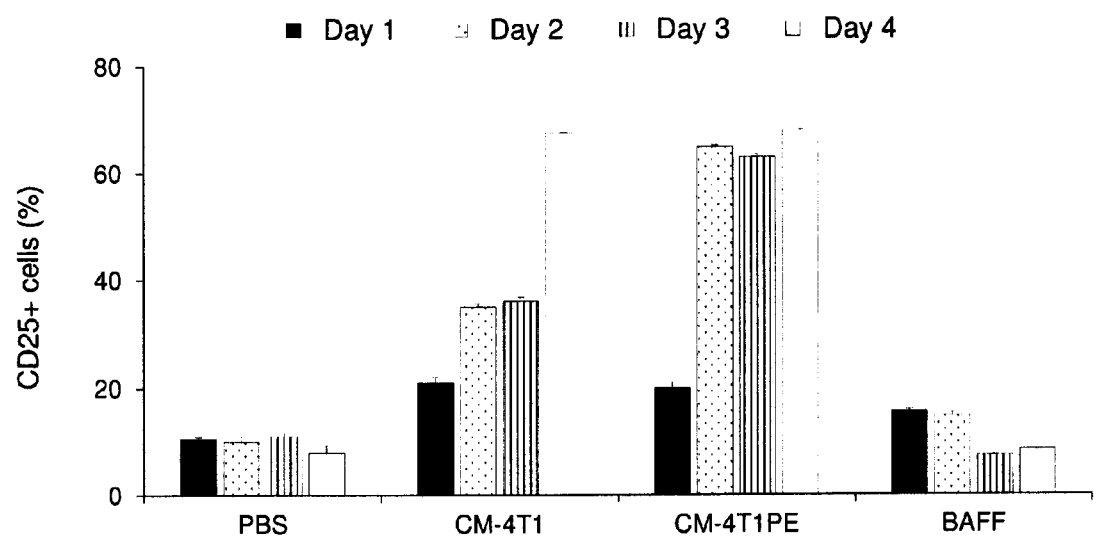

4T1 cancer-bearing BALB/C mice had a small but significantly increased proportion of CD2513220+CD19+ B cells (FIG. 1A), suggesting that cancer could induce their generation. Indeed, similar CD25+ B cells were also generated by injecting naïve mice (FIG. 1B) or treating their B cells in vitro (FIG. 1C) with conditioned media (CM) of 4T1 cells, respectively. Unlike resting B cells, the cancer CM-treated cells also expressed elevated levels of CD40, CD69, CD80, CD86, BAFF-R, CCR6, CXCR5 and MHC class I and II molecules, and moderate levels of TSLPR, Fas, FasL and PD-1 (FIG. 1D). Unlike B10 cells, they were CD5−CD23−CD27−, while expression of CD21 and CD23 were not affected (FIG. 1D). Expression of CD1d may be not affected or may be reduced. Interestingly, B cells treated with LPS expressed a comparable pattern of surface markers (FIG. 1C, D). However, unlike LPS which also induced B cell proliferation (FIG. 1C), cancer CM-treated B cells only expressed low levels of IgM and CD62L and high levels of B7-H1 (FIG. 1D) and did not proliferate (FIG. 1C). The inability to proliferate was associated with a high level of $p27^{Kip1}$ (an inhibitor of G1 progression) expression in the absence of change in cyclins D2/E and retinoblastoma protein levels (FIG. 2A), suggesting that the cells do not progress into S from G1 phase. The cells also constitutively expressed activated STAT3 (FIG. 2A), a Janus kinase-signal transducer and activator of transcription that plays a critical role in the generation of human effector B cells (Avery et al., JExpMed. 2010; 207:155).

Example 3

Non-Metastatic Breast Cancer Cell Subsets Actively Promote Survival of B Cells

Figure 2D:
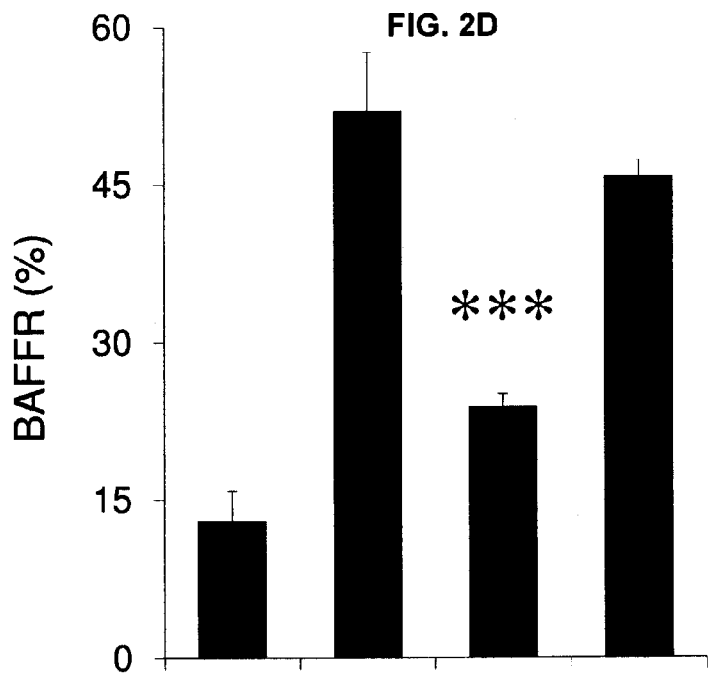
Figure 2D:
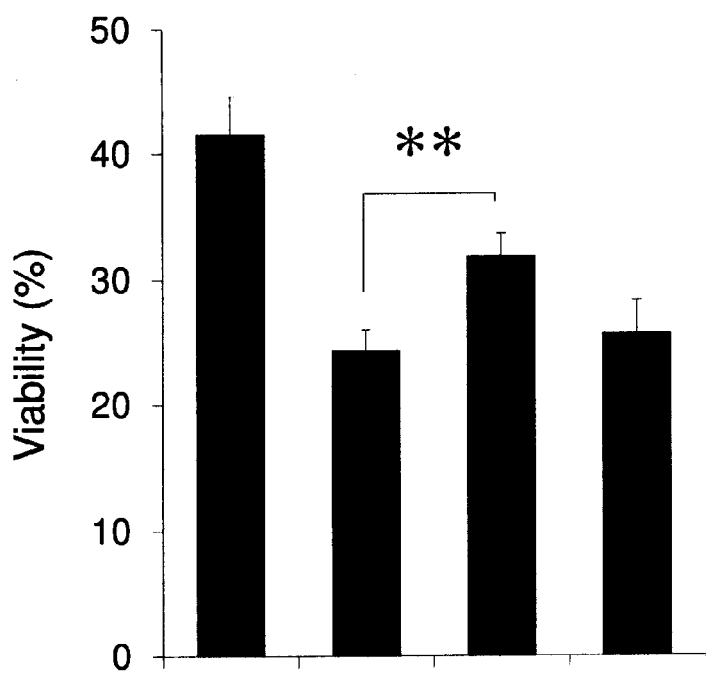
Figure 2E:
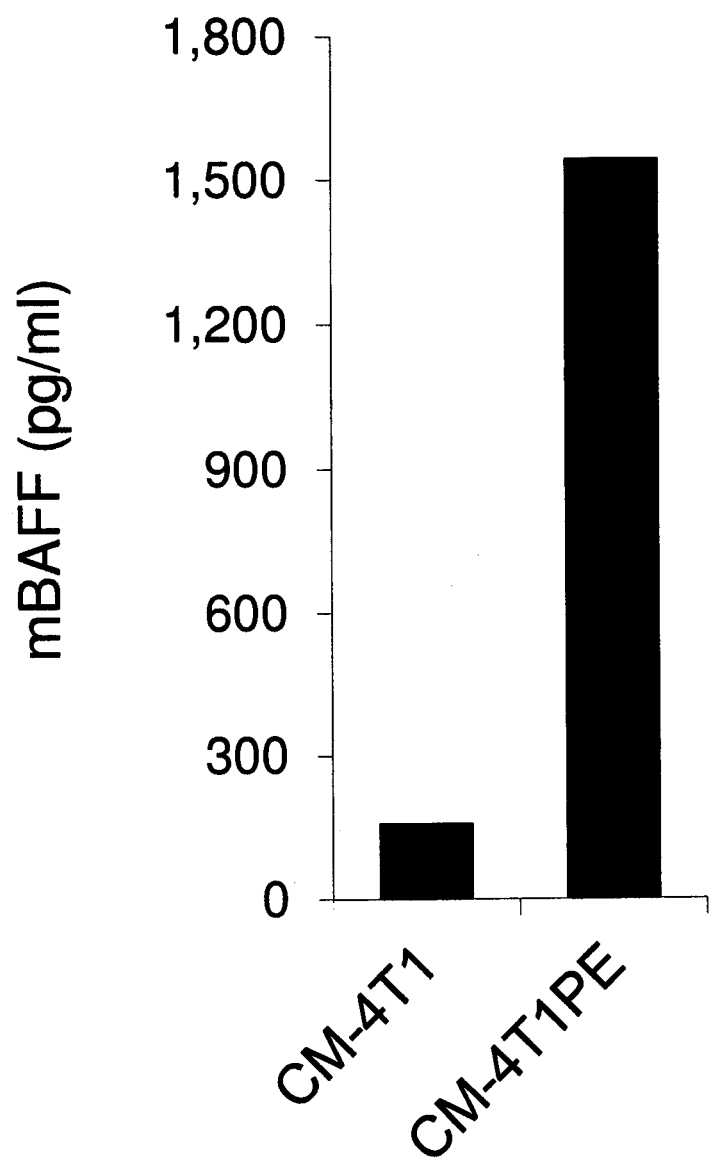
Figure 3A:
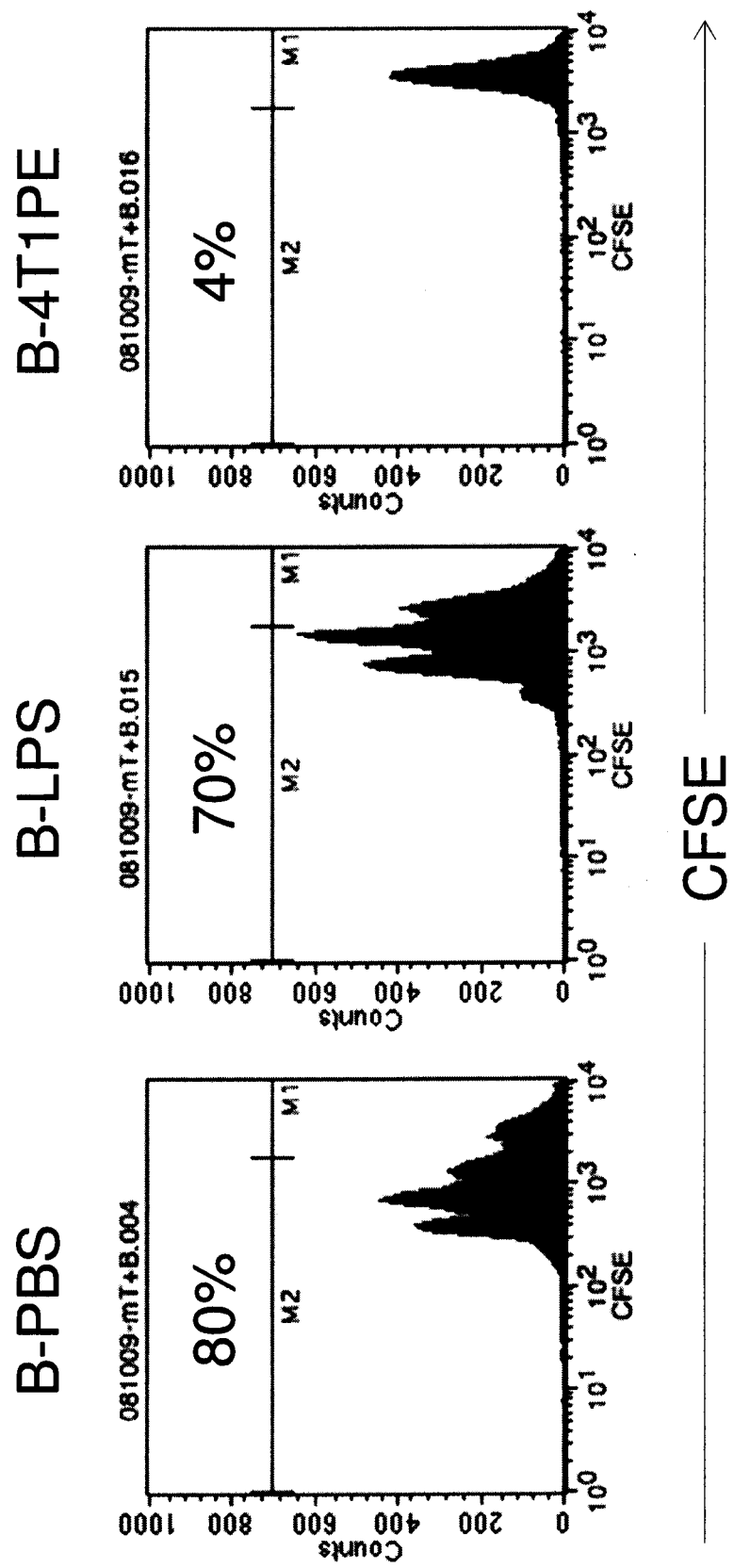
FIG. 3A-3D is a set of graphs. (A) CM-4T1PE, but not mock (B-PBS) or LPS (B-LPS), treated B cells (B-4T1PE) inhibit proliferation of T cells stimulated with anti-CD3/CD28 Abs. B cells and CFSE-labeled T cells (responder) cells were cultured at a 1:1 ratio for four days in the presence of 50 U/ml IL-2. (B) T cell proliferation is efficiently inhibited by B cells cultured in CM from non-metastatic cells (B-4T1PE and B-4T1R$^3$), but not metastatic cells (B-4T1R$^4$) and control BAFF-containing medium (B-BAFF). (C) CD19$^+$ B cells were isolated from spleens of BALB/C mice i.p. injected with control medium or cancer CM (i.p. control CM and ip CM-4T1PE, respectively, see FIG. 1B) and tested in vitro for the ability to suppress T cell proliferation as in FIG. 3A. Purified B cells from CM-4T1PE-treated mice were also depleted using anti-B220 Ab or control IgG prior to mixing with T cells. Controls were B cells in vitro cultured with BAFF or CM-4T1PE (B-BAFF and B-4T1PE, respectively). (D) B-4T1PE cells (generated as in FIG. 1C) inhibit proliferation of T cells even when used at a 1:16 ratio of B cells to T cells. T cell proliferation was as in FIG. 3A. (A-D) Histograms show % of proliferated T cells±SEM of triplicates repeated at least three times. *P<0.05, P<0.01; *P<0.001.
Figure 3B:
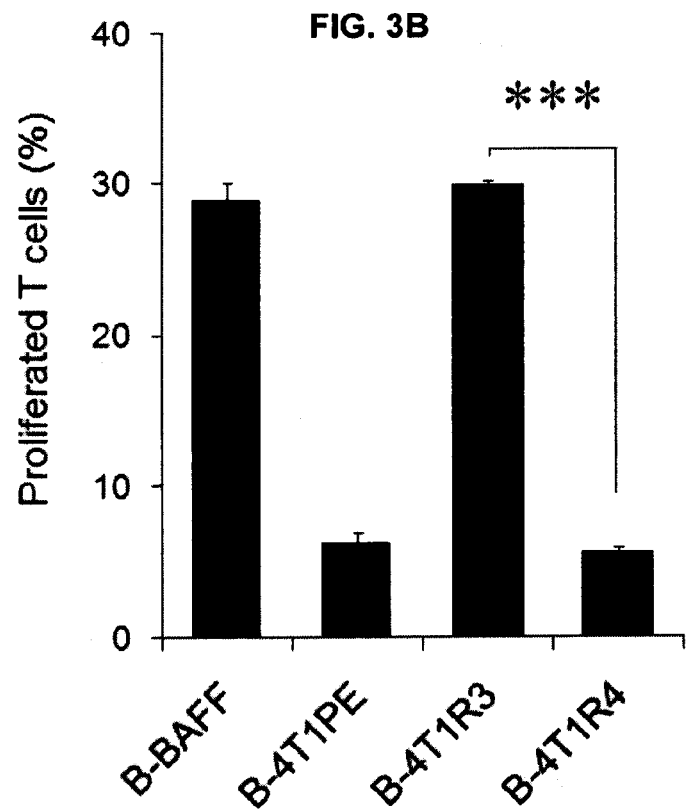
Figure 7A:
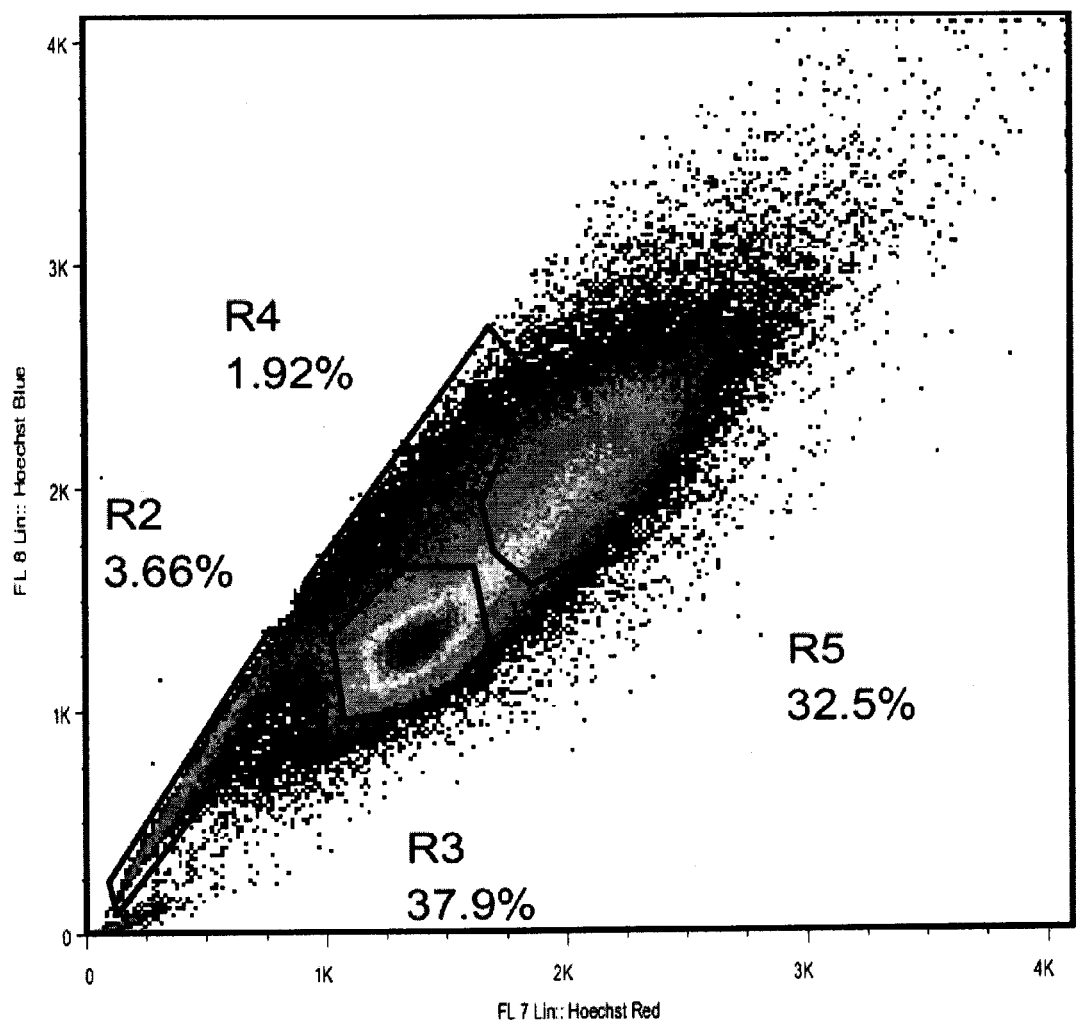
FIG. 7A-B is a set of graphs. (A) 4T1 cells consist of a number of cell subsets. Shown is a profile of 4T1-R3 (R3) and 4T1-R4 cells (R4) that were sorted after staining with 5 ug/ml Hoechst 33342 (Biosciences) for 90 minutes at 37C, as described (Kruger et al. Blood 108:3906, 2006). Cell sorting was performed using a Beckman-Coulter MOFLO™ high speed cell sorter. (B) Murine splenic B cells up regulate CD25 when cultured in CM of non-metastatic cell subsets, 4T1-PE and 4T1-R4. Numbers depict % of $CD25^+CD19^+$ cells. Control B cells were treated with PBS or LPS (10 μg/ml)
Figure 7B:
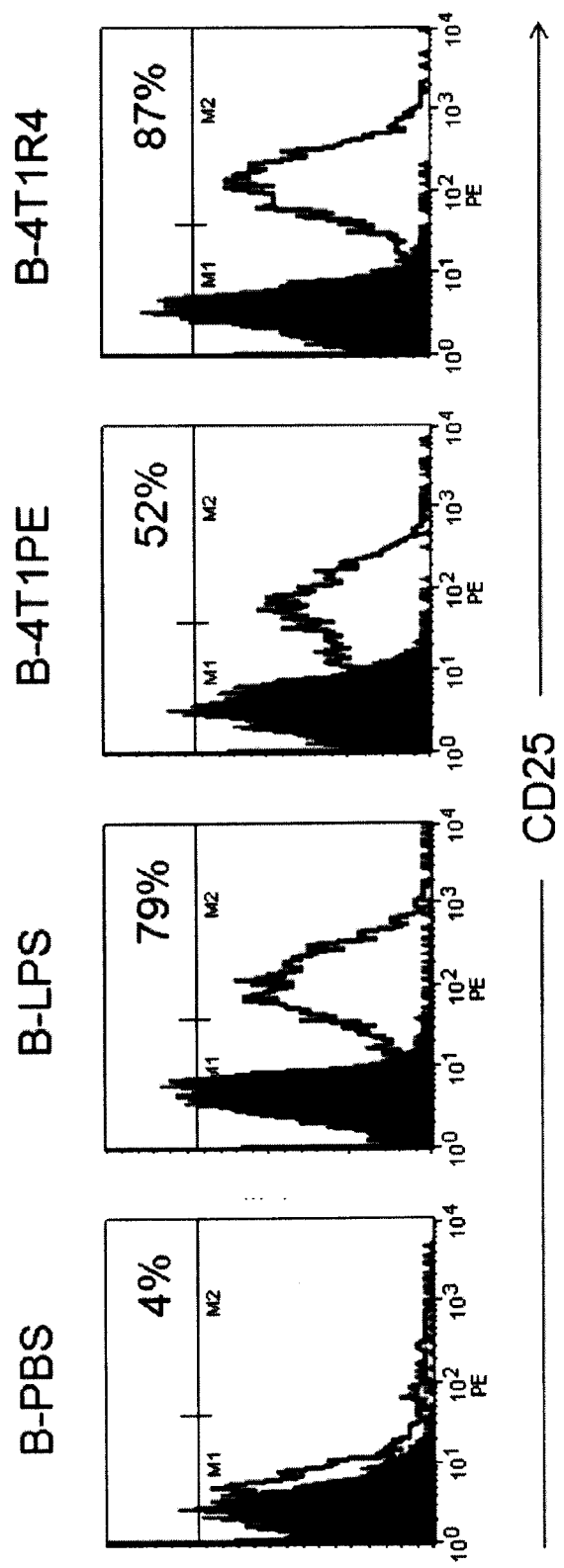

Compared with parental 4T1 cells, its non-metastatic 4T1-PE cells had stronger ability to activate B cells (FIG. 1B and lower panel, FIG. 2B), suggesting that this is a function of non-metastatic cells. To test this, additional clones, such as metastatic 4T1-R3 and non-metastatic 4T1-R4 (FIG. 2C) were generated, using flow cytometry-based sorting technique (FIG. 7A). While 4T1-R3 cells failed to activate B cells (see FIG. 3B), CM from 4T1-R4 and 4T1-PE cells induced robust B cell activation (FIG. 7B). Non-metastatic cells also enhanced the viability of B cells (upper panel, FIG. 2B) which was associated with an elevated expression of anti-apoptotic Bcl-xL (FIG. 2A) and BAFF-R (upper panel, FIG. 2D), suggesting that these cells may also be responsible for B cell survival, for example, by utilizing a key survival factor BAFF (Craxton et al., JExpMed. 2005; 202:1363-74). Indeed, 4T1-PE cells produced BAFF (FIG. 2E), and the oligonucleotide-mediated down-regulation of BAFF-R (upper panel, FIG. 2D), but not BCMA (FIG. 2D), significantly abrogated the viability of B cells treated with CM-4T1PE (lower panel, FIG. 2D).

Example 4

Cancer Induces the Generation of Regulatory B Cells

Figure 8A:
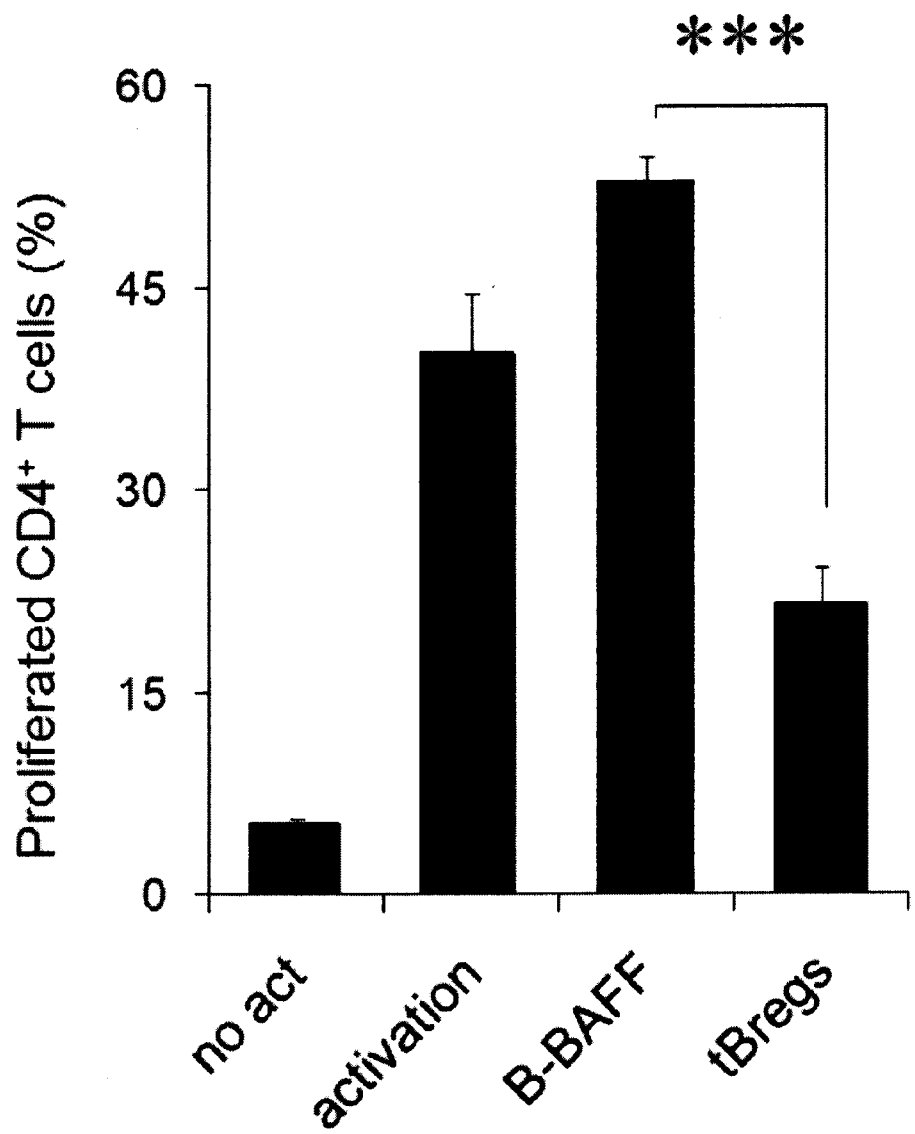
FIGS. 8A-8D are a set of bar graphs. CM-4T1PE, but not control B cells treated with PBS (B-PBS), or BAFF (B-BAFF), or LPS (B-LPS), induce the generation of tBregs (B-4T1PE, tBregs) from both BALB/C (A, B, D) and C57BL/6 (C) mice equally well inhibit proliferation of resting $CD4^+$ T cells (A) or $CD3^+$ T cells (B) and even pre-activated Murine CFSE-labeled T cells (responder) were cultured for four days with B cells (tBregs, or B-LPS, or B-PBS) at 1:1 ratio and stimulated with anti-CD3/CD28 Abs as in FIG. 1C. T cells in (D) were pre-activated with anti-CD3/CD28 Ab treatment in the presence of 50 U/ml IL-2 for 1-3 days. Y-axis, percentage of dividing T cells (mean %±SEM of triplicates repeated at least three times). *** P<0.001.

To test whether the cancer-induced B cells might possess regulatory activity, three types of B cells were generated in vitro by treating naive B cells with cancer cell-derived or control CM, or LPS. The cells were then washed and mixed with CFSE-labeled CD3+ T cells in the presence of anti-CD3/CD28 Ab to activate TCR-mediated proliferation. The B cells treated with CM from 4T1-PE or 4T1-R4, but not metastatic 4T1-R3, cells almost completely prevented T cell proliferation (B-4T1PE and B-4T1R4, FIG. 3A, B), both CD4+ (FIG. 8A) and CD8+ cells. B cells treated with control CM (B-PBS and B-BAFF, FIG. 3A, B) or lipopolysaccharide (LPS) (which by themselves expressed CD25 and proliferated, FIG. 1C), did not inhibit proliferation of T cells (B-LPS, FIG. 3A).

Figure 3C:
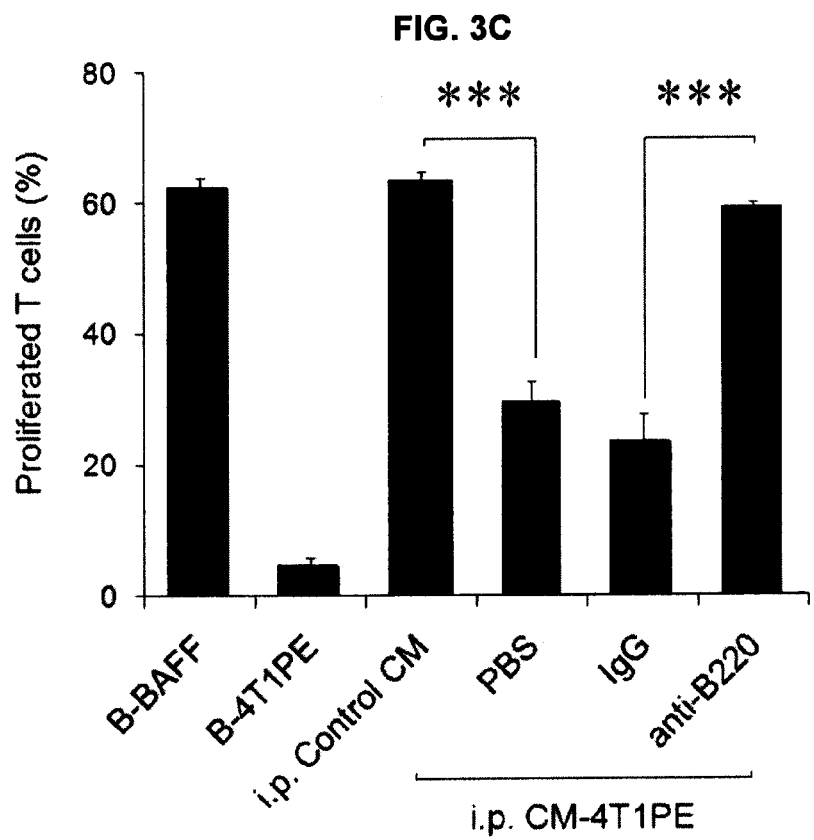
Figure 3D:
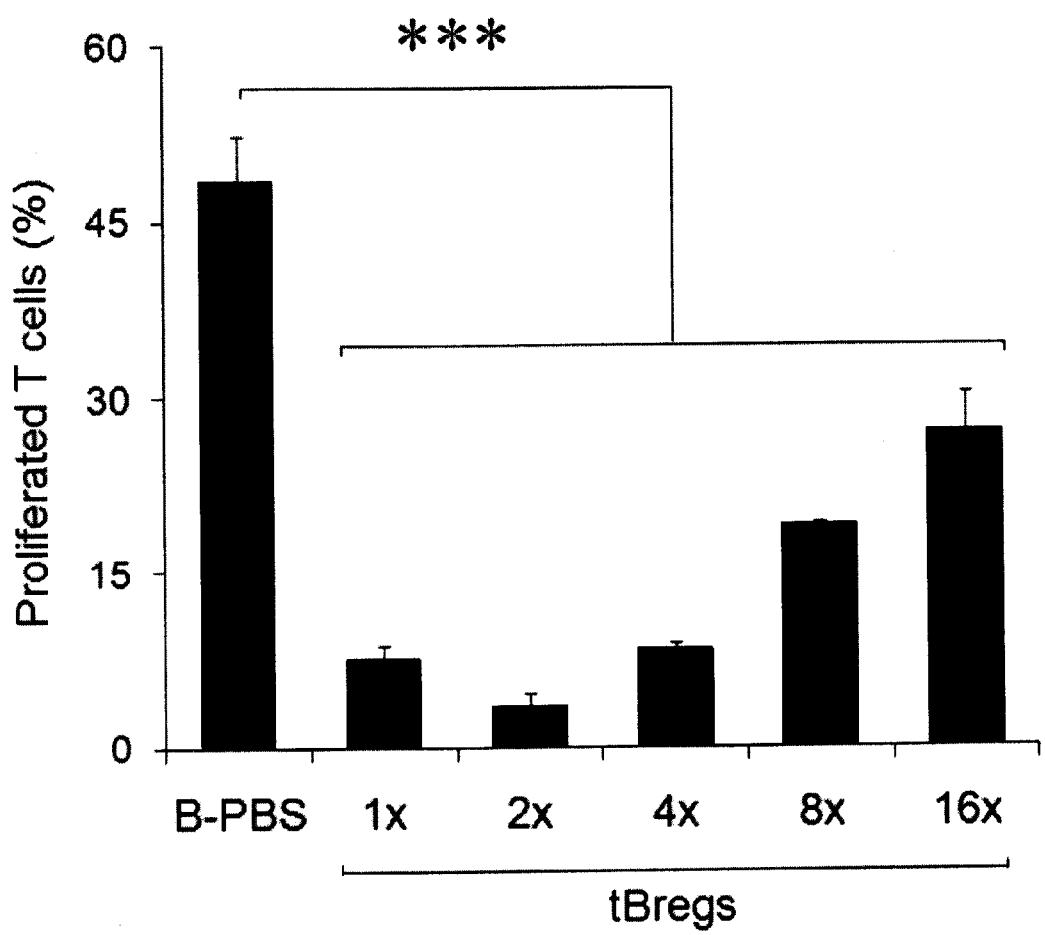
Figure 8B:
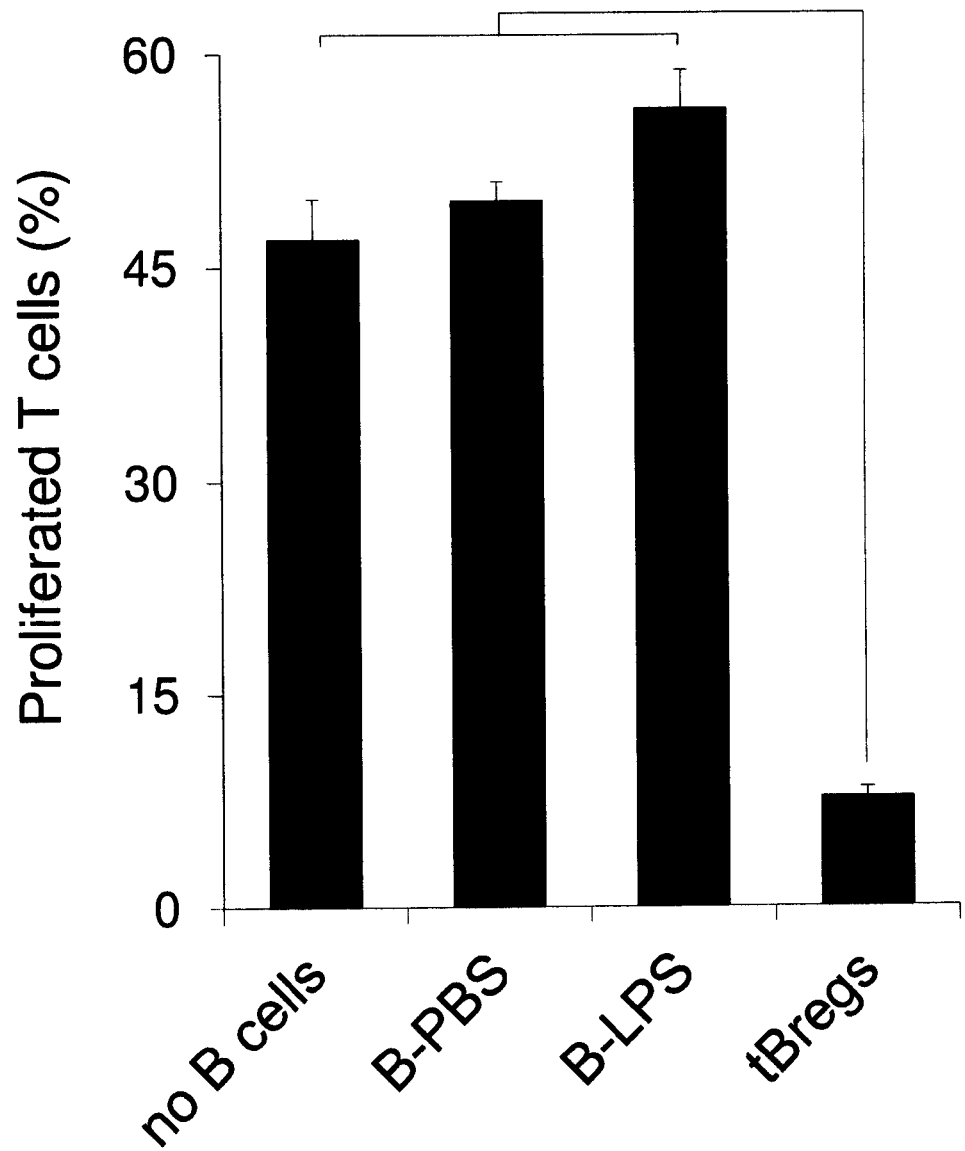
Figure 8C:
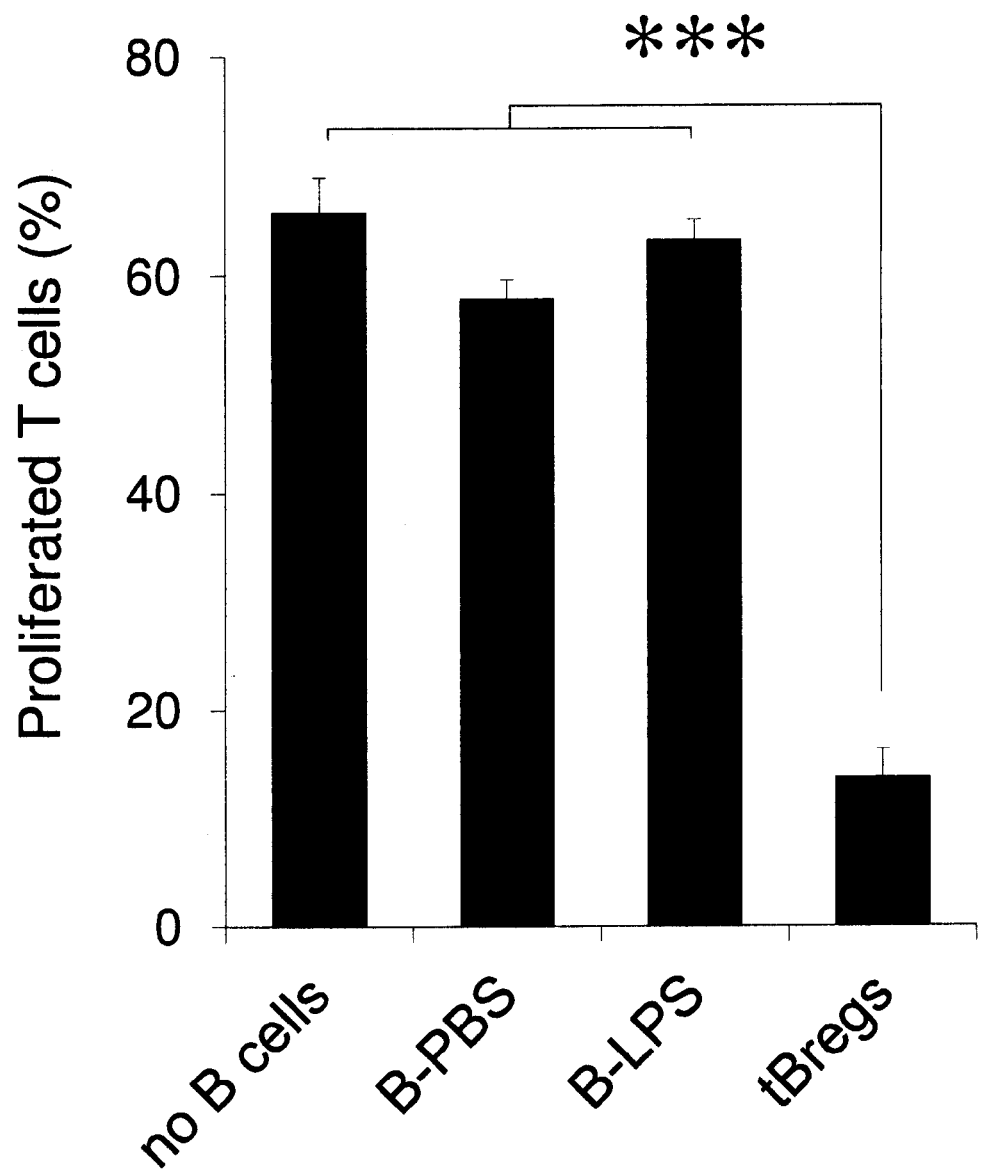
Figure 8D:
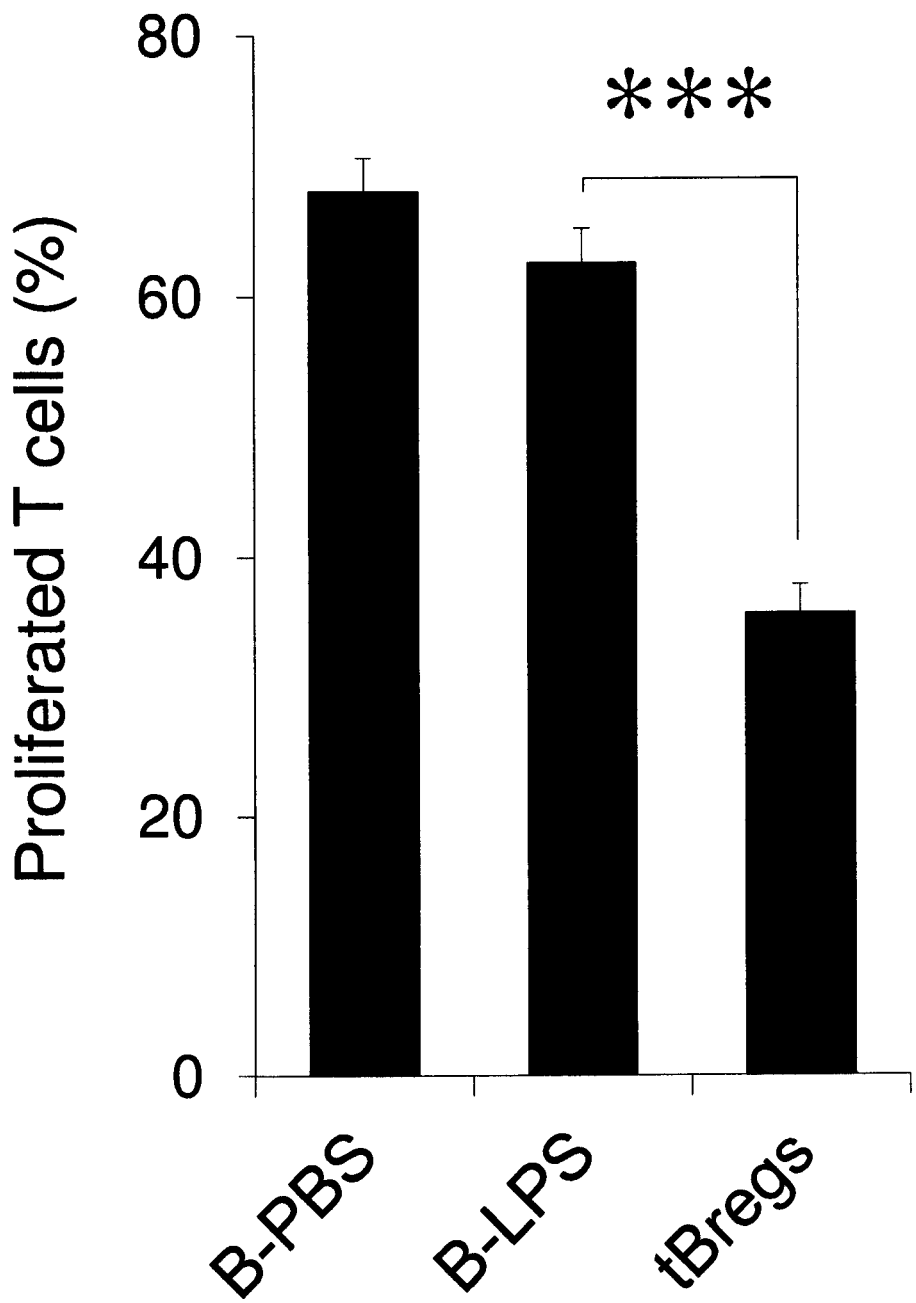

In order to demonstrate that the suppressive B cells can be also generated in vivo, splenic CD19+ B cells were purified from BALB/C mice injected with CM-4T1PE (as in FIG. 1B) and cultured with T cells stimulated with anti-CD3/CD28 Ab and IL-2. Indeed, only the B cells from CM-4T1PE-injected, but not control mock-treated (i.p. control CM), mice inhibited T cell responses (i.p. CM-4T1PE, FIG. 3C). Since the inhibition was completely prevented if B220+ cells were removed from the suppression assay (anti-B220, i.p. CM-4T1PE, FIG. 3C), collectively the data indicate that non-metastatic 4T1 cell subsets induce the generation of CD19+B220+ B cells that possess regulatory activity. The cells (designated tumor-evoked Bregs, tBregs) inhibited proliferation of resting and pre-activated T cells equally well in a mouse strain-independent way (FIG. 8B-D) even when used at a 1:16 ratio of B cells to T cells (FIG. 3D).

Figure 4A:
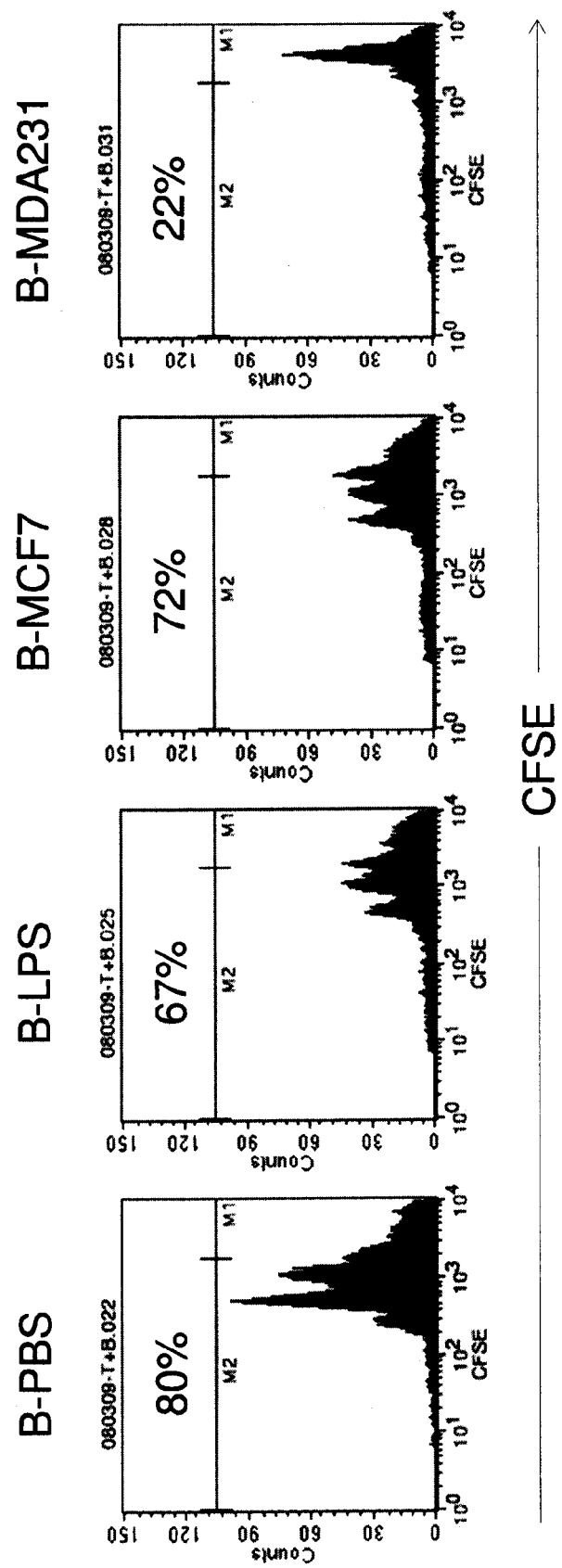
Figure 4B:
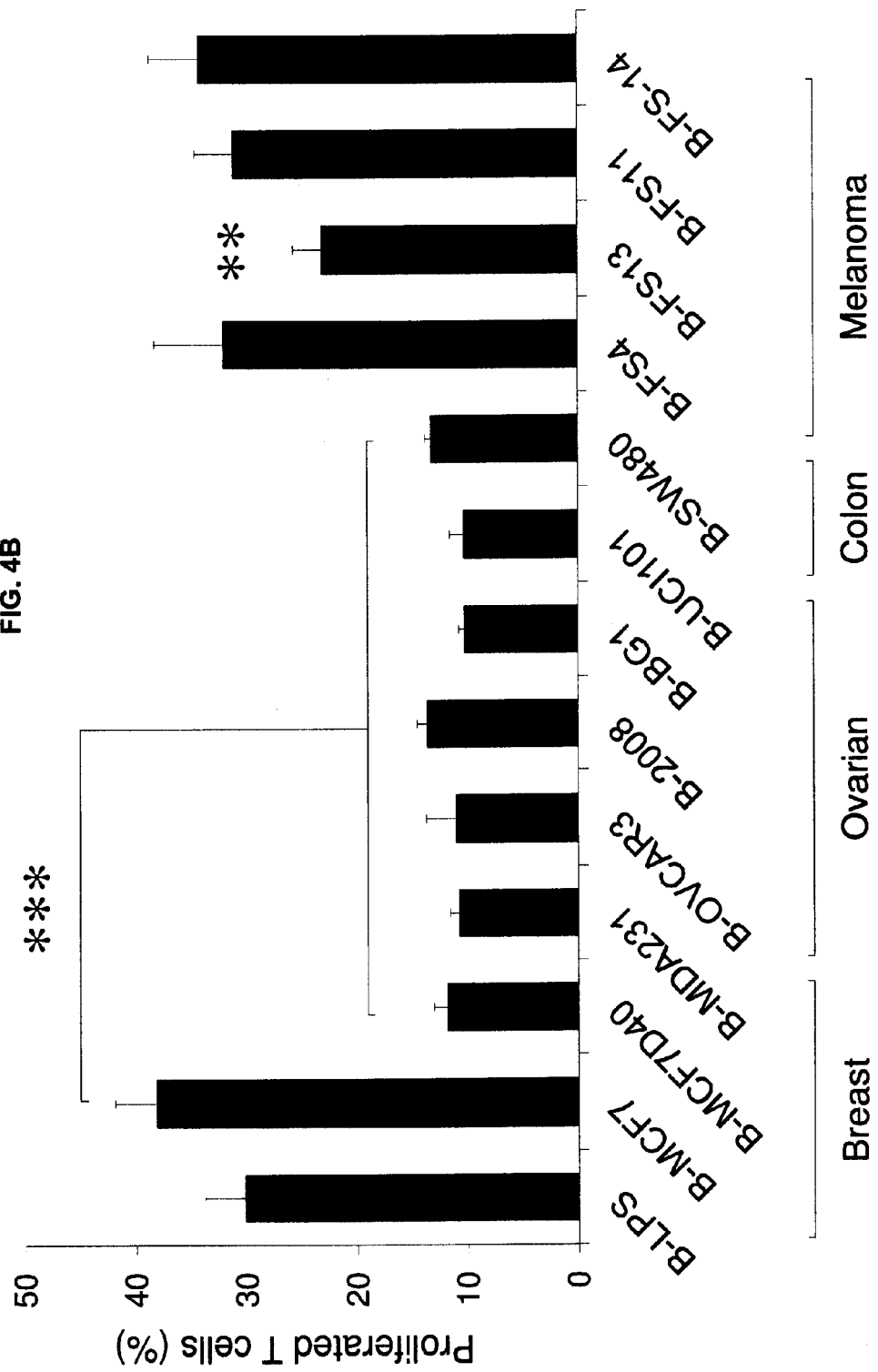
Figure 9D:
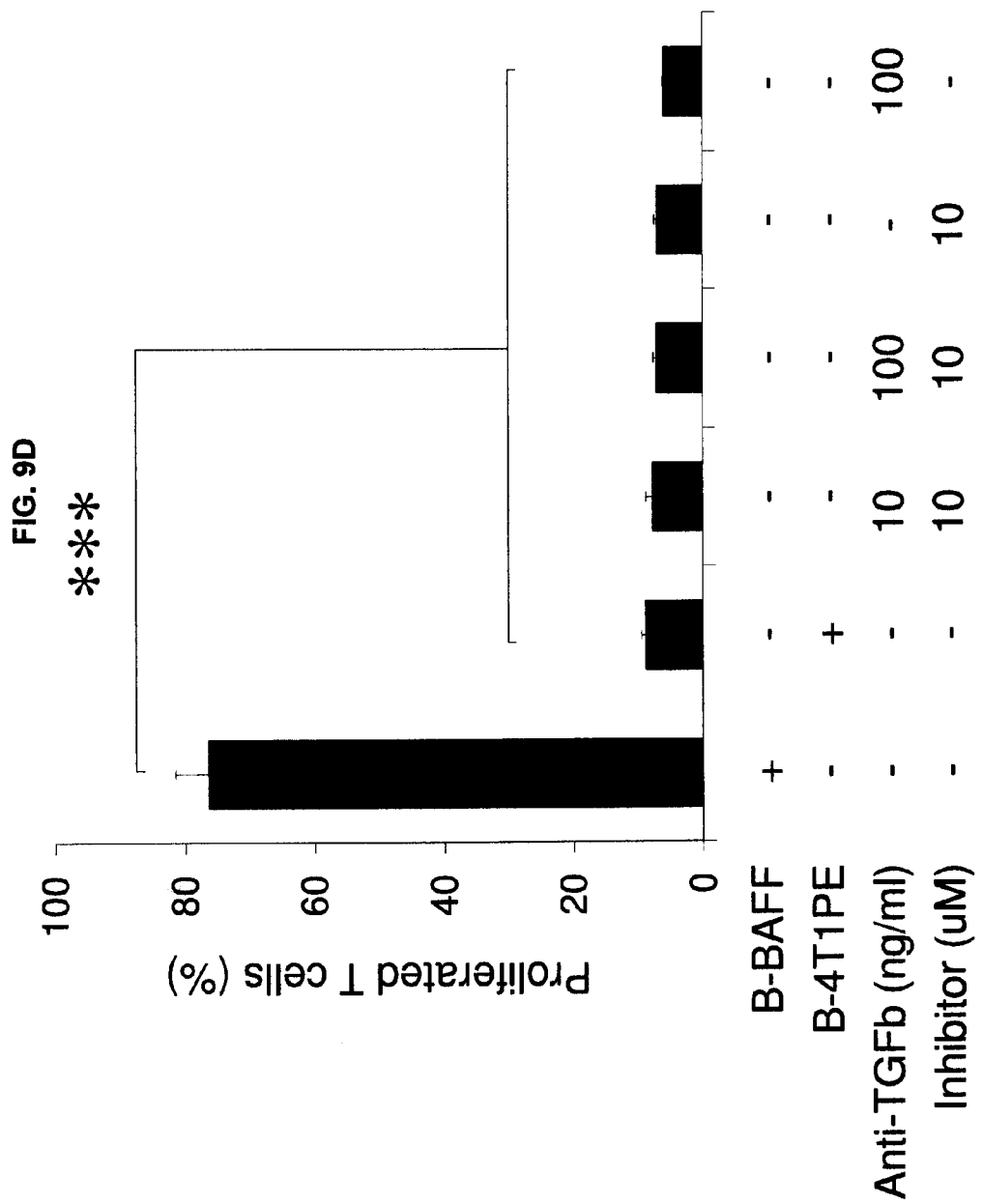

Human peripheral blood CD19+ B cells also up regulated CD25 after treatment with CM from human breast cancer MDA-MB-231 and MCF7 cells (FIG. 9A), suggesting that they may also generate tBregs. To test this idea, B cells-treated with CM of MDA-MB-231 and MCF7 breast cancer cells (CM-MDA231 and CM-MCF7, respectively), or cultured with or without LPS were washed and mixed with CD3+ T cells stimulated with anti-CD3/CD28 Abs and IL-2. In contrast to B cells treated with LPS or CM-MCF7, the B cells cultured in CM-MDA231 almost completely inhibited proliferation of T cells (B-MDA231, FIG. 4A), both CD4+ and CD8+ T cells. Moreover, T cell proliferation was also inhibited by B cells-treated with CM from other human cancers, including ovarian and colon (FIG. 4B). Thus, human cancers also induce the generation of tBregs.

Figure 4D:
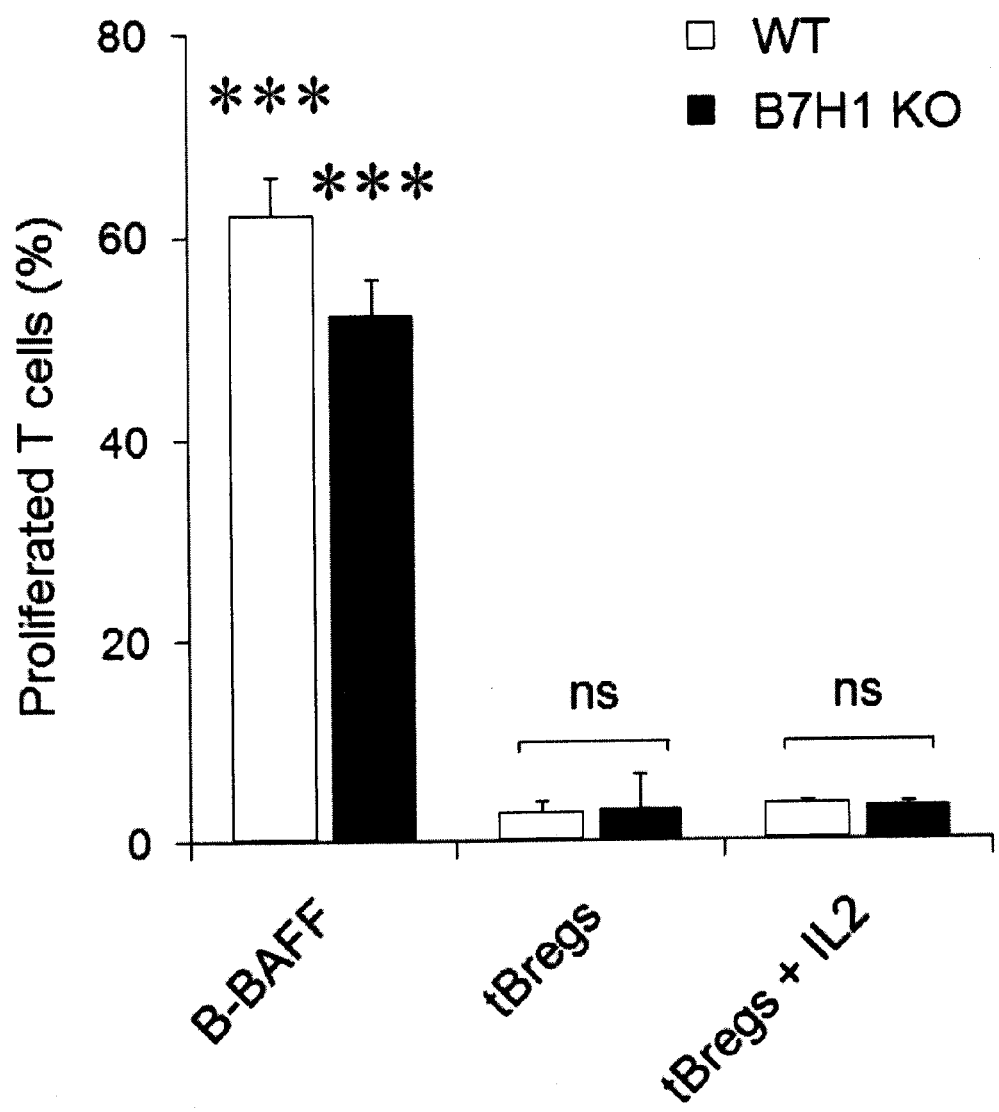
Figure 9E:
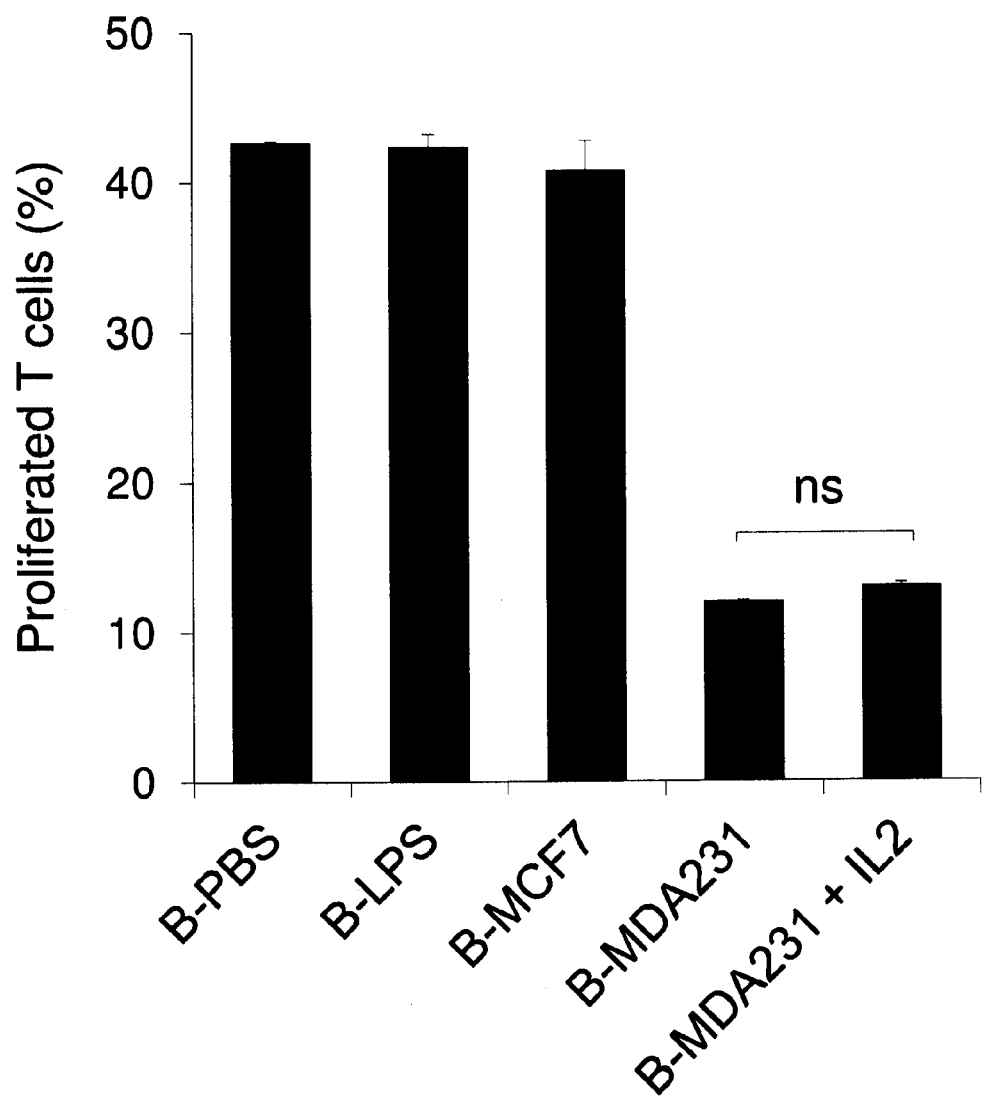
Figure 9F:
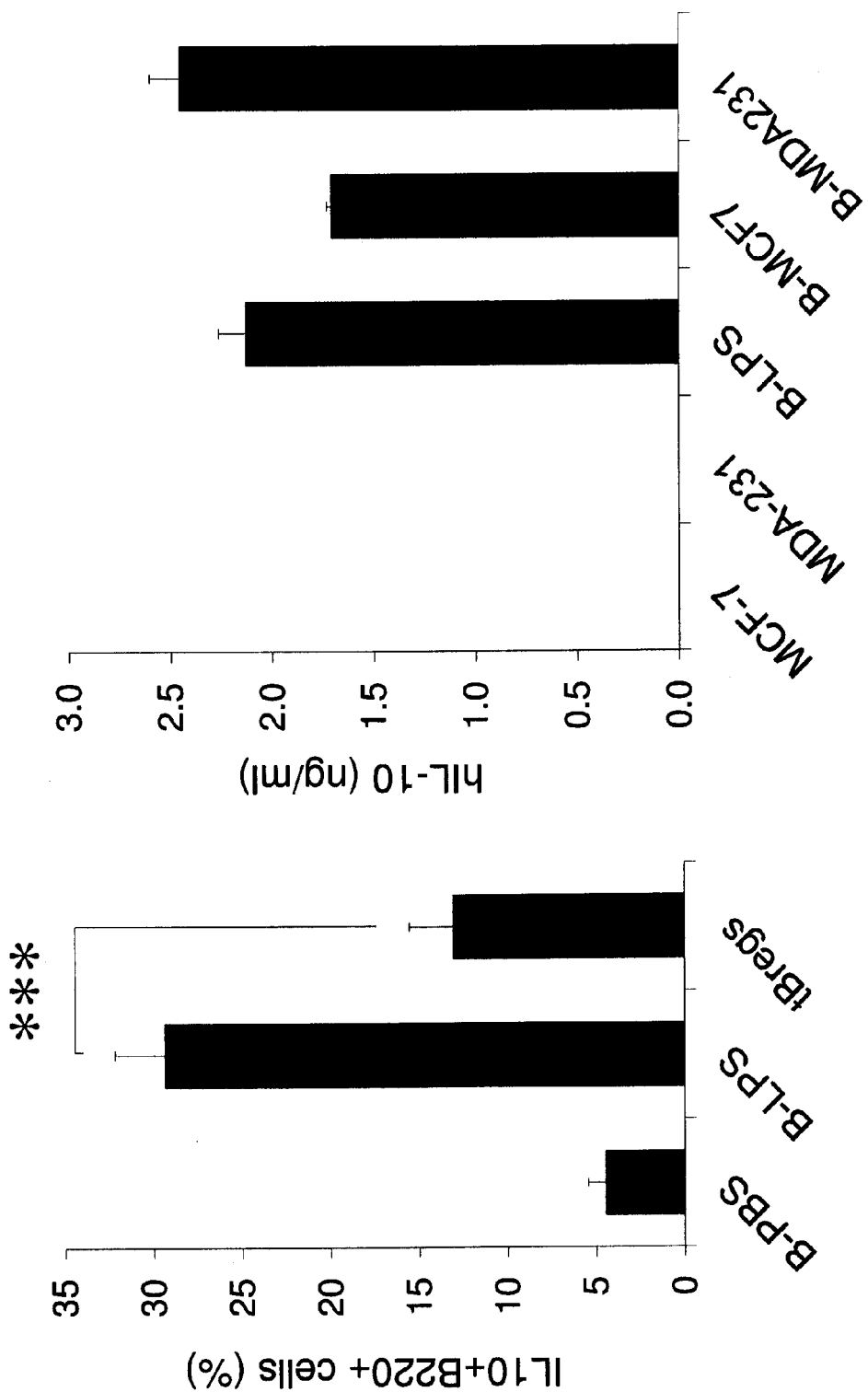
Figure 9G:
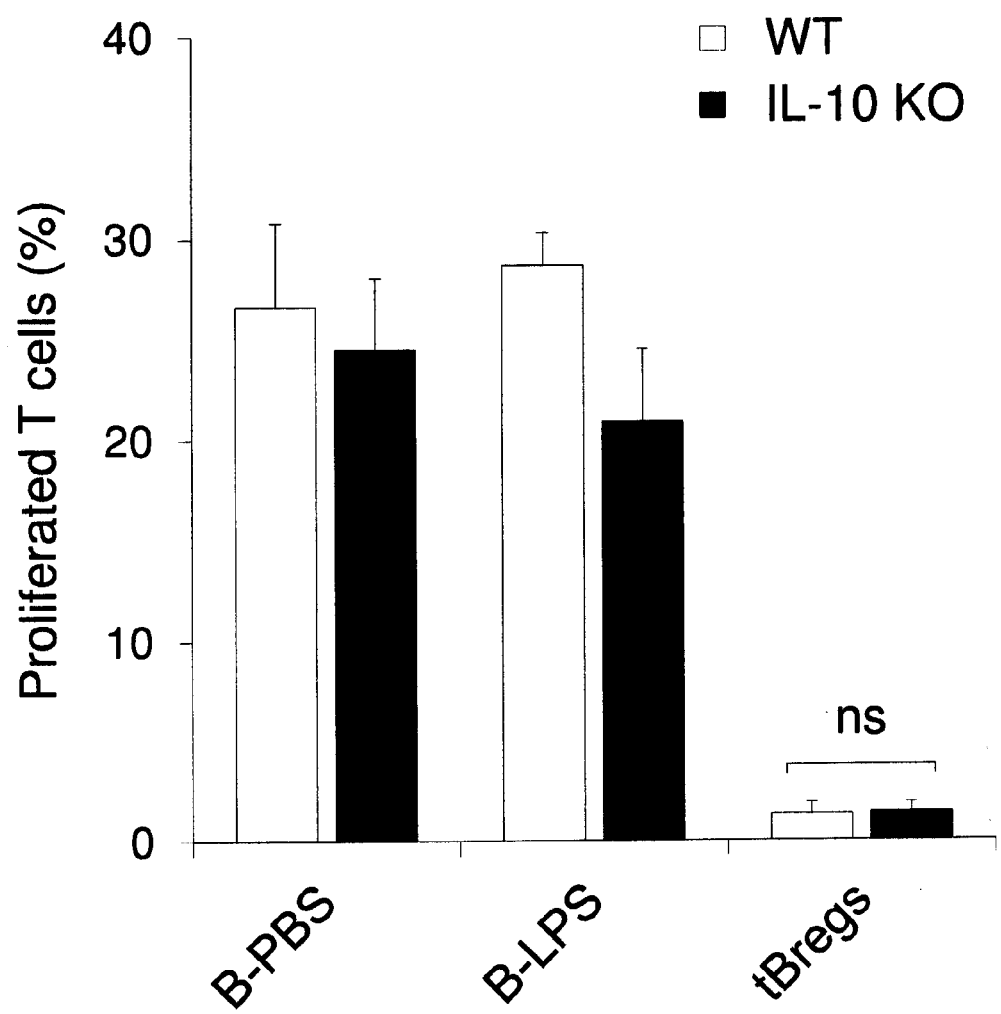

Interestingly, tBregs required cell-contact to exhort suppression by presumably utilizing soluble factors, as the tBregs' inability to suppress T cells when physically separated by a porous membrane was reversed if tBregs were also mixed with T cells (FIG. 4C). However, the suppression did affect viability of T cells and did not involve common regulatory pathways reported. For example, the T cell suppression was not affected in tBregs from mice with deficient B7-H1 (FIG. 4D) and Fas (FIG. 9B, C), or by inactivation of TGFβ, IL-10 and IL-27 and IL-35 (the factors abundantly expressed in tBregs, FIG. 9D-G). Lastly, the IL-2 competition theory can be also ruled out, as the suppression was not affected by the presence of high doses of IL-2 (FIG. 4D and FIG. 9E).

Figure 5A:
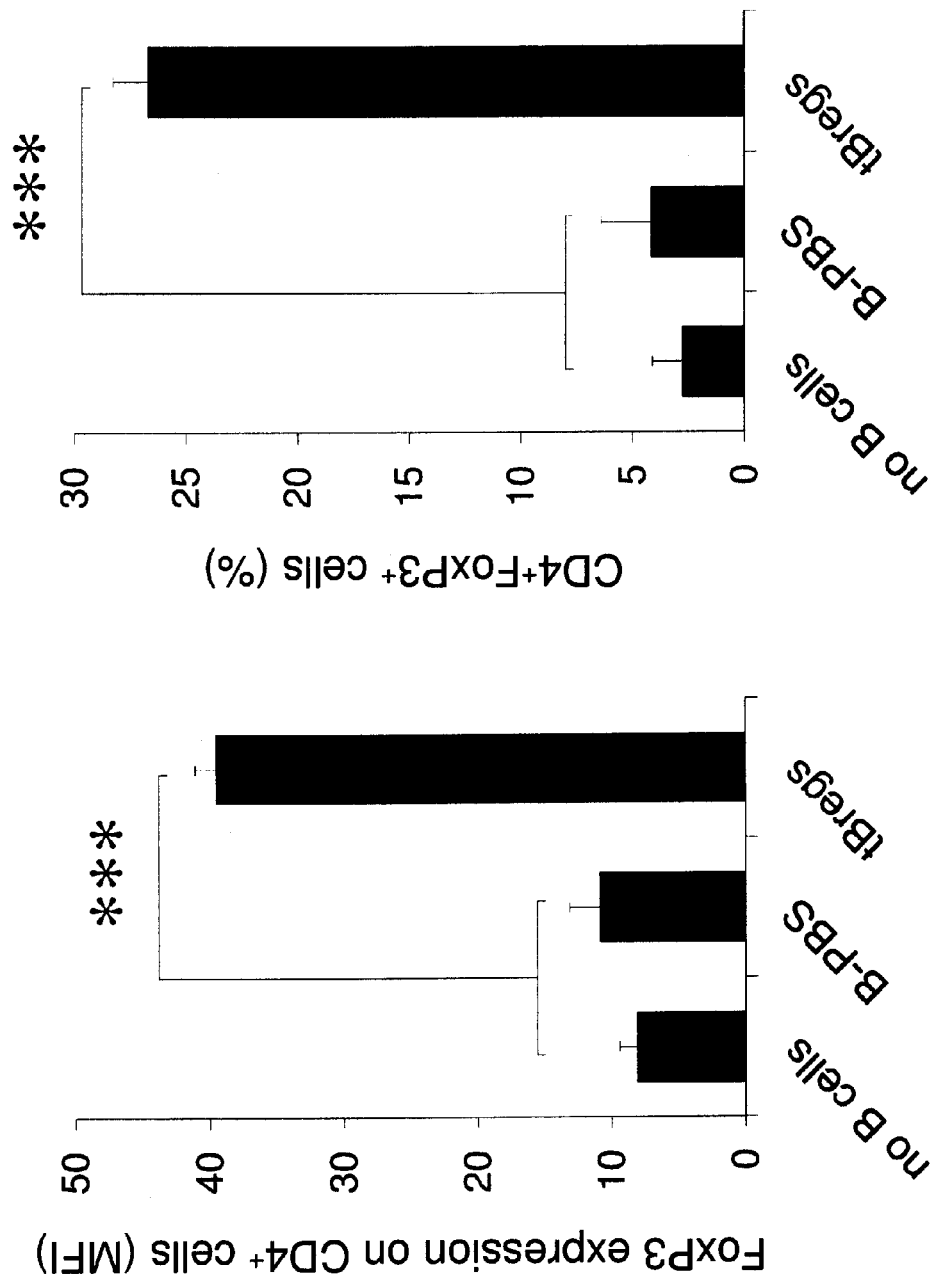
FIG. 5A-5D are a set of graphs. (A) tBregs promote Treg conversion in vitro. tBregs were co-cultured with purified non-Treg CD4$^+$ T cells for five days in the presence anti-CD3/CD28 Abs and 500 U/ml IL-2. Y-axis shows mean fluorescence intensity (MFI, left panel) and percentage (right panel) of FoxP3$^+$ within CD4$^+$ T cells. The newly converted FoxP3$^+$ cells have regulatory activity (B), as they (after two rounds of depletion of B cells with a bead-coupled anti-CD19 and anti-B220 Abs, >98% pure CD4$^+$ cells) suppressed proliferation of CFSE-labeled CD8$^+$ T cells stimulated with anti-CD3/CD28 Abs and 500 U/ml IL-2 for five days at the indicated E:T ratio. Y-axis shows percentage of proliferated CFSE-labeled CD8$^+$ cells of a representative and triplicate experiment repeated twice. P values are for comparisons between tBreg-(black bars) and normal B cell-(grey bars) treated CD4$^+$ T cells. (C) tBregs, but not normal B cells, expand FoxP3$^+$CD4$^+$ T cells in vivo. Three naïve BALB/C mice per group were i.p. injected with 10$^7$ B cells and the proportion of FoxP3$^+$CD4$^+$ T cells (%±SEM, Y-axis) was evaluated after 5 days in the blood and spleens by FACS. (D) Poor growth of B16 melanoma in mice deficient in mature B cells (JHT KO) can be reversed by adoptive transfer of congeneic tBregs (splenic B cells from naïve C57BL/6 mice treated with CM-4T1PE as in FIG. 1C). The data are from five per group C57BL/6 and JHT KO (C57BL/6 background) mice s.c. challenged with B16 melanoma cells (10$^5$).
Figure 5B:
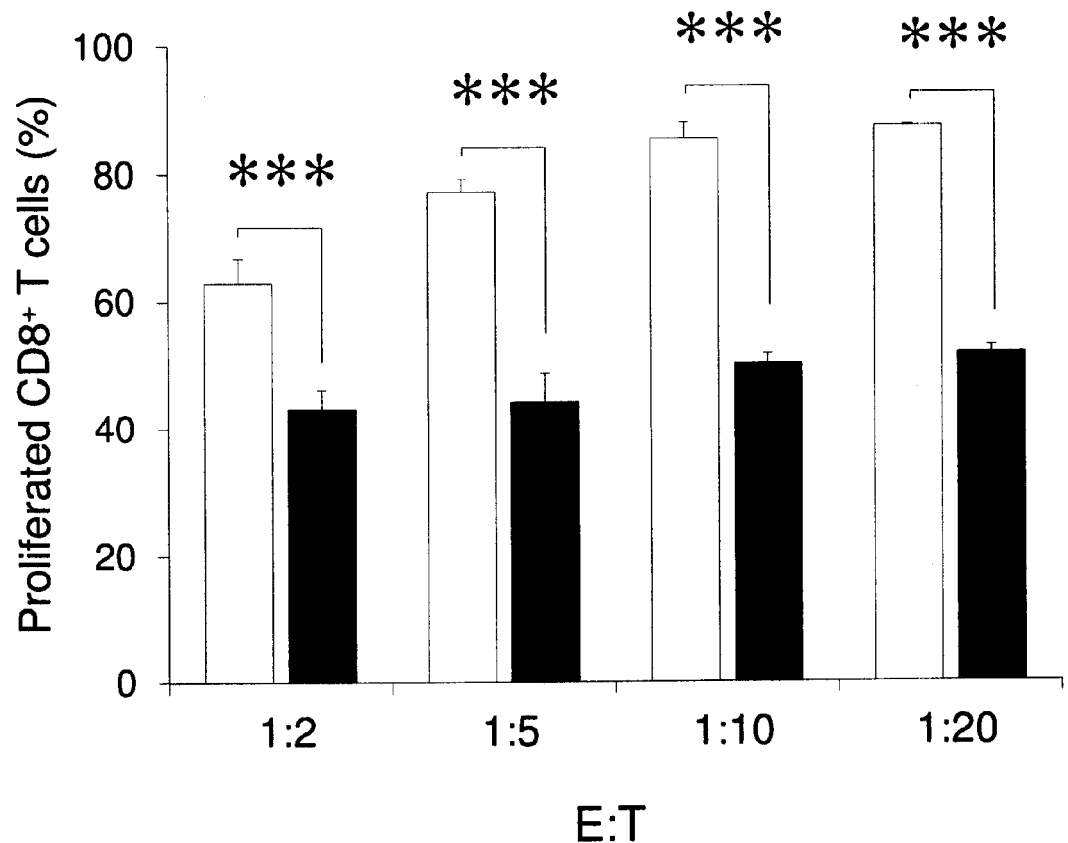
Figure 5C:
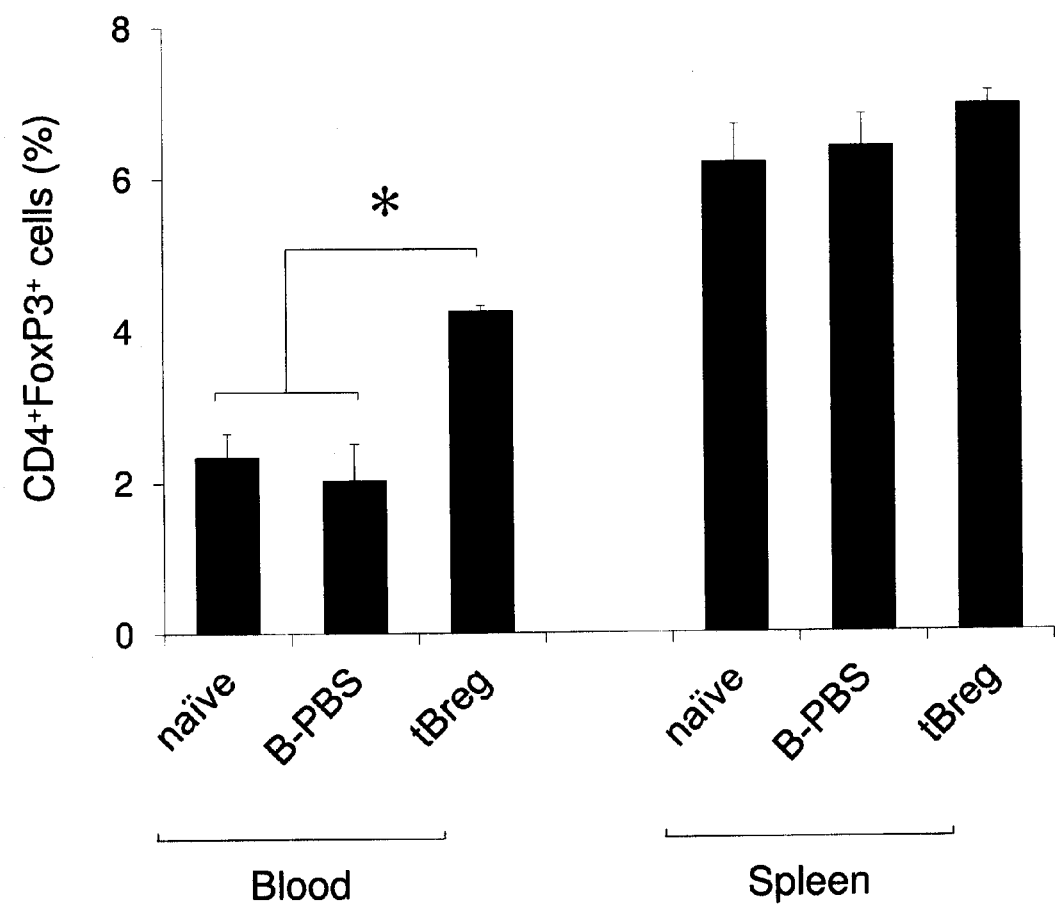
Figure 10:
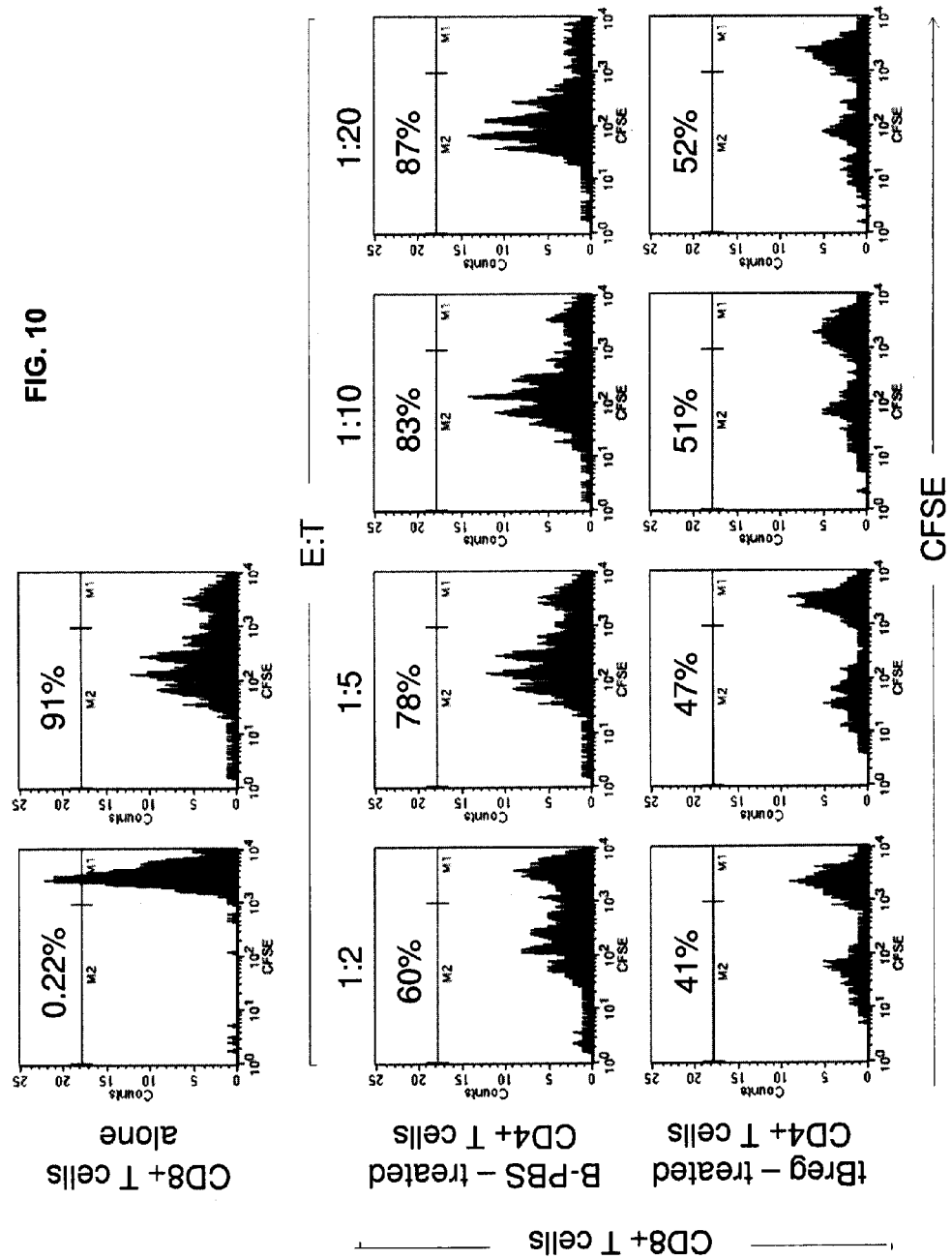
FIG. 10 is a set of plots. To demonstrate that the newly converted $FoxP3^+$ cells have regulatory activity, B cells were depleted from $CD4^+$ cells after 5 days co-incubation in the presence of anti-CD3/CD28 Abs and 500 U/ml IL-2, and mixed with CFSE-labeled $CD8^+$ T cells at the indicated E:T ratio and stimulated with anti-CD3/CD28 Abs in the presence of 500 U/ml IL-2 for five days. Numbers in histograms show percentage of proliferated CFSE-labeled $CD8^+$ cells of a representative and triplicate experiment repeated twice.

Example 5 tBregs Induce the Generation of Foxp3+ Tregs and Thereby Support Lung Metastasis Since tBregs expressed high levels of MHC class II molecules and all necessary co-stimulatory molecules (FIG. 1D), it was determined whether tBregs also induce conversion of Tregs. Purified non-regulatory CDe T cells (CD25−FoxP3− CD4+, non-Tregs) were stimulated with anti-CD3/CD28 Abs and high doses of IL-2 in the presence of tBregs or mock-treated B cells. Indeed, significant FoxP3 expression was only detected in non-Tregs co-cultured with tBregs (FIG. 5A). Since FoxP3 is a key marker of Tregs (Fontenot et al., NatImmunol. 2003; 4:330-6), the data indicate that tBregs induced Treg differentiation from resting T cells. To prove this, the CD4+ T cells (non-Tregs co-cultured with control B cells or tBregs) were re-isolated by two rounds of B cell depletion (using anti-CD19 and -B220 Abs which resulted in at least 98% pure T cells) and tested for their ability to inhibit proliferation of naïve CD8+ T cells stimulated with anti-CD3/CD28 Ab in the presence of 500 U/ml IL-2. The CD8+ T cell proliferation was only inhibited when they were cultured with the tBreg-generated FoxP3+ T cells, but not with T cells incubated with control B cells (FIG. 5B and FIG. 10). However, tBregs were unable to significantly affect expansion of pre-existing Tregs, suggesting that tBregs primarily induce conversion of Tregs. This ability to convert Tregs may also explain a previous finding that lung metastasis required and was associated with increased Treg numbers (Olkhanud et al., Cancer Res. 2009; 69:5996-600). Indeed, as in 4T1 cancer-bearing mice (Olkhanud et al., Cancer Res. 2009; 69:5996-600), naïve BALB/C mice transferred with tBregs, but not mock-treated B cells (B-PBS) contained significantly enhanced numbers of FoxP3+ Tregs in peripheral blood (and at lesser degrees in spleens, though it did not reach statistical significance) (FIG. 5C). This likely is not result of differential Treg recruitment, as CM from tBregs induced in vitro chemotaxis of resting CD4+ T cells, non-Tregs and Tregs, equally well utilizing CCL4/CCR5 pathway.

Figure 5D:
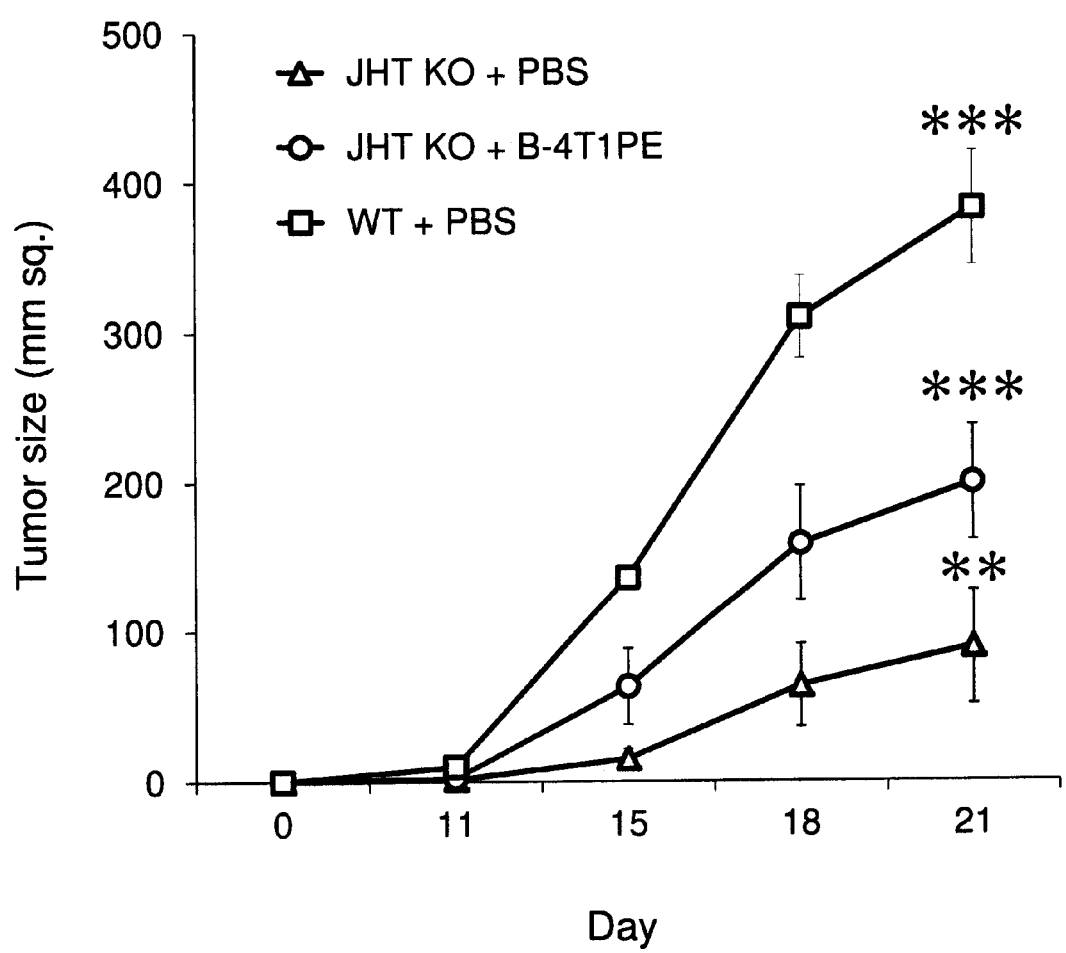
Figure 6B:
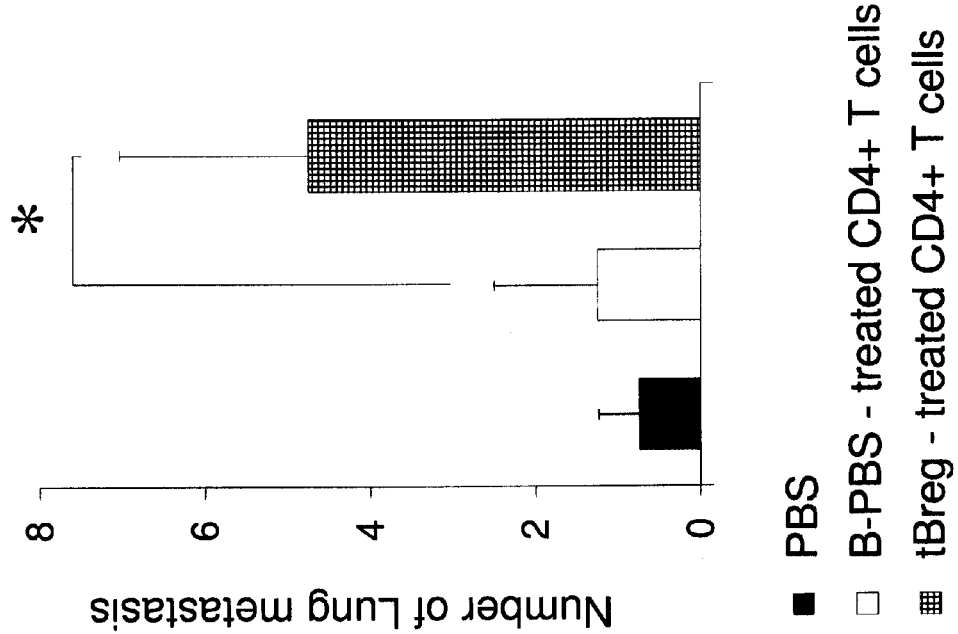
Figure 6A:
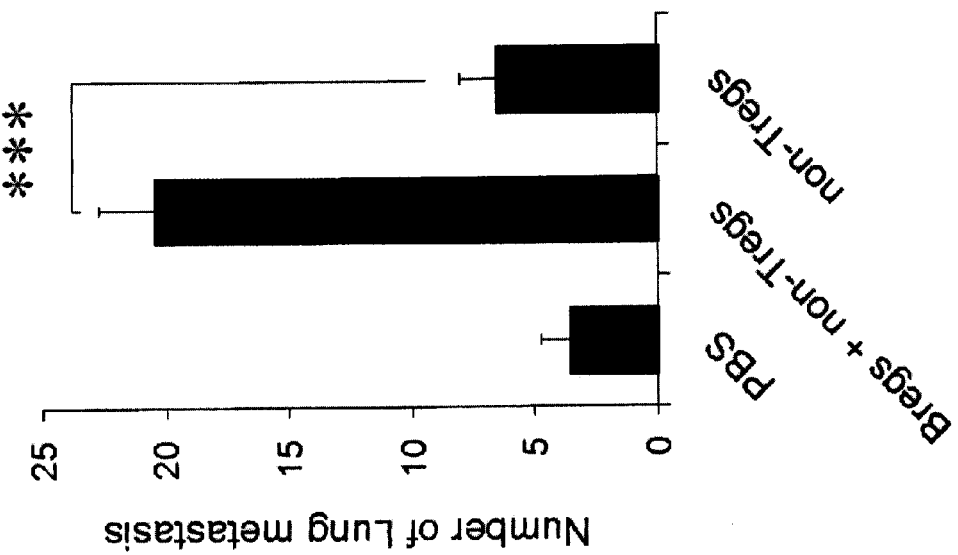
Figure 6C:
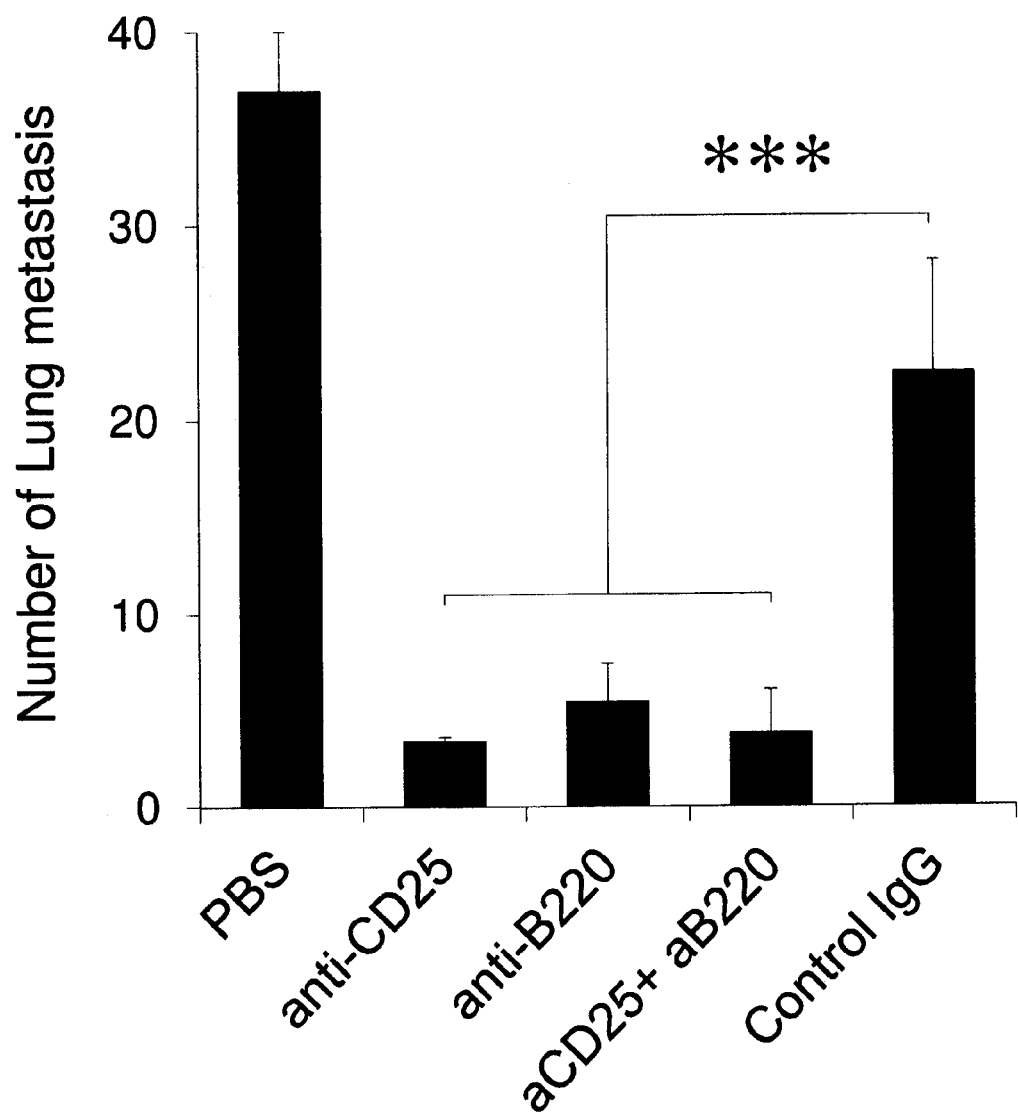

To prove the in vivo importance of tBregs, mice were challenged that do not have mature B cells (Gu et al., Cell. 1993; 73:1155-64) with B16 melanoma cells (as no congeneic mice were available to test 4T1 cells). The mice could not support the growth of melanoma unless they were adoptively transferred with congeneic tBregs generated by treating them with CM-4T1PE (JHT KO+tBregs, FIG. 5D). Next, to demonstrate that tBregs support metastasis by converting Tregs, T and B cell deficient NOD/SCID mice were utilized that do not support metastasis of 4T1 cancer cells unless adoptively transferred with Tregs (Olkhanud, supra). While control mice transferred with either tBregs alone or non-Tregs were almost free of lung metastasis (FIG. 6A), the mice that received ex vivo-generated tBregs together with non-Tregs from BALB/C mice succumbed to massive lung metastasis (FIG. 6A), suggesting that the process utilized tBreg-induced Tregs. Indeed, the transfer of newly in vitro converted Tregs (cultured with tBregs and then depleted of tBregs, >98%, see FIG. 5B), but not normal B cell-treated T cells, also restored the ability of 4T1 cells to metastasize in NOD/SCID mice (FIG. 6B). On the other hand, 4T1 cancer-bearing mice treated with antibody targeting B220 or CD25 (PC61, routinely used for Treg depletion) not only reduced CD25+B220+ CD19+ B cell numbers, but also almost completely abrogated lung metastases in 4T1 cancer-bearing BALB/C mice, while control IgG-treated mice succumbed to massive lung metastases (FIG. 6C). Hence, cancer metastasis can be controlled by controlling tBregs.

B cells are not known to facilitate cancer immune escape or metastasis, although the existence of regulatory B cells, such as B10 cells and B1b cells in mice, see Shimomura et al., IntImmunol. 2008; 20:729-37, Mizoguchi et al., Immunity. 2002; 16:219-30) and CD19+CD24$^{High}$CD38$^{High}$ B cells in humans (Tretter et al., J. Immunol. 2007; 179:7225-32) that alleviate autoimmune diseases have been reported. Proof is provided herein that breast cancer metastasis also requires a unique and poorly proliferative subset of regulatory B cells, tBregs, which, unlike other Bregs or memory-type suppressive B cells, do not express CD27 and CD5 or up regulate CD1d. The tBregs also express constitutively active STAT3 and high levels of CD25, CD19, B220, IgD, B7-H1, CD69, CD86 and low levels of IgM and CD62L. In some embodiments, tBregs can be phenotypically defined as poorly proliferative CD19$^+$ B cells that are pStat3$^+$CD25$^{High}$B7-H1$^{High}$CD86$^{High}$CCR6$^{High}$ and CD62L$^{Low}$IgM$^{Int/Low}$. B cells treated with S. aureus Cowan 1 antigen also up regulate CD25 but induce anergy of activated T cells competing for IL-2 (Tretter et al., Blood. 2008; 112:4555-64). However, the tBregs described herein efficiently inhibit both resting and activated T cells, including CD4$^+$ and CD8$^+$ T cells, without induction of cell death or use of IL-2. tBregs also differ functionally from other Bregs which often utilize IL-10-dependent suppression. Unlike other Bregs (Matsushita et al., J Clin Invest. 2008; 118:3420-30; Yanaba et al., Immunity. 2008; 28:639-50; Mizoguchi et al., Immunity. 2002; 16:219-30) and LPS- or BCR-activated B cells (Fuchs et al., Science. 1992; 258:1156-9; Hussain and Delovitch, J. Immunol. 2007; 179:7225-32), the suppressive activity of tBregs did not require IL-10 or other known suppressive pathways, such as B7-H1-PD1, Fas-FasL, TGF, IL27/IL35.

Without being bound by theory, although cancer metastasis can be explained by the ability of tBregs to suppress T cell activity, the data presented herein indicate that the primary role of tBregs is to promote the conversion/expansion of Tregs. Although other APCs, such as Gr1$^+$MDSCs and M2 macrophages (DuPre et al., Int. J. Exp. Pathol. 2007; 88:351-60; Danna et al., Cancer Res. 2004; 64:2205-11; Sinha et al., J. Immunol. 2005; 174:636-45), can induce Treg generation and support metastasis, tBregs appear to be the primarily responsible for the generation of FoxP3$^+$Tregs. tBregs efficiently generated Tregs from non-Tregs in vitro and in vivo. Importantly, the adoptive transfer of non-Tregs together with tBregs, or tBreg-converted Tregs, but not non-Tregs or tBregs alone, elicited massive metastases in T and B cell deficient NOD/SCID mice which cannot support metastasis, unless Tregs are present. The fact that NOD/SCID mice that were transferred with non-Tregs do not support metastasis of 4T1 cells, although they have comparable capability to expand MDSCs with BALB/C mice, suggest that MDSCs did not efficiently convert Tregs.

Figure 11A:
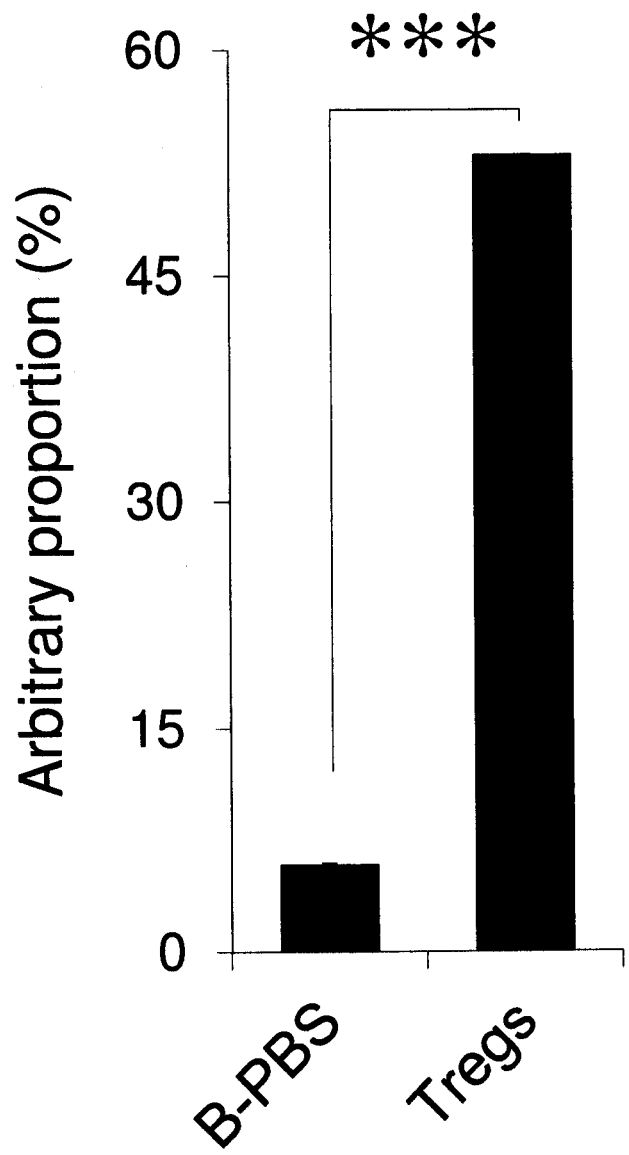
FIG. 11A-11B are bar graphs. The proportion (%) of $CD11^+Gr1^{Int}$ (MDSC) in 4T1 cancer-bearing NOD/SCID mice that was adoptively transferred with Tregs (A) or Gr1+ or other myeloid cells in cancer-bearing BALB/C mice that were depleted of Tregs and tBregs using anti-CD25 antibody (Ab) (B). Ab depletion is as in FIG. 5A.
Figure 11B:
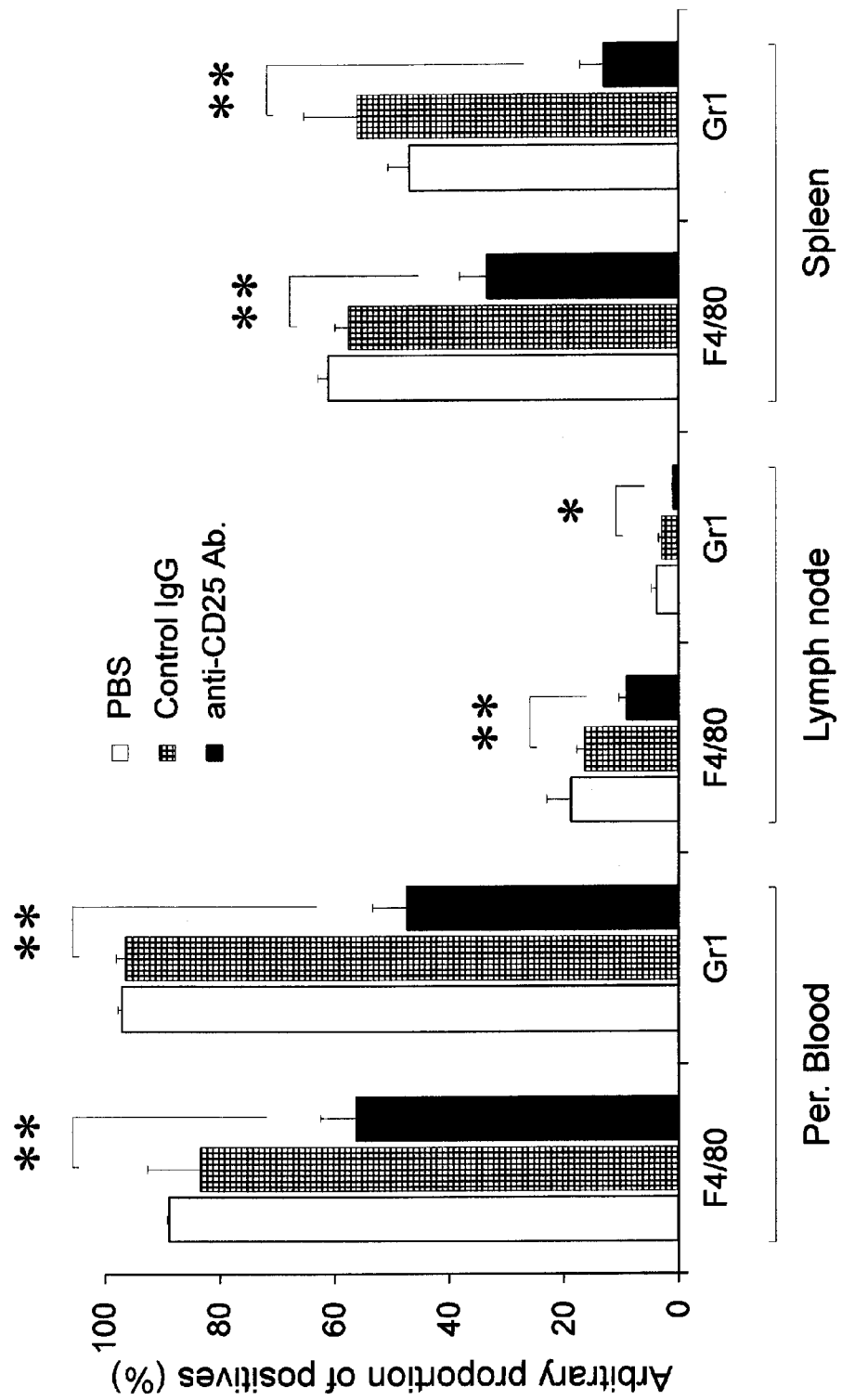

The expansion of MDSCs was positively correlated with the presence of Tregs, as their proportion was significantly elevated in NOD/SCID mice transferred with Tregs (FIG. 11A), and the depletion of Tregs in cancer-bearing BALB/C mice also reduced MDSCs numbers (FIG. 11B) without affecting the rate of the primary cancer growth. Without being bound by theory, Tregs and tBregs may cross-talk with MDSCs providing or receiving survival benefits. Collectively, as summarized in FIG. 6D, the finding of tBregs suggests the importance of CCR4$^+$ Tregs in inactivating antitumor NK cells to support lung metastasis. Although tBregs can directly inhibit activity of T cells (thus suppress adaptive antitumor immunity), tBregs can induce of Treg conversion from normal T cells.

tBregs are actively generated from normal B cells in response to cancer cell-produced factors. This appears to be quite a wide spread phenomenon, as a number of human cancer lines (breast, ovarian and colon carcinomas) also induced the generation of tBregs. Thus, as long as cancer persists, it can induce the generation of tBregs and thereby initiate the chain of suppressive events. Hence, tBregs need to be controlled to efficiently combat cancer. Thus, clinically available antibodies such as the pan B cell antibody, anti-CD20 antibody (rituximab) or the anti-IL2Rα antibody (daclizumab) could bypass the tBreg-mediated blockade of the immune response to some cancers.

Survival of tBregs is promoted by upregulating BAFF-Rand, and producing its ligand, BAFF. Without being bound by theory, although tBregs can efficiently suppress T cell responses, their primary role in metastasis is to induce conversion of FoxP3$^+$ Tregs from resting CD4$^+$ T cells. To effectively combat cancer and cancer metastasis, tBregs have to be controlled in order to interrupt the initiation of cancer-induced suppressive events. This identification is provided herein.

It will be apparent that the precise details of the methods or compositions described may be varied or modified without departing from the spirit of the described invention. We claim all such modifications and variations that fall within the scope and spirit of the claims below.

We claim:

1. An isolated population of regulatory B cells, wherein the B cells are CD25$^{High}$CD19$^+$ CD81$^{high}$CD23$^{lo}$IgD$^{high}$ IgM$^{Int/Low}$ B cells that do not express CD5, wherein the B cells do not proliferate in vitro, and wherein the B cells suppress T cells in cell contact-dependent manner.

2. The isolated population of regulatory B cells of claim 1, wherein the B cells express CD21.

3. The isolated population of regulatory B cells of claim 1, wherein the B cells express one or more of CD40, CD69, CD80, CD86, BAFF-R, CCR6, CXCR5 and MHC class I and II molecules.

4. The isolated population of regulatory B cells of claim 1, wherein the B cells express TSLPR, Fas, FasL and programmed death (PD)-1.

5. The isolated population of regulatory B cells of claim 1, wherein the B cells do not express CD27.

6. The isolated population of regulatory B cells of claim 1, wherein the B cells express phosphorylated STAT3.

7. The isolated population of regulatory B cells of claim 1 wherein the B cells are pStat3$^+$CD25$^{High}$B7-H1$^{High}$CD86$^{High}$CCR6$^{High}$ and CD62L$^{Low}$IgM$^{int/Low}$ B cells.

8. The isolated population of regulatory B cells of claim 1, wherein the B cells induce generation of FoxP3$^+$ regulatory T cells (Tregs) from CD8$^+$ and CD4$^+$ T cells.

9. The isolated population of regulatory B cells of claim 1, wherein the B cells promote regulatory T cell (Treg)-dependent metastasis when introduced into a T cell deficient host.

10. A pharmaceutical composition comprising the isolated population of B cells of claim 1; and
a tissue culture medium or a buffered saline solution.

11. The pharmaceutical composition of claim 10, further comprising a chemotherapeutic agent.

12. The pharmaceutical composition of claim 10, wherein the chemotherapeutic agent is fluorouracil, methotrexate, paclitaxel, fludarabine, etoposide, doxorubicin, or vincristine.

13. The pharmaceutical composition of claim 10, further comprising an anti-inflammatory agent.

14. The pharmaceutical composition of claim 13, wherein the anti-inflammatory agent is a non-steroidal anti-inflammatory agent.

15. The pharmaceutical composition of claim 10, further comprising an additional agent, wherein the additional agent is an anti-inflammatory agent, and wherein the anti-inflammatory agent is hydrocortisone, dexamethasone or prednisone, acetylsalicylic acid, ibuprofen or naproxen sodium.

16. The pharmaceutical composition of claim 10, further comprising an additional agent.

* * * * *